(12) United States Patent
Kong et al.

(10) Patent No.: US 7,598,269 B2
(45) Date of Patent: Oct. 6, 2009

(54) METHODS AND COMPOSITIONS FOR TREATING AMYLOID-RELATED DISEASES

(75) Inventors: Xianqi Kong, Dollard-des-Ormeaux (CA); Walter A. Szarek, Kingston (CA); Francine Gervais, Ile Bizard (CA)

(73) Assignee: Bellus Health (International) Limited, Lausanne (CH)

( * ) Notice: Subject to any disclaimer, the term of this patent is extended or adjusted under 35 U.S.C. 154(b) by 0 days.

(21) Appl. No.: 11/807,759

(22) Filed: May 30, 2007

(65) Prior Publication Data

US 2008/0015180 A1 Jan. 17, 2008

Related U.S. Application Data

(63) Continuation of application No. 10/871,365, filed on Jun. 18, 2004, now Pat. No. 7,244,764.

(60) Provisional application No. 60/480,906, filed on Jun. 23, 2003, provisional application No. 60/512,047, filed on Oct. 17, 2003.

(51) Int. Cl.
*A61K 31/44* (2006.01)
*A61K 31/47* (2006.01)
*C07D 211/00* (2006.01)

(52) U.S. Cl. ..................... 514/315; 546/184
(58) Field of Classification Search ............... 514/315; 546/184
See application file for complete search history.

(56) References Cited

U.S. PATENT DOCUMENTS

| | | | |
|---|---|---|---|
| 2,531,468 A | 11/1950 | Reynolds | |
| 3,218,352 A | 11/1965 | Frifelder et al. | |
| 3,236,881 A | 2/1966 | Distler et al. | |
| 3,658,966 A | 4/1972 | Tsunoo et al. | |
| 3,872,125 A | 3/1975 | Houlihan et al. | |
| 3,920,833 A | 11/1975 | Cook et al. | |
| 4,085,134 A | 4/1978 | Redmore et al. | |
| 4,187,245 A | 2/1980 | Redmore et al. | |
| 4,199,601 A | 4/1980 | Durlach | |
| 4,255,448 A | 3/1981 | Fariello | |
| 4,267,194 A | 5/1981 | Durlach | |
| 4,271,189 A | 6/1981 | Durlach | |
| 4,355,043 A | 10/1982 | Durlach | |
| 4,386,081 A | 5/1983 | Helgstrand et al. | |
| 4,448,779 A | 5/1984 | Blanchard et al. | |
| 4,522,811 A | 6/1985 | Eppstein et al. | |
| 4,528,184 A | 7/1985 | Kurono et al. | |
| 4,540,564 A | 9/1985 | Bodor | |
| 4,563,470 A | 1/1986 | Durlach | |
| 4,713,376 A | 12/1987 | Kuzuya et al. | |
| 4,737,353 A | 4/1988 | Flanigen et al. | |
| 4,737,357 A | 4/1988 | Lehmann et al. | |
| 4,847,082 A | 7/1989 | Sabin | |
| 4,956,347 A | 9/1990 | Ban et al. | |
| 5,017,566 A | 5/1991 | Bodor | |
| 5,023,252 A | 6/1991 | Hseih | |
| 5,024,998 A | 6/1991 | Bodor | |
| 5,039,794 A | 8/1991 | Wier et al. | |
| 5,064,923 A | 11/1991 | Kashihara et al. | |
| 5,112,863 A | 5/1992 | Hashimoto et al. | |
| 5,124,146 A | 6/1992 | Neuwelt | |
| 5,153,179 A | 10/1992 | Eibl | |
| 5,164,295 A | 11/1992 | Kisilevsky et al. | |
| 5,166,320 A | 11/1992 | Wu et al. | |
| 5,177,064 A | 1/1993 | Bodor | |
| 5,192,753 A | 3/1993 | McGeer et al. | |
| 5,194,654 A | 3/1993 | Hostetler et al. | |
| 5,242,932 A | 9/1993 | Gandy et al. | |
| 5,254,342 A | 10/1993 | Shen et al. | |
| 5,258,402 A | 11/1993 | Maryanoff | |
| 5,270,312 A | 12/1993 | Glase et al. | |
| 5,276,059 A | 1/1994 | Caughey et al. | |
| 5,284,876 A | 2/1994 | Shashoua et al. | |
| 5,318,958 A | 6/1994 | Kisilevsky | |
| 5,342,977 A | 8/1994 | Baschang et al. | |
| 5,374,548 A | 12/1994 | Caras | |
| 5,383,988 A | 1/1995 | Herrmann et al. | |
| 5,385,915 A | 1/1995 | Buxbaum et al. | |
| 5,389,623 A | 2/1995 | Bodor | |
| 5,399,331 A | 3/1995 | Loughrey et al. | |
| 5,405,834 A | 4/1995 | Bundgaard et al. | |
| 5,413,996 A | 5/1995 | Bodor | |
| 5,416,016 A | 5/1995 | Low et al. | |

(Continued)

FOREIGN PATENT DOCUMENTS

CA 2031433 6/1991

(Continued)

OTHER PUBLICATIONS

Ancsin, John B. et al, "The Heparin/Heparan Sulfate-binding Site on Apo-serum Amyloid A: Implications for the Therapeutic Intervention of Amyloidosis," *The Journal of Biological Chemistry*, vol. 274(11):7172-7181 (1999).
Aprile, Carlo et al, "Cardiac and pleuropulmonary AL amyloid imaging with technetium-99m labelled aprotinin," *European Journal of Nuclear Medicine*, vol. 22(12):1393-1401 (1995).
Axelrad, M.A. et al, "Further Characterization of Amyloid-Enhancing Factor," *Laboratory Investigation*, vol. 47(2):139-146 (1982).
Baures, Paul W. et al, "Discovering Transthyretin Amyloid Fibril Inhibitors by Limited Screening," *Bioorganic & Medicinal Chemistry*, vol. 6:1389-1401 (1998).
Beilstein Registry No. 3388511, 2-dibenzylamino-ethanesulfonic acid, Feb. 15, 1990.
Beilstein Registry No. 4261672, 2-<<<3-hydroxy-5-(hydroxymethyl)-2-methyl-4-pyridyl>methyl>amino<ethane sulphonic acid, Jul. 20, 1992: Iskander, MN et al, "Tansition-state analogues as inhibitors for GABA-aminotransferase," *Eur. J. Med. Chem.*, vol. 26:129-136 (1991).

(Continued)

*Primary Examiner*—Golam M. M. Shameem
*Assistant Examiner*—Susannah Chung
(74) *Attorney, Agent, or Firm*—McCarter & English, LLP

(57) ABSTRACT

Methods, compounds, pharmaceutical compositions and kits are described for treating or preventing amyloid-+related disease.

14 Claims, No Drawings

U.S. PATENT DOCUMENTS

| | | |
|---|---|---|
| 5,430,052 A | 7/1995 | Higashiura et al. |
| 5,434,137 A | 7/1995 | Black |
| 5,442,043 A | 8/1995 | Fukuta et al. |
| 5,463,092 A | 10/1995 | Hostetler et al. |
| 5,466,683 A | 11/1995 | Sterling et al. |
| 5,525,727 A | 6/1996 | Bodor |
| 5,527,527 A | 6/1996 | Friden |
| 5,643,562 A | 7/1997 | Kisilevsky et al. |
| 5,668,117 A | 9/1997 | Shapiro |
| 5,672,683 A | 9/1997 | Friden et al. |
| 5,728,375 A | 3/1998 | Kisilevsky et al. |
| 5,780,510 A | 7/1998 | Carney |
| 5,840,294 A | 11/1998 | Kisilevsky et al. |
| 5,858,326 A | 1/1999 | Kisilevsky et al. |
| 5,869,469 A | 2/1999 | Szarek et al. |
| 5,952,389 A | 9/1999 | Fogel |
| 5,972,328 A | 10/1999 | Kisilevsky et al. |
| 5,977,307 A | 11/1999 | Friden et al. |
| 5,989,592 A | 11/1999 | Collin |
| 6,004,936 A | 12/1999 | Kisilevsky |
| 6,015,555 A | 1/2000 | Friden |
| 6,015,835 A | 1/2000 | Miyamoto et al. |
| 6,024,977 A | 2/2000 | Yatvin et al. |
| 6,037,327 A | 3/2000 | Castillo et al. |
| 6,294,583 B1 | 9/2001 | Fogel |
| 6,306,909 B1 | 10/2001 | Weaver et al. |
| 6,310,073 B1 | 10/2001 | Kisilevsky et al. |
| 6,316,501 B1 | 11/2001 | Miyamoto et al. |
| 6,329,356 B1 | 12/2001 | Szarek et al. |
| 6,376,557 B1 | 4/2002 | Zaveri |
| 6,440,952 B2 | 8/2002 | Szarek et al. |
| 6,562,836 B1 * | 5/2003 | Szarek et al. ............... 514/307 |
| 6,670,399 B2 | 12/2003 | Green et al. |
| 6,930,112 B2 | 8/2005 | Weaver et al. |
| 7,153,692 B2 | 12/2006 | Campbell et al. |
| 7,244,764 B2 | 7/2007 | Kong et al. |
| 7,253,306 B2 | 8/2007 | Kong et al. |
| 7,262,223 B2 | 8/2007 | Kong et al. |
| 7,268,164 B2 | 9/2007 | Weaver et al. |
| 7,311,893 B2 | 12/2007 | Gervais et al. |
| 7,393,875 B2 | 7/2008 | Szarek et al. |
| 7,414,076 B2 | 8/2008 | Kong et al. |
| 2001/0048941 A1 | 12/2001 | Kisilevsky et al. |
| 2002/0022657 A1 | 2/2002 | Gervais et al. |
| 2002/0115717 A1 | 8/2002 | Gervais et al. |
| 2002/0193395 A1 | 12/2002 | Kisilevsky et al. |
| 2003/0027796 A1 | 2/2003 | Szarek et al. |
| 2003/0077833 A1 | 4/2003 | Campbell et al. |
| 2003/0108595 A1 | 6/2003 | Kisilevsky et al. |
| 2003/0114441 A1 | 6/2003 | Weaver et al. |
| 2003/0153584 A1 | 8/2003 | Weaver et al. |
| 2003/0194375 A1 | 10/2003 | Weaver et al. |
| 2004/0006092 A1 | 1/2004 | Chalifour et al. |
| 2004/0096453 A1 | 5/2004 | Kisilevsky et al. |
| 2004/0138178 A1 | 7/2004 | Szarek et al. |
| 2004/0208875 A1 | 10/2004 | Kisilevsky et al. |
| 2004/0220138 A1 | 11/2004 | Gervais et al. |
| 2005/0031651 A1 | 2/2005 | Gervais et al. |
| 2005/0038000 A1 | 2/2005 | Kong et al. |
| 2005/0142191 A1 | 6/2005 | Legore |
| 2005/0215562 A1 | 9/2005 | Tremblay et al. |
| 2006/0014752 A1 | 1/2006 | Weaver et al. |
| 2006/0116347 A1 | 6/2006 | Kisilevsky et al. |
| 2006/0135479 A1 | 6/2006 | Szarek et al. |
| 2006/0167057 A1 | 7/2006 | Kong et al. |
| 2006/0167095 A1 | 7/2006 | Kisilevsky et al. |
| 2006/0183800 A1 | 8/2006 | Kong et al. |
| 2006/0223855 A1 | 10/2006 | Kong et al. |
| 2006/0252829 A1 | 11/2006 | Garceau et al. |
| 2007/0010573 A1 | 1/2007 | Kong et al. |
| 2007/0015737 A1 | 1/2007 | Clark et al. |
| 2007/0021483 A1 | 1/2007 | Chalifour et al. |
| 2007/0078082 A1 | 4/2007 | Kisilevsky et al. |
| 2007/0265334 A1 | 11/2007 | Kisilevsky et al. |
| 2008/0004244 A1 | 1/2008 | Szarek et al. |
| 2008/0015180 A1 | 1/2008 | Kong et al. |
| 2008/0027097 A1 | 1/2008 | Kong et al. |
| 2008/0038192 A1 | 2/2008 | Gervais |

FOREIGN PATENT DOCUMENTS

| | | |
|---|---|---|
| CA | 2046037 | 1/1992 |
| DE | 927992 | 5/1955 |
| DE | 2140278 | 3/1972 |
| DE | 4004978 A1 | 8/1991 |
| DE | 4313118 A1 | 10/1994 |
| EP | 0003275 A1 | 8/1979 |
| EP | 0115657 B1 | 8/1984 |
| EP | 0236251 A2 | 9/1987 |
| EP | 0293974 B1 | 12/1988 |
| EP | 0309421 B1 | 3/1989 |
| EP | 0330353 B1 | 8/1989 |
| EP | 0387867 B1 | 9/1990 |
| EP | 0405834 A2 | 1/1991 |
| EP | 0434173 A2 | 6/1991 |
| EP | 0457295 B1 | 11/1991 |
| EP | 0464759 A2 | 1/1992 |
| EP | 0533352 A2 | 3/1993 |
| EP | 0797992 A2 | 10/1997 |
| FR | 2437834 | 6/1980 |
| JP | 1-151514 | 6/1989 |
| JP | 1-171638 | 7/1989 |
| JP | 2-78620 A | 3/1990 |
| JP | 2-149341 A | 6/1990 |
| JP | 3-83921 A | 4/1991 |
| JP | 5-17471 A | 1/1993 |
| WO | WO-85/02342 A1 | 6/1985 |
| WO | WO-88/09171 A1 | 12/1988 |
| WO | WO-89/05646 A1 | 6/1989 |
| WO | WO-89/11299 A1 | 11/1989 |
| WO | WO-90/09789 A2 | 9/1990 |
| WO | WO-91/04014 A1 | 4/1991 |
| WO | WO-91/04745 A1 | 4/1991 |
| WO | WO-91/14438 A1 | 10/1991 |
| WO | WO-92/02248 A1 | 2/1992 |
| WO | WO-92/14456 A1 | 9/1992 |
| WO | WO-93/10459 A1 | 5/1993 |
| WO | WO-93/11762 A1 | 6/1993 |
| WO | WO-93/24118 A1 | 12/1993 |
| WO | WO-94/00135 A1 | 1/1994 |
| WO | WO-94/01116 A1 | 1/1994 |
| WO | WO-94/01131 A1 | 1/1994 |
| WO | WO-94/02178 A1 | 2/1994 |
| WO | WO-94/03424 A1 | 2/1994 |
| WO | WO-94/06450 A1 | 3/1994 |
| WO | WO-94/22437 A2 | 10/1994 |
| WO | WO-94/27602 A1 | 12/1994 |
| WO | WO-95/01096 A1 | 1/1995 |
| WO | WO-95/06477 | 3/1995 |
| WO | WO-95/07092 A1 | 3/1995 |
| WO | WO-96/00537 A1 | 1/1996 |
| WO | WO-96/04001 A1 | 2/1996 |
| WO | WO-96/04915 A1 | 2/1996 |
| WO | WO-96/22303 A1 | 7/1996 |
| WO | WO-96/28187 A1 | 9/1996 |
| WO | WO-97/07402 A1 | 9/1996 |
| WO | WO-96/37612 A1 | 11/1996 |
| WO | WO-96/39129 A1 | 12/1996 |
| WO | WO-97/09445 A1 | 3/1997 |
| WO | WO-97/09976 | 3/1997 |
| WO | WO-97/14306 A1 | 4/1997 |
| WO | WO-97/16191 | 5/1997 |
| WO | WO-98/11923 A1 | 3/1998 |
| WO | WO-98/13046 | 4/1998 |

| | | |
|---|---|---|
| WO | WO-98/25938 | 6/1998 |
| WO | WO-99/06545 A2 | 2/1999 |
| WO | WO-99/08685 A1 | 2/1999 |
| WO | WO-99/38498 A1 | 8/1999 |
| WO | WO-99/40909 A1 | 8/1999 |
| WO | WO-00/06133 | 2/2000 |
| WO | WO-00/56328 A1 | 9/2000 |
| WO | WO-00/57707 | 10/2000 |
| WO | WO-00/64420 A2 | 11/2000 |
| WO | WO-00/71101 A2 | 11/2000 |
| WO | WO-01/03680 A2 | 1/2001 |
| WO | WO-01/52903 A1 | 7/2001 |
| WO | WO-04/113275 A2 | 12/2004 |

OTHER PUBLICATIONS

Beilstein Registry No. 7023352, N-(1'-aza-cyclopenten-2'yl)-2-aminoethane sulfonic acid, May 11, 1995: Campagna, Francesco et al, "Cyclic Amidine Analogues of Taurine and Homotaurine: Synthesis and Effects on Rat Skeletal Muscle," *II Farmaco*, vol. 49(10):653-658 (1994).
Beilstein Registry No. 8919306, Microxine, Jan. 24, 2002: Killday, K. Brian et al, "Microxine, a New cdc2 Kinase Inhibitor from the Australian Marine Sponge *Microxina* Species," *J. Nat. Prod.*, vol. 64:525-526 (2001).
Beilstein Registry No. 6023409, N,N-bis(2-sulfonylethyl)-1-octanamine disodium salt, Jul. 22, 1993: Tomson, R. et al, "Preparation and Properties of Surfactants of the Type of disodium Salts of N,N-BIS(2-Sulfoethyl)-1-Alkanamins," *Appl. Chem. USSR*, vol. 57(9):1885-1891 (1984).
Beilstein Registry No. 2272192, N-(2-Sulfo-ethyl)-benzamid, Jun. 29, 1989: Wood, J. Matthew et al, "Reactivity and the mechanisms of reactions of β-sultams with nucleophiles," *J. Chem. Soc.*, vol. 2:938-946 (2002).
Beilstein Registry No. 3948718, N-(Butyl-sulfonsaeure-(4))-DL-alanin, Mar. 19, 1991: Helferich, von Burckhardt et al, "Sultame von Aminosäuren," Liebigs Ann. Chem., vol. 651:33-42 (1962).
Beilstein Registry No. 1712477, 2-leucylamino-ethanesulfonic acid, Feb. 27, 1989: Abderhalden, Emil et al, "Weitere Studien über das Wesen von Ferment-wirkungen, ausgeführt mit Fermenten der Gruppe der Polypeptidasen," Fermentforschung, vol. 12:183-223 (1930).
Beilstein Registry No. 2972476, 3-Benzylamino-propan-1-sulfonsaeure, Jul. 11, 1989: Dorn, Helmut et al, "Cyanäthylierung und Sulfopropylierung von Phenyl-, Benzyl- und Cyclohexylhydrazin," Z. Chem., vol. 7:151-152 (1967).
Beilstein Registry No. 2434022, 4-Aethylamino-butansulfonsaeure-(1), Jul. 5, 1989: Helferich, von Burckhardt et al, "Alkylamino- und Arylaminoalkansulfonsäuren Sowie Arylaminobutansultame," Liebigs Ann. Chem., vol. 647:37-40 (1961).
Beilstein Registry No. 5620601, H-α-Glu-Ser-Tau-OH, Feb. 12, 1993: Ienaga, Kazuharu et al, "Simple Peptides. III. Syntheses and Properties of Taurine-Oligopeptides Containing an Acidic α-Amino Acid," Chem. Pharm. Bull., vol. 36(8):2796-2801 (1988).
Beilstein Registry No. 2846394, α-Naphthylaminomethylsulfonsaeure, 07/11/1989.
Beilstein Registry No. 3952462, 4-Azonia-6-phenyl-hexan-1-sulfonat, Mar. 19, 1991: Allen, C.F.H. et al, "Sultones as Reagents for Derivatizing Aliphatic Amines in Qualitative Organic Analysis," Anal. Chem., vol. 37:156-158 (1965).
Beilstein Registry No. 5568774, L-phenylalanyltaurine, Feb. 12, 1993: Ienaga, Kazuharu et al, "Simple Peptides. II. Syntheses and Properties of Taurine-Dipeptides Containing Neutral α-Amino Acid," Chem. Pharm. Bull., vol. 36(1):70-77 (1988).
Berge, Stephen M. et al, "Pharmaceutical Salts," Journal of Pharmaceutical Sciences, Vol. 66(1):1-19 (1977).
Bloemen, P.G.M. et al, "Adhesion molecules: a new target for immunoliposome-mediated drug delivery," FEBS, vol. 357:140-144 (1995).
Boismare, F. et al, "A Homotaurine Derivative Reduces the Voluntary Intake of Ethanol by Rats: are Cerebral GABA Receptors Involved?" Pharmacology Biochemistry & Behavior, vol. 21:787-789 (1984).

Briggs, Andrew D. et al, "Acyloxymethyl and 4-Acyloxybenzyl Diester Prodrugs of Phosphonoformate," Tetrahedron, vol. 52(47):14937-14950 (1996).
Brisco, Page et al, "Delivery of superoxide dismutase to pulmonary epithelium via pH-sensitive liposomes," Am. J. Physiol., vol. 268:L374-L380 (1995).
Brissette, Louise et al, "Differential Induction of the Serum Amyloid A Gene Family in Response to an Inflammatory Agent and to Amyloid-enhancing Factor," The Journal of Biological Chemistry, vol. 264(32):19327-19332 (1989).
Buée, L. et al, "Alzheimer's disease: binding of vascular and neuroblastoma heparan sulfate proteoglycans to amyloid β protein A4," Advances in the Biosciences, vol. 87:217-218 (1993).
Cai, Xiao-Dan et al, "Release of Excess Amyloid β Protein from a Mutant Amyloid β Protein Precursor," Science, vol. 259:514-516 (1993).
Campagna, Francesco et al, "Cyclic Amidine Analogues of Taurine and Homotaurine: Synthesis and Effects on Rat Skeletal Muscle," II Farmaco, vol. 49(10):653-658 (1994).
Caughey, Byron et al, "Sulfated Polyanion Inhibition of Scrapie-Associated PrP Accumulation in Cultured Cells," Journal of Virology, vol. 67(2):643-650 (1993).
Caughey, B., "Scrapie associated PrP accumulation and its prevention: insights from cell culture", British Medical Bulletin, vol. 49(4): 860-872 (1993).
Caughey, B., "Protease-resistant PrP accumulation and scrapie agent replication: a role for sulphated glycosaminoglycans?" Biochemical Society Transactions, 648th Meeting Belfast, vol. 22:163-167 (1994).
*Caughey, Byron, "Scrapie-associated PrP accumulation and agent replication: effects on s*ulphated glycosaminoglycan analogues," Phil. Trans. R. Soc. Lond. B., vol. 343:399-404 (1*994).
Caughey, Bryon et al, "Binding of the Protease-Sensitive Form of Prion Protein PrP to Sulfated Glycosaminoglycan and Congo Red," Journal of Virology, vol 68(4):2135-2141 (1994).
Chabenat, C. et al, "Physiochemical, Pharmacological and Pharmacokinetic Study of a New GABAergic Compound, Calcium Acetylhomotaurinate," Meth and Find Exptl Clin Pharmacol., vol. 10(5):311-317 (1988).
Chishti, M. Azhar et al, "Early-onset Amyloid Deposition and Cognitive Deficits in Transgenic Mice Expressing a Double Mutant Form of Amyloid Precursor Protein 695," The Journal of Biological Chemistry, vol. 276(24):21562-21570 (2001).
Colon, Wilfredo et al, "Partial Denaturation of Transthyretin is Sufficient for Amyloid Fibril Formation in Vitro," Biochemistry, vol. 31:8654-8660 (1992).
Copani, A. et al, "Activation of Metabotropic Glutamate Receptors Protects Cultured Neurons Against Apoptosis Induced by β-Amyloid Peptide," Molecular Pharmacology, vol. 47:890-897 (1995).
DeMattos, Ronald B. et al, "Brain to Plasma Amyloid-β Efflux: a Measure of Brain Amyloid Burden in a Mouse Model of Alzheimer's Disease," Science, vol. 295:2264-2267 (2002).
Dow, Kimberly, E. et al, "Effects of 4-deoxy-L-threo-pentose, a novel carbohydrate, on neural cell proteoglycan synthesis and function," Biochimica et Biophysica Acta, vol. 1156:7-14 (1992).
Durbin, PH et al, "Evidence of Acamprosate Penetration into the Rat Brain," Behavioural Pharmacology, vol. 6:620 (1995).
Ehlers, Bernhard et al, "Dextran Sulphate 500 Delays and Prevents Mouse Scrapie by Impairment of Agent Replication in Spleen," The Journal of General Virology, vol. 65:1325-1330 (1984).
Eisai America, Inc., "Aricept." Copyright 1995-1996, Center Watch, Inc. http://www.centerwatch.com/patient/drugs/dru190.html.
Fraser, Paul E. et al, "Effects of Sulfate Ions on Alzheimer β/A4 Peptide Assemblies: Implications for Amyloid Fibril-Proteoglycan Interactions," Journal of Neurochemistry, vol. 59:1531-1540 (1992).
Fraser, Paul E. et al, "Fibril Formation by Primate, Rodent, and Dutch-Hemorrhagic Analogues of Alzheimer Amyloid β-Protein," Biochemisty, vol. 31:10716-10723 (1992).
Fujii, Akira et al, "Probiotics. Antistaphylococcal and Antifibrinolytic Activities of ω-Amino- and ω-Guanidinoalkanesulfonic Acids," Journal of Medicinal Chemisty, vol. 18(5):502-505 (1975).

Gervais, Francine, "Amyloid—Those Deadly Fibrils," Eur. Biopharm. Review, pp. 40-42 (2001).
Gervais, Francine et al, "Proteoglycans and Amyloidogenic Proteins in Peripheral Amyloidosis," Curr. Med. Chem.—Immun., Endo. & Metab. Agents, vol. 3:361-370 (2003).
Girault, J. et al, "Determination of calcium acetylhomotaurinate in human plasma and urine by combined gas chromatography-negative-ion chemical ionization mass spectrometry," Journal of Chromatography, vol. 530(2):295-305 (1990).
Gorin, Boris I. et al, "A Novel Esterification Procedure Applied to Synthesis of Biologically Active Esters of Foscarnet," Tetrahedron, vol. 38(16):2791-2794 (1997).
Grant, K.A. et al, "Reinforcing and Discriminative Stimulus Effects of Ca-Acetyl Homotaurine in Animals," Pharmacology, Biochemistry & Behavior, vol. 32:607-611 (1989).
Hamazaki, Hideaki et al, "Calcium-dependent polymerization of human serum amyloid P component is inhibited by heparin and dextran sulfate," Biochimica et Biophysica Acta, vol. 998:231-235 (1989).
Hamazaki, Hideaki, "Ca2+-mediated Association of Human Serum Amyloid P Component with Heparan Sulfate and Dermatan Sulfate," The Journal of Biological Chemistry, vol. 262(4):1456-1460 (1987).
Hamilton, Ronald L., "Lewy Bodies in Alzheimer's Disease: A Neuropathological Review of 145 Cased Using α-Synuclein Immunohistochemistry," Brain Pathology, vol. 10:378-384 (2000).
Han, Hogyu et al, "The core Alzheimer's peptide NAC forms amyloid fibrils which seed and are seeded by β-amyloid: is NAC a common trigger or target in neurodegenerative disease?" Chemistry & Biology, vol. 2:163-169 (1995).
Hawkins, P.N., "Diagnosis and monitoring of amyloidosis," Bailliére's Clinical Rheumatology, vol. 8(3):635-659 (1994).
Hutchings, R. et al, "The Effect of Excitotoxin Antagonists on Ibotenic Acid-Induced Alteration of APP MRNA Hippocampal Expression," J. Pharmacy and Pharmacology, vol. 47(12B):1131 (1995).
Ismail, Ibrahim Imam, "Reactions with sultones II," Afinidad L., vol. 446:256-258 (1993).
Ismail, Ibrahim Imam, "Reactions with sultones and sultams," J. Serb. Chem. Soc., vol. 57(7):415-420 (1992).
Iwai, Akihiko, "Properties of NACP/α-synuclein and its role in Alzheimer's disease," Biochimica et Biophysica Acta, vol. 1502:95-109 (2000).
Iwai, Akihiko et al, "Non-A β Component of Alzheimer's Disease Amyloid (NAC) Is Amyloidogenic," Biochemistry, vol. 34:10139-10145 (1995).
James, Guy L. et al, "Benzodiazepine Peptidomimetics: Potent Inhibitors of Ras Farnesylation in Animal Cells," Science, vol. 260:1937-1942 (1993).
Kagan, D.Z. et al, "Congo Red Inhibition of Amylogenesis in Experimental Amyloidosis," Problemy Tuberkuleza, vol, 40:72-74.
Keinänen, Kari et al, "Biosynthetic lipid-tagging of antibodies," FEBS, vol. 346:123-126 (1994).
Killion, Jerald J. et al, "Systemic Targeting of Liposome-Encapsulated Immunomodulators to Macrophages for Treatment of Cancer Metastasis," Immunomethods, vol. 4:273-279 (1994).
Kisilevsky, R., "From arthritis to Alzheimer's disease; current concepts on the pathogenesis of amyloidosis," Can. J. Physiol. Pharmacol., vol. 65:1805-1818 (1987).
Kisilevsky, R. et al, "The Potential Significance of Sulphated Glycosaminoglycans as a Common Constituent of all Amyloids: or, Perhaps Amyloid is not a Misnomer," Medical Hypotheses, vol. 26:231-236 (1988).
Kisilevsky, Robert, "Theme and Variations on a String of Amyloid," Neurobiology of Aging, vol. 10:499-500 (1989).
Kisilevsky, Robert, "Heparan Sulfate Proteoglycans in Amyloidogenesis: An Epiphenomenon, A Unique Factor, or the Tip of a More Fundamental Process," Laboratory Investigation, vol. 63(5):589-591 (1990).
Kisilevsky, Robert, "A Critical Analysis of Postulated Pathogenetic Mechanisms in Amyloidogenesis," Critical Reviews in Clinical Laboratory Sciences, vol. 29(1):59-82 (1992).
Kisilevsky, Robert et al, "Arresting amyloidosis in vivo using small-molecule anionic sulphonates or sulphates: implications for Alzheimer's disease," Nature Medicine, vol. 1(2):143-148 (1995).
Krogsgaard-Larsen, P. et al, "Novel (Gamma-Aminobutyric Acid)A Agonists and Partial Agonists," FIDIA Research Foundation Symposium Series (1991).
Lacoste, Anne-Marie et al, "Inhibition of D-Alanyl-D-Alanine Ligase in Different Bacterial Species by Amino Phosphonic Acids," Current Microbiology, vol. 2:113-117 (1979).
Leveugle, B. et al, "Binding of heparan sulfate glycosaminoglycan to β-amyloid peptide: inhibition by potentially therapeutic polysulfated compounds," NeuroReport, vol. 5:1389-1392 (1994).
Lhuintre, Jean-Pierre et al, "Ability of Calcium Bis Acetyl Homotaurine, a Gaba Agonist, to Prevent RElapse in Weaned Alcoholics," The Lancet, vol. 1(8436):1014-1016 (1985).
Littleton, John, "Acamprosate in alcohol dependence: how does it work?" Addiction, vol. 90:1179-1188 (1995).
Lyon, A.W. et al, "Co-deposition of Basement Membrane Components during the Induction of Murine Splenic AA Amyloid," Laboratory Investigation, vol. 64(6):785-790 (1991).
Madamba, Samuel G. et al, "Acamprosate (Calcium Acetylhomotaurinate) Enhances the N-Methyl-D-Aspartate Component of Excitatory Neurotransmission in Rat Hippocampal CA1 Neurons in Vitro," Alcoholism: Clinical and Experimental Research, vol. 20(4):651-658 (1996).
Malmusi, Luca et al, "1,2,3,4-Tetrahydroisoquinoline and Related Analogs of the Phenylalkylamine Designer Drug MDMA," Med. Chem. Res., vol. 6(6):412-426 (1996).
Masliah, Eliezer et al, "Altered Presynaptic Protein NACP Is Associated with Plaque Formation and Neurodegeneration in Alzheimer's Disease," American Journal of Pathology, vol. 148(1):201-210 (1996).
Masuda, Midori et al, "Effect of taurine on nonspecific protection against bacterial infection," Database STN International, Chemical Abstracts Service, Accession No. 105:108004 (1985) (Abstract only).
May, Patrick C., "Current progress on new therapies for Alzheimer's disease," Drug Discovery Today, vol. 6(9):459-462 (2001).
McCubbin, William D. et al, "Circular-dichroism studies on two murine serum amyloid A proteins," Biochem. J., vol. 256:775-783 (1988).
The Merck Index, p. 883, Merck & Co. Inc., Rahway, N.J., USA (1989).
Mimura, Tetsutaro et al, "A Novel Class of Enkephalinase Inhibitors Containing a C-Terminal Sulfo Group," J. Med. Chem., vol. 35:602-608 (1992).
Morgan, Barry A. et al, "Approaches to the Discovery of Non-Peptide Ligands for Peptide Receptors and Peptidases," Ann. Rep. Med. Chem., Virick F.J. (Ed.) pp. 243-253, Academic Press, San Diego, CA (1989).
Mukaetova-Ladinska, E.B. et al, "α-Synuclein Inclusions in Alzheimer and Lewy Body Diseases," Journal of Neuropathology and Experimental Neurology, vol. 59(5):408-417 (2000).
Nakada, Tsutomu et al, "Guanidinoethane sulfate: brain pH alkaline shifter," NeuroReport, vol. 4:1035-1038 (1993).
Narindrasorasak, Suree et al, "Characterization of High Affinity Binding between Laminin and Alzheimer's Disease Amyloid Precursor Proteins," Laboratory Investigation, vol. 67(5):643-652 (1992).
Narindrasorasak, Suree et al, "High Affinity Interactions between the Alzheimer's β-Amyloid Precursor Proteins and the Basement Membrane Form of Heparan Sulfate Proteoglycan," The Journal of Biological Chemistry, vol. 266(20):12878-12883 (1991).
National Institute on Alcohol Abuse and Alcoholism No. 33 PH 366, Jul. 1996; "Alcohol Alerg," http://pubs.niaaa.nih.gov/publications/aa33.htm.
Norén, Jan O. et al, "Synthesis of Esters of Phosphonoformic Acid and Their Antiherpes Activity," Journal of Medicinal Chemistry, vol. 26(2):264-270 (1982).
O'Brien, Timothy D. et al, "Human Islet Amyloid Polypeptide Expression in COS-1 Cells," American Journal of Pathology, vol. 147(3):609-616 (1995).
Owais, Mohammad et al, "Chloroquine Encapsulated in Malaria-Infected Erythrocyte-Specific Antibody-Bearing Liposomes Effectively Controls Chloroquine-Resistant Plasmodium berghei Infections in Mice," Antimicrobial Agents and Chemotherapy, vol. 39(1):180-184 (1995).

Panula-Lehto, Elina et al, "Comparison of the Effects of Intraventricular Taurine, GABA and Homotaurine on Serum Prolactin Levels in Male Rats," Pharmacology and Toxicology, vol. 65:152-156 (1989).

Pollack, Scott J. et al, "Sulfonated dyes attenuate the toxic effects of β-amyloid in a structure-specific fashion," Neuroscience Letters, vol. 197:211-214 (1995).

Powell, D.S. et al, "Insulin and Polyionic Sulphonates Modify Human Islet Amyloid Polypeptide Fibril Aggregation In Vitro," Diabetologia, vol. 41(Suppl. 1):656 (1998).

Puchtler, H. et al, "Application of Thiazole Dye to Amyloid under Conditions of Direct Cotton Dyeing: Correlation of Histochemical and Chemical Data," Histochemistry, vol. 77:431-445 (1983).

Ranade, Vasant V., "Drug Delivery Systems. 1. Site-Specific Drug Delivery Using Liposomes as Carriers," J. Clin. Pharmacol., vol. 29:685-694 (1989).

Rodier, Par P. Toffoli et N. et al. "Bis(acétamido-3 propanesulfonate-1) de Calcium (N-Acétylhomotaurinate de Calcium)," Acta Cryst., vol. C44:1493-1494 (1988).

Sadler, Isobel I. J. et al, "Sulphated compounds attenuate β-amyloid toxicity by inhibiting its association with cells," NeuroReport, vol. 7:49-53 (1995).

St. Georgiev, Vassil et al, "Drug-Induced Modifications of the Immune Response. 1. Substituted 1-Phenylisoquinolines," Journal of Medicinal Chemistry, vol. 22(4):348-352 (1979).

Sass, Henning et al, "Relapse Prevention by Acamprosate," Arch. Gen. Psychiatry, vol. 53:673-680 (1996).

Schreier, Hans et al, "Targeting of Liposomes to Cells Expressing CD4 Using Glycosylphosphatidylinositol-anchored gp120," The Journal of Biological Chemistry, vol. 269(12):9090-9098 (1994).

Shue, Ho-Jane et al, "A Study of 3-Amino-N-Hydroxypropanesulfonamide Derivatives as Potential GABAB Agonists and Their Fragmentation to 3-Aminopropanesulfinic Acid," Bioorganic & Medicinal Chemistry Letters, vol. 6(14):1709-1714 (1996).

Silverman, Richard B., "Prodrugs and Drug Delivery Systems," The Organic Chemistry of Drug Design and Drug Action, Academic Press, Inc. Chapter 8, pp. 352-401.

Small, D.H. et al, "Association and Release of the Amyloid Protein Precursor of Alzheimer's Disease from Chick Brain Extracellular Matrix," The Journal of Neuroscience, vol. 12(11):4143-4150 (1992).

Snow, Alan D. et al, "Sulfated Glycosaminoglycans: A Common Constituent of All Amyloids?" Laboratory Investigation, vol. 56(1):120-123 (1987).

Snow, Alan D. et al, "Temporal Relationship between Glycosaminoglycan Accumulation and Amyloid Deposition during Experimental Amyloidosis," Laboratory Investigation, vol. 53(1):37-44 (1985).

Snow, Alan D. et al, "Sulfated Glycosaminoglycans in Alzheimer's Disease," Human Pathology, vol. 18(5):506-510 (1987).

Snow, Alan David et al, "Characterization of Tissue and Plasma Glycosaminoglycans during Experimental AA Amyloidosis and Acute Inflammation, Qualitative and Quantitative Analysis," Laboratory Investigation, vol. 56(6):665-675 (1987).

Snow, Alan David et al, "A Close Ultrastructural Relationship between Sulfated Proteoglycans and AA Amyloid Fibrils," Laboratory Investigation, vol. 57(6):687-698 (1987).

Snow, A. D. et al, "Sulfated glycosaminoglycans in amyloid plaques of prion diseases," Acta Neuropathol., vol. 77:337-342 (1989).

Snow, Alan D. et al, "A Temporal and Ultrastructural Relationship Between Heparan Sulfate Proteoglycans and AA Amyloid in Experimental Amyloidosis," The Journal of Histochemistry and Cytochemistry, vol. 39(10):1321-1330 (1991).

Stregan, G.H. et al, "Suppression of Chronic-Relapsing Experimental Allergic Encephalomyelitis in Strain-13 Guinea Pigs by Administration of Liposome-Associated Myelin Basic Protein," Journal of Neuroimmunolgy, vol. 7:27-41 (1984).

Tape, C. et al, "Direct Evidence for Circulating apoSAA as the Precursor of Tissue AA Amyloid Deposits," Scand. J. Immunol., vol. 28:317-324 (1988).

Travis, John, "New Piece of Alzheimer's Puzzle," Science, vol. 261:828-829 (1993).

Uéda, Kenji et al, "Molecular cloning of cDNA encoding an unrecognized component of amyloid in Alzheimer disease," Proc. Natl. Acad. Sci. USA, vol. 90:11282-11286 (1993).

Umezawa, F. et al, "Liposome Targeting to Mouse Brain: Mannose as a Recognition Marker," Biochemical and Biophysical Research Communications, vol. 153(3):1038-1044 (1988).

Westermark, P., Islet Pathology of Non-Insulin-dependent Diabetes Mellitus (NIDDM), Diabetic Medicine, vol. 13:S46-S48 (1996).

Whitworth, A. et al, "Is Acamprosate an Effective Treatment for Alcohol Dependence?" The Lancet, vol. 347:1438-1442 (1996).

Wong, S. et al, "Influence of Sulphate Ions on the Structure of AA Amyloid Fibrils," Scand. J. Immunol., vol. 32:225-232 (1990).

Wood, Stephen J. et al, "Selective Inhibition of Aβ Fibril Formation," The Journal of Biological Chemistry, vol. 271(8):4086-4092 (1996).

Yoshimoto, Makoto et al, "NACP, the precursor protein of the non-amyloid β/A4 protein (Aβ) component of Alzheimer disease amyloid, binds Aβ and stimulates Aβ aggregation," Proc. Natl. Acad. Sci. USA, vol. 92:9141-9145 (1995).

Young, I.D. et al, "The ultrastructural localization of sulfated proteoglycans is identical in the amyloids of Alzheimer's disease and AA, AL, senile cardiac and medullary carcinoma-associated amyloidosis," Acta Neuropathol., vol. 78:202-209 (1989).

Young, Iain D. et al, "Localization of the Basement Membrane Heparan Sulfate Proteoglycan in Islet Amyloid Deposits in Type II Diabetes Mellitus," Arch Pathol Lab Med., vol. 116:951-954 (1992).

EP 00202287.9 Communication mailed Jul. 24, 2002 including Partial European Search Report (8 pages).

EP 00202287.9 Communication mailed Feb. 11, 2003, including Partial European Search Report (15 pages).

International Search Report for Application No. PCT/IB2004/002337, dated Jul. 13, 2005.

Allen, C.F.H. et al., "Sultones as Reagents for Derivatizing Aliphatic Amines in Qualitative Organic Analysis," Analytical Chemistry, vol. 37(1):156-158 (1965).

CAplus 87:172883, Laboratoires Lucien, Compositions with combined analgesic, myorelaxing, anxiolytic adn antiinflammatory activity, (1997).

CAplus 138:12504, Smith, Jack V., "Method for assaying biomolecules and other constituents using indicator conjugates with synthetic nucleounits in lateral flow, liquid, and dry chemistry techniques," (2002).

Erman, William F. et al., "Syntheses and Facile Cleaveage of Five-Membered Ring Sultams," The Journal of Organic Chemistry, vol. 26(12):4841-4850 (1961).

Ismail, I. Imam et al., "Reactions with sultones," Afinidad, vol. 434:239-241 (1991).

Kametani, Tetsuji et al., "Syntheses of Homotaurine Related Compounds (Studies on the Syntheses of Heterocyclic Compounds Part CCCLV)," Pharmacometrics, vol. 4(4):713-720 (1970).

La Combe, Edward et al., "A New Reaction of Allylic Sulfones," Journal of the American Chemical Society, vol. 83(16):3457-3461 (1961).

Thiel, Teresa et al., "New zwitterionic butanesulfonic acids that extend the alkaline range of four families of good buffers: Evaluation for use in biological systems," J. Biochem. Biophys. Methods, vol. 37:1172-129 (1998).

Zeid, Ibrahim et al., "Synthese von N-substituirten Aminosulfonsäuren, II," Liebigs Ann. Chem., pp. 671-689 (1974).

Zeid, I.F. et al., "Synthesis of halogenated sultams II," Afinidad, vol. 434:252-254 (1991).

* cited by examiner

METHODS AND COMPOSITIONS FOR TREATING AMYLOID-RELATED DISEASES

RELATED APPLICATION

This application is a continuation of U.S. application Ser. No. 10/871,365, filed Jun. 18, 2004, currently pending, which claims priority to U.S. provisional patent application No. 60/480,906, filed Jun. 23, 2003 and U.S. provisional patent application No. 60/512,047, filed Oct. 17, 2003, expired. This application is also related to U.S. application Ser. No. 10/871,514, filed Jun. 18, 2004, currently pending.

The entire contents of each of these patent applications are hereby expressly incorporated herein by reference including without limitation the specification, claims, and abstract, as well as any figures, tables, or drawings thereof.

BACKGROUND

Amyloidosis refers to a pathological condition characterized by the presence of amyloid fibrils. Amyloid is a generic term referring to a group of diverse but specific protein deposits (intracellular or extracellular) which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common X-ray diffraction and infrared spectra.

Amyloid-related diseases can either be restricted to one organ or spread to several organs. The first instance is referred to as "localized amyloidosis" while the second is referred to as "systemic amyloidosis."

Some amyloid diseases can be idiopathic, but most of these diseases appear as a complication of a previously existing disorder. For example, primary amyloidosis (AL amyloid) can appear without any other pathology or can follow plasma cell dyscrasia or multiple myeloma.

Secondary amyloidosis is usually seen associated with chronic infection (such as tuberculosis) or chronic inflammation (such as rheumatoid arthritis). A familial form of secondary amyloidosis is also seen in other types of familial amyloidosis, e.g., Familial Mediterranean Fever (FMF). This familial type of amyloidosis is genetically inherited and is found in specific population groups. In both primary and secondary amyloidosis, deposits are found in several organs and are thus considered systemic amyloid diseases.

"Localized amyloidoses" are those that tend to involve a single organ system. Different amyloids are also characterized by the type of protein present in the deposit. For example, neurodegenerative diseases such as scrapie, bovine spongiform encephalitis, Creutzfeldt-Jakob disease, and the like are characterized by the appearance and accumulation of a protease-resistant form of a prion protein (referred to as AScr or PrP-27) in the central nervous system. Similarly, Alzheimer's disease, another neurodegenerative disorder, is characterized by neuritic plaques and neurofibrillary tangles. In this case, the amyloid plaques found in the parenchyma and the blood vessel is formed by the deposition of fibrillar Aβ amyloid protein. Other diseases such as adult-onset diabetes (type II diabetes) are characterized by the localized accumulation of amyloid fibrils in the pancreas.

Once these amyloids have formed, there is no known, widely accepted therapy or treatment which significantly dissolves amyloid deposits, in situ prevents further amyloid deposition or prevents the initiation of amyloid deposition.

Each amyloidogenic protein has the ability to undergo a conformational change and to organize into β-sheets and form insoluble fibrils which may be deposited extracellularly or intracellularly. Each amyloidogenic protein, although different in amino acid sequence, has the same property of forming fibrils and binding to other elements such as proteoglycan, amyloid P and complement component. Moreover, each amyloidogenic protein has amino acid sequences which, although different, show similarities such as regions with the ability to bind to the glycosaminoglycan (GAG) portion of proteoglycan (referred to as the GAG binding site) as well as other regions which promote α-sheet formation. Proteoglycans are macromolecules of various sizes and structures that are distributed almost everywhere in the body. They can be found in the intracellular compartment, on the surface of cells, and as part of the extracellular matrix. The basic structure of all proteoglycans is comprised of a core protein and at least one, but frequently more, polysaccharide chains (GAGs) attached to the core protein. Many different GAGs have been discovered including chondroitin sulfate, dermatan sulfate, keratan sulfate, heparin, and hyaluronan.

In specific cases, amyloid fibrils, once deposited, can become toxic to the surrounding cells. For example, the Aβ fibrils organized as senile plaques have been shown to be associated with dead neuronal cells, dystrophic neurites, astrocytosis, and microgliosis in patients with Alzheimer's disease. When tested in vitro, oligomeric (soluble) as well as fibrillar Aβ peptide was shown to be capable of triggering an activation process of microglia (brain macrophages), which would explain the presence of microgliosis and brain inflammation found in the brain of patients with Alzheimer's disease. Both oligomeric and fibrillar Aβ peptide can also induce neuronal cell death in vitro. See, e.g., M P Lambert, et al., *Proc. Natl. Acad. Sci. USA* 95, 6448-53 (1998).

In another type of amyloidosis seen in patients with type II diabetes, the amyloidogenic protein IAPP, when organized in oligomeric forms or in fibrils, has been shown to induce α-islet cell toxicity in vitro. Hence, appearance of IAPP fibrils in the pancreas of type II diabetic patients contributes to the loss of the β islet cells (Langerhans) and organ dysfunction which can lead to insulinemia.

Another type of amyloidosis is related to $\beta_2$ microglobulin and is found in long-term hemodialysis patients. Patients undergoing long term hemodialysis will develop $\beta_2$-microglobulin fibrils in the carpal tunnel and in the collagen rich tissues in several joints. This causes severe pains, joint stiffness and swelling.

Amyloidosis is also characteristic of Alzheimer's disease. Alzheimer's disease is a devastating disease of the brain that results in progressive memory loss leading to dementia, physical disability, and death over a relatively long period of time. With the aging populations in developed countries, the number of Alzheimer's patients is reaching epidemic proportions.

People suffering from Alzheimer's disease develop a progressive dementia in adulthood, accompanied by three main structural changes in the brain: diffuse loss of neurons in multiple parts of the brain; accumulation of intracellular protein deposits termed neurofibrillary tangles; and accumulation of extracellular protein deposits termed amyloid or senile plaques, surrounded by misshapen nerve terminals (dystrophic neurites) and activated microglia (microgliosis and astrocytosis). A main constituent of these amyloid plaques is the amyloid-β peptide (β), a 39-43 amino-acid protein that is produced through cleavage of the β-amyloid precursor protein (APP). Extensive research has been conducted on the relevance of Aβ deposits in Alzheimer's disease, see, e.g., Selkoe, *Trends in Cell Biology* 8, 447-453 (1998). Aβ naturally arises from the metabolic processing of the amyloid precursor protein ("APP") in the endoplasmic reticulum ("ER"), the Golgi apparatus, or the endosomal-lysosomal pathway, and most is normally secreted as a 40 ("Aβ1-40") or 42 ("Aβ1-42") amino acid peptide (Selkoe, *Annu. Rev. Cell Biol.* 10, 373-403 (1994)). A role for Aβ as a primary cause for Alzheimer's disease is supported by the presence of extracellular Aβ deposits in senile plaques of Alzheimer's disease, the increased production of Aβ in cells harboring mutant Alzheimer's disease associated genes, e.g., amyloid precursor protein, presenilin I and presenilin II; and the toxicity of extracellular soluble (oligomeric) or fibrillar Aβ to cells in culture. See, e.g., Gervais, *Eur. Biopharm. Review*, 40-42 (Autumn 2001); May, DDT6, 459-62 (2001). Although symptomatic treatments exist for Alzheimer's disease, this disease cannot be prevented or cured at this time.

Alzheimer's disease is characterized by diffuse and neuritic plaques, cerebral angiopathy, and neurofibrillary tangles. Plaque and blood vessel amyloid is believed to be formed by the deposition of insoluble Aβ amyloid protein, which may be described as diffuse or fibrillary. Both soluble oligomeric Aβ and fibrillar Aβ are also believed to be neurotoxic and inflammatory.

Another type of amyloidosis is cerebral amyloid angiopathy (CAA). CAA is the specific deposition of amyloid-β fibrils in the walls of leptomingeal and cortical arteries, arterioles and veins. It is commonly associated with Alzheimer's disease, Down's syndrome and normal aging, as well as with a variety of familial conditions related to stroke or dementia (see Frangione et al., Amyloid: J. Protein Folding Disord. 8, Suppl. 1, 36-42 (2001)).

Presently available therapies for treatment of β-amyloid diseases are almost entirely symptomatic, providing only temporary or partial clinical benefit. Although some pharmaceutical agents have been described that offer partial symptomatic relief, no comprehensive pharmacological therapy is currently available for the prevention or treatment of, for example, Alzheimer's disease.

SUMMARY OF THE INVENTION

The present invention relates to the use of certain compounds in the treatment of amyloid-related diseases. In particular, the invention relates to a method of treating or preventing an amyloid-related disease in a subject comprising administering to the subject a therapeutic amount of a compound of the invention. The invention also pertains to each of the novel compounds of the invention as described herein. Among the compounds for use in the invention are those according to the following Formulae, such that, when administered, amyloid fibril formation, organ specific dysfunction (e.g., neurodegeneration), or cellular toxicity is reduced or inhibited.

In one embodiment, the invention pertains, at least in part to compounds of Formula I:

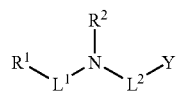

(I)

wherein:

$R^1$ is a substituted or unsubstituted cycloalkyl, heterocyclic, aryl, arylcycloalkyl, bicyclic or tricyclic ring, a bicyclic or tricyclic fused ring group, or a substituted or unsubstituted $C_2$-$C_{10}$ alkyl group;

$R^2$ is selected from a group consisting of hydrogen, alkyl, mercaptoalkyl, alkenyl, alkynyl, cycloalkyl, aryl, arylalkyl, thiazolyl, triazolyl, imidazolyl, benzothiazolyl, and benzoimidazolyl;

Y is $SO_3^-X^+$, $OSO_3^-X^+$, or $SSO_3^-X^+$;

$X^+$ is hydrogen, a cationic group, or an ester-forming group (i.e., as in a prodrug, which are described elsewhere herein); and each of $L^1$ and $L^2$ is independently a substituted or unsubstituted $C_1$-$C_5$ alkyl group or absent, or a pharmaceutically acceptable salt thereof, provided that when $R^1$ is alkyl, $L^1$ is absent.

In another embodiment, the invention pertains, at least in part to compounds of Formula II:

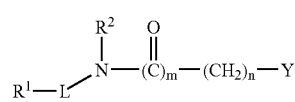

(II)

wherein:

$R^1$ is a substituted or unsubstituted cyclic, bicyclic, tricyclic, or benzoheterocyclic group or a substituted or unsubstituted $C_2$-$C_{10}$ alkyl group;

$R^2$ is hydrogen, alkyl, mercaptoalkyl, alkenyl, alkynyl, cycloalkyl, aryl, arylalkyl, thiazolyl, triazolyl, imidazolyl, benzothiazolyl, benzoimidazolyl, or linked to $R^1$ to form a heterocycle;

Y is $SO_3^-X^+$, $OSO_3^-X^+$, or $SSO_3^-X^+$;

$X^+$ is hydrogen, a cationic group, or an ester forming moiety;

m is 0 or 1;

n is 1, 2, 3, or 4;

L is substituted or unsubstituted $C_1$-$C_3$ alkyl group or absent, or a pharmaceutically acceptable salt thereof, provided that when $R^1$ is alkyl, L is absent.

In yet another embodiment, the invention pertains, at least in part to compounds of Formula III:

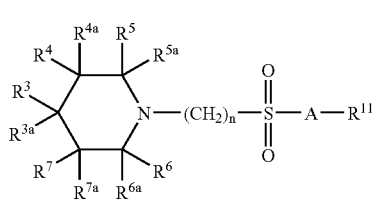

(III)

wherein:

A is nitrogen or oxygen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

$R^3$, $R^{3a}$, $R^4$, $R^{4a}$, $R^5$, $R^{5a}$, $R^6$, $R^{6a}$, $R^7$ and $R^{7a}$ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, or two R groups on adjacent ring atoms taken together with the ring atoms form a double bond, provided that one of $R^3$, $R^{3a}$, $R^4$, $R^{4a}$, $R^5$, $R^{5a}$, $R^6$, $R^{6a}$, $R^7$ and $R^{7a}$ is a moiety of Formula IIIa:

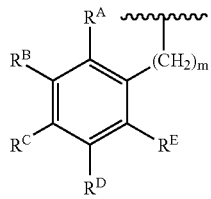

(IIIa)

wherein:
m is 0, 1, 2, 3, or 4;
$R^A$, $R^B$, $R^C$, $R^D$, and $R^E$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl; and pharmaceutically acceptable salts and esters thereof, provided that said compound is not 3-(4-phenyl-1,2,3,6-tetrahydro-1-pyridyl)-1-propanesulfonic acid.

In yet another embodiment, the invention pertains at least in part to compounds of Formula IV:

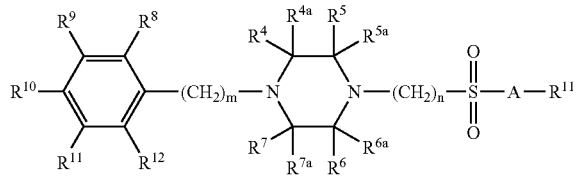

(IV)

wherein:
A is nitrogen or oxygen;
$R^{11}$ is hydrogen, salt-forming cation, ester forming group, —(CH$_2$)$_x$-Q, or when A is nitrogen, A and $R^{11}$ taken together may be the residue of a natural or unnatural amino acid or a salt or ester thereof;
Q is hydrogen, thiazolyl, triazolyl, imidazolyl, benzothiazolyl, or benzoimidazolyl;
x is 0, 1, 2, 3, or 4;
n is 0, 1, 2, 3, 4, 5, 6, 7, 8, 9, or 10;
$R^4$, $R^{4a}$, $R^5$, $R^{5a}$, $R^6$, $R^{6a}$, $R^7$, and $R^{7a}$ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, $R^4$ and $R^5$ taken together, with the ring atoms they are attached to, form a double bond, or $R^6$ and $R^7$ taken together, with the ring atoms they are attached to, form a double bond;
m is 0, 1, 2, 3, or 4;
$R^8$, $R^9$, $R^{10}$, $R^{11}$, and $R^{12}$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl, and pharmaceutically acceptable salts and esters thereof.

In another embodiment, the invention includes compounds of Formula V:

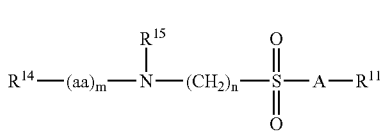

(V)

wherein:
A is nitrogen or oxygen;
$R^{11}$ is hydrogen, salt-forming cation, ester forming group, —(CH$_2$)$_x$-Q, or when A is nitrogen, A and $R^{11}$ taken together may be the residue of a natural or unnatural amino acid or a salt or ester thereof;
Q is hydrogen, thiazolyl, triazolyl, imidazolyl, benzothiazolyl, or benzoimidazolyl;
x is 0, 1, 2, 3, or 4;
n is 0, 1, 2, 3, 4, 5, 6, 7, 8, 9, or 10;
aa is a natural or unnatural amino acid residue;
m is 0, 1, 2, or 3;
$R^{14}$ is hydrogen or protecting group;
$R^{15}$ is hydrogen, alkyl or aryl, and pharmaceutically acceptable salts and prodrugs thereof.

In another embodiment, the invention includes compounds of the Formula VI:

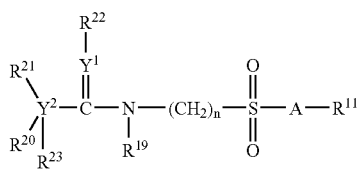

(VI)

wherein:
n is 1, 2, 3, 4, 5, 6, 7, 8, 9, or 10;
A is oxygen or nitrogen;
$R^{11}$ is hydrogen, salt-forming cation, ester forming group, —(CH$_2$)$_x$-Q, or when A is nitrogen, A and $R^{11}$ taken together may be the residue of a natural or unnatural amino acid or a salt or ester thereof;
Q is hydrogen, thiazolyl, triazolyl, imidazolyl, benzothiazolyl, or benzoimidazolyl;
x is 0, 1, 2, 3, or 4;
$R^{19}$ is hydrogen, alkyl or aryl;
$Y^1$ is oxygen, sulfur, or nitrogen;
$Y^2$ is carbon, nitrogen, or oxygen;
$R^{20}$ is hydrogen, alkyl, amino, mercaptoalkyl, alkenyl, alkynyl, cycloalkyl, aryl, arylalkyl, thiazolyl, triazolyl, tetrazolyl, imidazolyl, benzothiazolyl, or benzoimidazolyl;
$R^{21}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl, or absent if $Y^2$ is oxygen;
$R^{22}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl; or $R^{22}$ is hydrogen, hydroxyl, alkoxy or aryloxy if $Y^1$ is nitrogen; or $R^{22}$ is absent if $Y^1$ is oxygen or sulfur; or $R^{22}$ and $R^{21}$ may be linked to form a cyclic moiety if $Y^1$ is nitrogen;
$R^{23}$ is hydrogen, alkyl, amino, mercaptoalkyl, alkenyl, alkynyl, cycloalkyl, aryl, arylalkyl, thiazolyl, triazolyl, tetrazolyl, imidazolyl, benzothiazolyl, or benzoimidazolyl, or absent if $Y^2$ is nitrogen or oxygen;

or pharmaceutically acceptable salts thereof.

In one embodiment, the compounds disclosed herein prevent or inhibit amyloid protein assembly into insoluble fibrils which, in vivo, are deposited in various organs, or it favors clearance of pre-formed deposits or slows deposition in patients already having deposits. In another embodiment, the compound may also prevent the amyloid protein, in its soluble, oligomeric form or in its fibrillar form, from binding or adhering to a cell surface and causing cell damage or toxicity. In yet another embodiment, the compound may block amyloid-induced cellular toxicity or macrophage activation. In another embodiment, the compound may block amyloid-induced neurotoxicity or microglial activation. In another embodiment, the compound protects cells from amyloid induced cytotoxicity of B-islet cells. In another embodiment, the compound may enhance clearance from a specific organ, e.g., the brain or it decreases concentration of the amyloid protein in such a way that amyloid fibril formation is prevented in the targeted organ.

The compounds of the invention may be administered therapeutically or prophylactically to treat diseases associated with amyloid fibril formation, aggregation or deposition. The compounds of the invention may act to ameliorate the course of an amyloid related disease using any of the following mechanisms (this list is meant to be illustrative and not limiting): slowing the rate of amyloid fibril formation or deposition; lessening the degree of amyloid deposition; inhibiting, reducing, or preventing amyloid fibril formation; inhibiting neurodegeneration or cellular toxicity induced by amyloid; inhibiting amyloid induced inflammation; enhancing the clearance of amyloid; or favoring the degradation of amyloid protein prior to its organization in fibrils.

The compounds of the invention may be administered therapeutically or prophylactically to treat diseases associated with amyloid-β fibril formation, aggregation or deposition. The compounds of the invention may act to ameliorate the course of an amyloid-β related disease using any of the following mechanisms (this list is meant to be illustrative and not limiting): slowing the rate of amyloid-β fibril formation or deposition; lessening the degree of amyloid-β deposition; inhibiting, reducing, or preventing amyloid-β fibril formation; inhibiting neurodegeneration or cellular toxicity induced by amyloid-β; inhibiting amyloid-β induced inflammation; enhancing the clearance of amyloid-β from the brain; or favoring the degradation of amyloid-β protein prior to its organization in fibrils.

Therapeutic compounds of the invention may be effective in controlling amyloid-β deposition either following their entry into the brain (following penetration of the blood brain barrier) or from the periphery. When acting from the periphery, a compound may alter the equilibrium of Aβ between the brain and the plasma so as to favor the exit of Aβ from the brain. It may also increase the catabolism of neuronal Aβ and change the rate of exit from the brain. An increase in the exit of Aβ from the brain would result in a decrease in Aβ brain and cerebrospinal fluid (CSF) concentration and therefore favor a decrease in Aβ deposition. Alternatively, compounds that penetrate the brain could control deposition by acting directly on brain Aβ e.g., by maintaining it in a non-fibrillar form, favoring its clearance from the brain, or by slowing down APP processing. These compounds could also prevent Aβ in the brain from interacting with the cell surface and therefore prevent neurotoxicity, neurodegeneration or inflammation. They may also decrease Aβ production by activated microglia. The compounds may also increase degradation by macrophages or neuronal cells.

In one embodiment, the method is used to treat Alzheimer's disease (e.g., sporadic, familial, or early AD). The method can also be used prophylactically or therapeutically to treat other clinical occurrences of amyloid-β deposition, such as in Down's syndrome individuals and in patients with cerebral amyloid angiopathy ("CAA") or hereditary cerebral hemorrhage.

In another embodiment, the method is used to treat mild cognitive impairment. Mild Cognitive Impairment ("MCI") is a condition characterized by a state of mild but measurable impairment in thinking skills, which is not necessarily associated with the presence of dementia. MCI frequently, but not necessarily, precedes Alzheimer's disease.

Additionally, abnormal accumulation of APP and of amyloid-β protein in muscle fibers has been implicated in the pathology of sporadic inclusion body myositis (IBM) (Askanas, et al., Proc. Natl. Acad. Sci. USA 93, 1314-1319 (1996); Askanas, et al., Current Opinion in Rheumatology 7, 486-496 (1995)). Accordingly, the compounds of the invention can be used prophylactically or therapeutically in the treatment of disorders in which amyloid-beta protein is abnormally deposited at non-neurological locations, such as treatment of IBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration (AMD). AMD is a cause of irreversible vision loss in older individuals. It is believed that Aβ deposition could be an important component of the local inflammatory events that contribute to atrophy of the retinal pigmented epithelium, drusen biogenesis, and the pathogenesis of AMD (Johnson, et al., Proc. Natl. Acad. Sci. USA 99(18), 11830-5 (2002)).

The present invention therefore relates to the use of compounds of Formulae I, II, III, IV, V, VI, or otherwise described herein in the prevention or treatment of amyloid-related diseases, including, inter alia, Alzheimer's disease, cerebral amyloid angiopathy, mild cognitive impairment, inclusion body myositis, Down's syndrome, macular degeneration, as well as other types of amyloidosis like IAPP-related amyloidosis (e.g., diabetes), primary (AL) amyloidosis, secondary (AA) amyloidosis and β₂ microglobulin-related (dialysis-related) amyloidosis.

In Type II diabetes related amyloidosis (IAPP), the amyloidogenic protein IAPP induces β-islet cell toxicity when organized in oligomeric forms or in fibrils. Hence, appearance of IAPP fibrils in the pancreas of type II diabetic patients contributes to the loss of the β islet cells (Langerhans) and organ dysfunction which leads to insulinemia.

Primary amyloidosis (AL amyloid) is usually found associated with plasma cell dyscrasia and multiple myeloma. It can also be found as an idiopathic disease.

Secondary (AA) amyloidosis is usually seen associated with chronic infection (such as tuberculosis) or chronic inflammation (such as rheumatoid arthritis). A familial form of secondary amyloidosis is also seen in Familial Mediterranean Fever (FMF).

β₂ microglobulin-related (dialysis-related) amyloidosis is found in long-term hemodialysis patients. Patients undergoing long term hemodialysis will develop β₂-microglobulin fibrils in the carpal tunnel and in the collagen rich tissues in several joints. This causes severe pains, joint stiffness and swelling. These deposits are due to the inability to maintain low levels of β₂M in plasma of dialyzed patients. Increased plasma concentrations of $\beta_2$M protein will induce structural changes and may lead to the deposition of modified $\beta_2$M as insoluble fibrils in the joints.

DETAILED DESCRIPTION OF THE INVENTION

The present invention relates to the use of compounds of Formulae I, II, III, IV, V, VI, or compounds otherwise described herein in the treatment of amyloid-related diseases. For convenience, some definitions of terms referred to herein are set forth below.

Amyloid-Related Diseases

AA (Reactive) Amyloidosis

Generally, AA amyloidosis is a manifestation of a number of diseases that provoke a sustained acute phase response. Such diseases include chronic inflammatory disorders, chronic local or systemic microbial infections, and malignant neoplasms. The most common form of reactive or secondary (AA) amyloidosis is seen as the result of long-standing inflammatory conditions. For example, patients with Rheumatoid Arthritis or Familial Mediterranean Fever (which is a genetic disease) can develop AA amyloidosis. The terms "AA amyloidosis" and "secondary (AA) amyloidosis" are used interchangeably.

AA fibrils are generally composed of 8,000 Dalton fragments (AA peptide or protein) formed by proteolytic cleavage of serum amyloid A protein (ApoSAA), a circulating apolipoprotein which is mainly synthesized in hepatocytes in response to such cytokines as IL-1, IL-6 and TNF. Once secreted, ApoSAA is complexed with HDL. Deposition of AA fibrils can be widespread in the body, with a preference for parenchymal organs. The kidneys are usually a deposition site, and the liver and the spleen may also be affected. Deposition is also seen in the heart, gastrointestinal tract, and the skin.

Underlying diseases which can lead to the development of AA amyloidosis include, but are not limited to inflammatory diseases, such as rheumatoid arthritis, juvenile chronic arthritis, ankylosing spondylitis, psoriasis, psoriatic arthropathy, Reiter's syndrome, Adult Still's disease, Behcet's syndrome, and Crohn's disease. AA deposits are also produced as a result of chronic microbial infections, such as leprosy, tuberculosis, bronchiectasis, decubitus ulcers, chronic pyelonephritis, osteomyelitis, and Whipple's disease. Certain malignant neoplasms can also result in AA fibril amyloid deposits. These include such conditions as Hodgkin's lymphoma, renal carcinoma, carcinomas of gut, lung and urogenital tract, basal cell carcinoma, and hairy cell leukemia. Other underlying conditions that may be associated with AA amyloidosis are Castleman's disease and Schnitzler's syndrome.

AL Amyloidoses (Primary Amyloidosis)

AL amyloid deposition is generally associated with almost any dyscrasia of the B lymphocyte lineage, ranging from malignancy of plasma cells (multiple myeloma) to benign monoclonal gammopathy. At times, the presence of amyloid deposits may be a primary indicator of the underlying dyscrasia. AL amyloidosis is also described in detail in *Current Drug Targets*, 2004, 5 159-171.

Fibrils of AL amyloid deposits are composed of monoclonal immunoglobulin light chains or fragments thereof. More specifically, the fragments are derived from the N-terminal region of the light chain (kappa or lambda) and contain all or part of the variable ($V_L$) domain thereof. Deposits generally occur in the mesenchymal tissues, causing peripheral and autonomic neuropathy, carpal tunnel syndrome, macroglossia, restrictive cardiomyopathy, arthropathy of large joints, immune dyscrasias, myelomas, as well as occult dyscrasias. However, it should be noted that almost any tissue, particularly visceral organs such as the kidney, liver, spleen and heart, may be involved.

Hereditary Systemic Amyloidoses

There are many forms of hereditary systemic amyloidoses. Although they are relatively rare conditions, adult onset of symptoms and their inheritance patterns (usually autosomal dominant) lead to persistence of such disorders in the general population. Generally, the syndromes are attributable to point mutations in the precursor protein leading to production of variant amyloidogenic peptides or proteins. Table 1 summarizes the fibril composition of exemplary forms of these disorders.

TABLE 1

Fibril Composition of Exemplary Amyloid-Related Diseases

| Fibril Peptide/Protein | Genetic Variant | Clinical Syndrome |
|---|---|---|
| ATTR protein from Transthyretin and fragments | Met30, many others | Familial amyloid polyneuropathy (FAP), (Mainly peripheral nerves) |
| ATTR protein from Transthyretin and fragments | Thr45, Ala60, Ser84, Met111, Ile122 | Cardiac involvement predominant without neuropathy, familial amyloid polyneuropathy, senile systemic amyloidosis, Tenosynovium |
| N-terminal fragment of Apolipoprotein A1 (apoAI) | Arg26 | Familial amyloid polyneuropathy (FAP), (mainly peripheral nerves) |
| N-terminal fragment of Apoliproprotein A1 (AapoAI) | Arg26, Arg50, Arg 60, others | Ostertag-type, non-neuropathic (predominantly visceral involvement) |
| AapoAII from Apolipoprotein AII | | Familial amyloidosis |
| Lysozyme (Alys) | Thr56, His67 | Ostertag-type, non-neuropathic (predominantly visceral involvement) |
| Fibrogen alpha chain fragment | Leu554, Val526 | Cranial neuropathy with lattice corneal dystrophy |
| Gelsolin fragment (Agel) | Asn187, Tyr187 | Cranial neuropathy with lattice corneal dystrophy |
| Cystatin C fragment (ACys) | Glu68 | Hereditary cerebral hemorrhage (cerebral amyloid angiopathy) - Icelandic type |
| β-amyloid protein (Aβ) derived from Amyloid Precursor Protein (APP) | Gln693 | Hereditary cerebral hemorrhage (cerebral amyloid angiopathy) - Dutch type |
| β-amyloid protein (Aβ) derived from Amyloid Precursor Protein (APP) | Ile717, Phe717, Gly717 | Familial Alzheimer's Disease |
| β-amyloid protein (Aβ) derived from | Gln 618 | Alzheimer's disease, Down's syndrome, |

TABLE 1-continued

Fibril Composition of Exemplary Amyloid-Related Diseases

| Fibril Peptide/Protein | Genetic Variant | Clinical Syndrome |
|---|---|---|
| Amyloid Precursor Protein (APP), e.g., bPP 695 | | hereditary cerebral hemorrhage with amyloidosis, Dutch type |
| β-amyloid protein (Aβ) derived from Amyloid Precursor Protein (APP) | Asn670, Leu671 | Familial Dementia - probably Alzheimer's Disease |
| Prion Protein (PrP, APrP$^{SC}$) derived from Prp precursor protein (51-91 insert) | Leu102, Val167, Asn178, Lys200 | Familial Creutzfeldt-Jakob disease; Gerstmann-Sträussler-Scheinker syndrome (hereditary spongiform encephalopathies, prion diseases) |
| AA derived from Serum amyloid A protein (ApoSAA) | | Familial Mediterranean fever, predominant renal involvement (autosomal recessive) |
| AA derived from Serum amyloid A protein (ApoSAA) | | Muckle-Well's syndrome, nephropathy, deafness, urticaria, limb pain |
| Unknown | | Cardiomyopathy with persistent atrial standstill |
| Unknown | | Cutaneous deposits (bullous, papular, pustulodermal) |
| AH amyloid protein, derived from immunoglobulin heavy chain (gamma I) | AγI | Myeloma associated amyloidosis |
| ACal amyloid protein from (pro)calcitonin | (Pro) calcitonin | Medullary carcinomas of the thyroid |
| AANF amyloid protein from atrial natriuretic factor | | Isolated atrial amyloid |
| Apro from Prolactin | | Prolactinomas |
| Abri/ADan from ABri peptide | | British and Danish familial Dementia |

Data derived from Tan SY, Pepys MB. Amyloidosis. Histopathology, 25(5), 403-414 (November 1994), WHO/IUIS Nomenclature Subcommittee, Nomenclature of Amyloid and Amyloidosis. Bulletin of the World Health Organisation 1993; 71: 10508; and Merlini et al., Clin Chem Lab Med 2001; 39(11): 1065-75.

The data provided in Table 1 are exemplary and are not intended to limit the scope of the invention. For example, more than 40 separate point mutations in the transthyretin gene have been described, all of which give rise to clinically similar forms of familial amyloid polyneuropathy.

In general, any hereditary amyloid disorder can also occur sporadically, and both hereditary and sporadic forms of a disease present with the same characteristics with regard to amyloid. For example, the most prevalent form of secondary AA amyloidosis occurs sporadically, e.g. as a result of ongoing inflammation, and is not associated with Familial Mediterranean Fever. Thus general discussion relating to hereditary amyloid disorders below can also be applied to sporadic amyloidoses.

Transthyretin (TTR) is a 14 kiloDalton protein that is also sometimes referred to as prealbumin. It is produced by the liver and choroid plexus, and it functions in transporting thyroid hormones and vitamin A. At least 50 variant forms of the protein, each characterized by a single amino acid change, are responsible for various forms of familial amyloid polyneuropathy. For example, substitution of proline for leucine at position 55 results in a particularly progressive form of neuropathy; substitution of methionine for leucine at position 111 resulted in a severe cardiopathy in Danish patients.

Amyloid deposits isolated from heart tissue of patients with systemic amyloidosis have revealed that the deposits are composed of a heterogeneous mixture of TTR and fragments thereof, collectively referred to as ATTR, the full length sequences of which have been characterized. ATTR fibril components can be extracted from such plaques and their structure and sequence determined according to the methods known in the art (e.g., Gustavsson, A., et al., Laboratory Invest. 73: 703-708, 1995; Kametani, F., et al., Biochem. Biophys. Res. Commun. 125: 622-628, 1984; Pras, M., et al., PNAS 80: 539-42, 1983).

Persons having point mutations in the molecule apolipoprotein Al (e.g., Gly→Arg26; Trp→Arg50; Leu→Arg60) exhibit a form of amyloidosis ("Östertag type") characterized by deposits of the protein apolipoprotein AI or fragments thereof (AApoAI). These patients have low levels of high density lipoprotein (HDL) and present with a peripheral neuropathy or renal failure.

A mutation in the alpha chain of the enzyme lysozyme (e.g., Ile→Thr56 or Asp→His57) is the basis of another form of Östertag-type non-neuropathic hereditary amyloid reported in English families. Here, fibrils of the mutant lysozyme protein (Alys) are deposited, and patients generally exhibit impaired renal function. This protein, unlike most of the fibril-forming proteins described herein, is usually present in whole (unfragmented) form (Benson, M. D., et al. CIBA Fdn. Symp. 199: 104-131, 1996).

Immunoglobulin light chains tend to form aggregates in various morphologies, including fibrillar (e.g., AL amyloidosis and AH amyloidosis), granular (e.g., light chain deposition disease (LCDD), heavy chain deposition disease (HCDD), and light-heavy chain deposition disease (LH-CDD)), crystalline (e.g., Acquired Farconi's Syndrome), and microtubular (e.g., Cryoglobulinemia). AL and AH amyloidosis is indicated by the formation of insoluble fibrils of immunoglobulin light chains and heavy chain, respectively, and/or their fragments. In AL fibrils, lambda (λ) chains such as λ VI chains (λ6 chains), are found in greater concentrations than kappa (κ) chains. λIII chains are also slightly elevated. Merlini et al., CLIN CHEM LAB MED 39(11):1065-75 (2001). Heavy chain amyloidosis (AH) is generally characterized by aggregates of gamma chain amyloid proteins of the IgG1 subclass. Eulitz et al., PROC NATL ACAD SCI USA 87:6542-46 (1990).

Comparison of amyloidogenic to non-amyloidogenic light chains has revealed that the former can include replacements or substitutions that appear to destabilize the folding of the protein and promote aggregation. AL and LCDD have been distinguished from other amyloid diseases due to their relatively small population monoclonal light chains, which are manufactured by neoplastic expansion of an antibody-producing B cell. AL aggregates typically are well-ordered fibrils of lambda chains. LCDD aggregates are relatively amorphous aggregations of both kappa and lambda chains, with a majority being kappa, in some cases κIV. Bellotti et al., JOURNAL OF STRUCTURAL BIOLOGY 13:280-89 (2000). Comparison of amyloidogenic and non-amyloidogenic heavy chains in patients having AH amyloidosis has revealed missing and/or altered components. Eulitz et al., PROC NATL ACAD SCI USA 87:6542-46 (1990) (pathogenic heavy chain characterized by significantly lower molecular mass than non-amyloidogenic heavy chains); and Solomon et al. AM J HEMAT 45(2) 171-6 (1994) (amyloidogenic heavy chain characterized as consisting solely of the VH-D portion of the non-amyloidogenic heavy chain).

Accordingly, potential methods of detecting and monitoring treatment of subjects having or at risk of having AL, LCDD, AH, and the like, include but are not limited to immunoassaying plasma or urine for the presence or depressed deposition of amyloidogenic light or heavy chains, e.g., amyloid λ, amyloid κ, amyloid κIV, amyloid γ, or amyloid γ1.

Brain Amyloidosis

The most frequent type of amyloid in the brain is composed primarily of Aβ peptide fibrils, resulting in dementia associated with sporadic (non-hereditary) Alzheimer's disease. In fact, the incidence of sporadic Alzheimer's disease greatly exceeds forms shown to be hereditary. Nevertheless, fibril peptides forming plaques are very similar in both types. Brain amyloidosis includes those diseases, conditions, pathologies, and other abnormalities of the structure or function of the brain, including components thereof, in which the causative agent is amyloid. The area of the brain affected in an amyloid-related disease may be the stroma including the vasculature or the parenchyma including functional or anatomical regions, or neurons themselves. A subject need not have received a definitive diagnosis of a specifically recognized amyloid-related disease. The term "amyloid related disease" includes brain amyloidosis.

Amyloid-β peptide ("Aβ") is a 39-43 amino acid peptide derived by proteolysis from a large protein known as Beta Amyloid Precursor Protein ("βAPP"). Mutations in βAPP result in familial forms of Alzheimer's disease, Down's syndrome, cerebral amyloid angiopathy, and senile dementia, characterized by cerebral deposition of plaques composed of Aβ fibrils and other components, which are described in further detail below. Known mutations in APP associated with Alzheimer's disease occur proximate to the cleavage sites of β or γ-secretase, or within Aβ. For example, position 717 is proximate to the site of gamma-secretase cleavage of APP in its processing to Aβ, and positions 670/671 are proximate to the site of β-secretase cleavage. Mutations at any of these residues may result in Alzheimer's disease, presumably by causing an increase in the amount of the 42/43 amino acid form of Aβ generated from APP. The familial form of Alzheimer's disease represents only 10% of the subject population. Most occurrences of Alzheimer's disease are sporadic cases where APP and Aβ do not possess any mutation. The structure and sequence of Aβ peptides of various lengths are well known in the art. Such peptides can be made according to methods known in the art, or extracted from the brain according to known methods (e.g., Glenner and Wong, Biochem. Biophys. Res. Comm. 129, 885-90 (1984); Glenner and Wong, Biochem. Biophys. Res. Comm. 122, 1131-35 (1984)). In addition, various forms of the peptides are commercially available. APP is expressed and constitutively catabolized in most cells. The dominant catabolic pathway appears to be cleavage of APP within the Aβ sequence by an enzyme provisionally termed α-secretase, leading to release of a soluble ectodomain fragment known as APPsα. This cleavage precludes the formation of Aβ peptide. In contrast to this non-amyloidogenic pathway, APP can also be cleaved by enzymes known as β- and γ-secretase at the N- and C-termini of the Aβ, respectively, followed by release of Aβ into the extracellular space. To date, BACE has been identified as β-secretase (Vasser, et al., Science 286:735-741, 1999) and presenilins have been implicated in γ-secretase activity (De Strooper, et al., Nature 391, 387-90 (1998)). The 39-43 amino acid Aβ peptide is produced by sequential proteolytic cleavage of the amyloid precursor protein (APP) by the β and γ secretases enzyme. Although Aβ40 is the predominant form produced, 5-7% of total Aβ exists as Aβ42 (Cappai et al., Int. J. Biochem. Cell Biol. 31. 885-89 (1999)).

The length of the Aβ peptide appears to dramatically alter its biochemical/biophysical properties. Specifically, the additional two amino acids at the C-terminus of Aβ42 are very hydrophobic, presumably increasing the propensity of Aβ42 to aggregate. For example, Jarrett, et al. demonstrated that Aβ42 aggregates very rapidly in vitro compared to Aβ40, suggesting that the longer forms of Aβ may be the important pathological proteins that are involved in the initial seeding of the neuritic plaques in Alzheimer's disease (Jarrett, et al., Biochemistry 32, 4693-97 (1993); Jarrett, et al., Ann. N.Y. Acad. Sci. 695, 144-48 (1993)). This hypothesis has been further substantiated by the recent analysis of the contributions of specific forms of Aβ in cases of genetic familial forms of Alzheimer's disease ("FAD"). For example, the "London" mutant form of APP (APPV717I) linked to FAD selectively increases the production of Aβ 42/43 forms versus Aβ 40 (Suzuki, et al., Science 264, 1336-40 (1994)) while the "Swedish" mutant form of APP (APPK670N/M671L) increases levels of both Aβ40 and Aβ42/43 (Citron, et al., Nature 360, 672-674 (1992); Cai, et al., Science 259, 514-16, (1993)). Also, it has been observed that FAD-linked mutations in the Presenilin-1 ("PS1") or Presenilin-2 ("PS2") genes will lead to a selective increase in Aβ42/43 production but not Aβ40 (Borchelt, et al., Neuron 17, 1005-13 (1996)). This finding was corroborated in transgenic mouse models expressing PS mutants that demonstrate a selective increase in brain Aβ42 (Borchelt, op cit.; Duff, et al., Neurodegeneration 5(4), 293-98 (1996)). Thus the leading hypothesis regarding the etiology of Alzheimer's disease is that an increase in Aβ42 brain concentration due to an increased production and release of Aβ42 or a decrease in clearance (degradation or brain clearance) is a causative event in the disease pathology.

Multiple mutation sites in either Aβ or the APP gene have been identified and are clinically associated with either dementia or cerebral hemorrhage. Exemplary CAA disorders include, but are not limited to, hereditary cerebral hemorrhage with amyloidosis of Icelandic type (HCHWA-I); the Dutch variant of HCHWA (HCHWA-D; a mutation in Aβ); the Flemish mutation of Aβ; the Arctic mutation of Aβ; the Italian mutation of Aβ; the Iowa mutation of Aβ; familial British dementia; and familial Danish dementia. CAA may also be sporadic.

As used herein, the terms "β amyloid," "amyloid-β," and the like refer to amyloid β proteins or peptides, amyloid β precursor proteins or peptides, intermediates, and modifications and fragments thereof, unless otherwise specifically indicated. In particular, "Aβ" refers to any peptide produced by proteolytic processing of the APP gene product, especially peptides which are associated with amyloid pathologies, including Aβ1-39, Aβ1-40, Aβ1-41, Aβ1-42, and Aβ1-43.

For convenience of nomenclature, "Aβ1-42" may be referred to herein as "Aβ(1-42)" or simply as "Aβ42" or "Aβ$_{42}$" (and likewise for any other amyloid peptides discussed herein). As used herein, the terms "β amyloid," "amyloid-β" and "Aβ" are synonymous.

Unless otherwise specified, the term "amyloid" refers to amyloidogenic proteins, peptides, or fragments thereof which can be soluble (e.g., monomeric or oligomeric) or insoluble (e.g., having fibrillary structure or in amyloid plaque). See, e.g., MP Lambert, et al., *Proc. Nat'l Acad. Sci. USA* 95, 6448-53 (1998). "Amyloidosis" or "amyloid disease" or "amyloid-related disease" refers to a pathological condition characterized by the presence of amyloid fibers. "Amyloid" is a generic term referring to a group of diverse but specific protein deposits (intracellular or extracellular) which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common X-ray diffraction and infrared spectra.

Gelsolin is a calcium binding protein that binds to fragments and actin filaments. Mutations at position 187 (e.g., Asp→Asn; Asp→Tyr) of the protein result in a form of hereditary systemic amyloidosis, usually found in patients from Finland, as well as persons of Dutch or Japanese origin. In afflicted individuals, fibrils formed from gelsolin fragments (Agel), usually consist of amino acids 173-243 (68 kDa carboxyterminal fragment) and are deposited in blood vessels and basement membranes, resulting in corneal dystrophy and cranial neuropathy which progresses to peripheral neuropathy, dystrophic skin changes and deposition in other organs. (Kangas, H., et al. Human Mol. Genet. 5(9): 1237-1243, 1996).

Other mutated proteins, such as mutant alpha chain of fibrinogen (AfibA) and mutant cystatin C (Acys) also form fibrils and produce characteristic hereditary disorders. AfibA fibrils form deposits characteristic of a nonneuropathic hereditary amyloid with renal disease; Acys deposits are characteristic of a hereditary cerebral amyloid angiopathy reported in Iceland (Isselbacher, Harrison's Principles of Internal Medicine, McGraw-Hill, San Francisco, 1995; Benson, et al.). In at least some cases, patients with cerebral amyloid angiopathy (CAA) have been shown to have amyloid fibrils containing a non-mutant form of cystatin C in conjunction with amyloid beta protein (Nagai, A., et al. Molec. Chem. Neuropathol. 33: 63-78, 1998).

Certain forms of prion disease are now considered to be heritable, accounting for up to 15% of cases, which were previously thought to be predominantly infectious in nature. (Baldwin, et al., in Research Advances in *Alzheimer's Disease and Related Disorders*, John Wiley and Sons, New York, 1995). In hereditary and sporadic prion disorders, patients develop plaques composed of abnormal isoforms of the normal prion protein (PrP$^{Sc}$).

A predominant mutant isoform, PrP$^{Sc}$, also referred to as AScr, differs from the normal cellular protein in its resistance to protease degradation, insolubility after detergent extraction, deposition in secondary lysosomes, post-translational synthesis, and high β-pleated sheet content. Genetic linkage has been established for at least five mutations resulting in Creutzfeldt-Jacob disease (CJD), Gerstmann-Sträussler-Scheinker syndrome (GSS), and fatal familial insomnia (FFI). (Baldwin, supra) Methods for extracting fibril peptides from scrapie fibrils, determining sequences and making such peptides are known in the art (e.g., Beekes, M., et al. J. Gen. Virol. 76: 2567-76, 1995).

For example, one form of GSS has been linked to a PrP mutation at codon 102, while telencephalic GSS segregates with a mutation at codon 117. Mutations at codons 198 and 217 result in a form of GSS in which neuritic plaques characteristic of Alzheimer's disease contain PrP instead of Aβ peptide. Certain forms of familial CJD have been associated with mutations at codons 200 and 210; mutations at codons 129 and 178 have been found in both familial CJD and FFI. (Baldwin, supra).

Cerebral Amyloidosis

Local deposition of amyloid is common in the brain, particularly in elderly individuals. The most frequent type of amyloid in the brain is composed primarily of Aβ peptide fibrils, resulting in dementia or sporadic (non-hereditary) Alzheimer's disease. The most common occurrences of cerebral amyloidosis are sporadic and not familial. For example, the incidence of sporadic Alzheimer's disease and sporadic CAA greatly exceeds the incidence of familial Aβ and CAA. Moreover, sporadic and familial forms of the disease cannot be distinguished from each other (they differ only in the presence or absence of an inherited genetic mutation); for example, the clinical symptoms and the amyloid plaques formed in both sporadic and familial Aβ are very similar, if not identical.

Cerebral amyloid angiopathy (CAA) refers to the specific deposition of amyloid fibrils in the walls of leptomingeal and cortical arteries, arterioles and veins. It is commonly associated with Alzheimer's disease, Down's syndrome and normal aging, as well as with a variety of familial conditions related to stroke or dementia (see Frangione et al., Amyloid: J. Protein Folding Disord. 8, Suppl. 1, 36-42 (2001)). CAA can occur sporadically or be hereditary.

Senile Systemic Amyloidosis

Amyloid deposition, either systemic or focal, increases with age. For example, fibrils of wild type transthyretin (TTR) are commonly found in the heart tissue of elderly individuals. These may be asymptomatic, clinically silent, or may result in heart failure. Asymptomatic fibrillar focal deposits may also occur in the brain (Aβ), corpora amylacea of the prostate (β$_2$ microglobulin), joints and seminal vesicles.

Dialysis-Related Amyloidosis (DRA)

Plaques composed of β$_2$ microglobulin (β$_2$M) fibrils commonly develop in patients receiving long term hemodialysis or peritoneal dialysis. β$_2$ microglobulin is a 11.8 kiloDalton polypeptide and is the light chain of Class I MHC antigens, which are present on all nucleated cells. Under normal circumstances, β$_2$M is usually distributed in the extracellular space unless there is an impaired renal function, in which case β$_2$M is transported into tissues where it polymerizes to form amyloid fibrils. Failure of clearance such as in the case of impaired renal function, leads to deposition in the carpal tunnel and other sites (primarily in collagen-rich tissues of the joints). Unlike other fibril proteins, β$_2$M molecules are not produced by cleavage of a longer precursor protein and are generally present in unfragmented form in the fibrils. (Benson, supra). Retention and accumulation of this amyloid precursor has been shown to be the main pathogenic process underlying DRA. DRA is characterized by peripheral joint osteoarthropathy (e.g., joint stiffness, pain, swelling, etc.). Isoforms of β$_2$M, glycated β$_2$M, or polymers of β$_2$M in tissue are the most amyloidogenic form (as opposed to native β$_2$M).

Unlike other types of amyloidosis, $\beta_2M$ is confined largely to osteoarticular sites. Visceral depositions are rare. Occasionally, these deposits may involve blood vessels and other important anatomic sites.

Despite improved dialysis methods for removal of $\beta_2M$, the majority of patients have plasmatic $\beta_2M$ concentrations that remain dramatically higher than normal. These elevated $\beta_2M$ concentrations generally lead to Diabetes-Related Amyloidosis (DRA) and cormorbidities that contribute to mortality.

Islet Amyloid Polypeptide and Diabetes

Islet hyalinosis (amyloid deposition) was first described over a century ago as the presence of fibrous protein aggregates in the pancreas of patients with severe hyperglycemia (Opie, E L., *J Exp. Med.* 5: 397-428, 1901). Today, islet amyloid, composed predominantly of islet amyloid polypeptide (IAPP), or amylin, is a characteristic histopathological marker in over 90% of all cases of Type II diabetes (also known as Non-Insulin Dependent Diabetes, or NIDDM). These fibrillar accumulations result from the aggregation of the islet amyloid polypeptide (IAPP) or amylin, which is a 37 amino acid peptide, derived from a larger precursor peptide, called pro-IAPP.

IAPP is co-secreted with insulin in response to $\beta$-cell secretagogues. This pathological feature is not associated with insulin-dependent (Type I) diabetes and is a unifying characteristic for the heterogeneous clinical phenotypes diagnosed as NIDDM (Type II diabetes).

Longitudinal studies in cats and immunocytochemical investigations in monkeys have shown that a progressive increase in islet amyloid is associated with a dramatic decrease in the population of insulin-secreting $\beta$-cells and increased severity of the disease. More recently, transgenic studies have strengthened the relationship between IAPP plaque formation and $\beta$-cell apoptosis and dysfunction, indicating that amyloid deposition is a principal factor in increasing severity of Type II diabetes.

IAPP has also been shown to induce $\beta$-islet cell toxicity in vitro, indicating that appearance of IAPP fibrils in the pancreas of Type II or Type I diabetic patients (post-islet transplantation) could contribute to the loss of the $\beta$-cell islets (Langerhans) and organ dysfunction. In patients with Type II diabetes, the accumulation of pancreatic IAPP leads to formation of oligomeric IAPP, leading to a buildup of IAPP-amyloid as insoluble fibrous deposits which eventually destroys the insulin-producing $\beta$ cells of the islet, resulting in $\beta$ cell depletion and failure (Westermark, P., Grimelius, L., *Acta Path. Microbiol. Scand.*, sect. A. 81: 291-300, 1973; de Koning, E J P., et al., Diabetologia 36: 378-384, 1993; and Lorenzo, A., et al., *Nature* 368: 756-760, 1994). Accumulation of IAPP as fibrous deposits can also have an impact on the ratio of pro-IAPP to IAPP normally found in plasma by increasing this ratio due to the trapping of IAPP in deposits. Reduction of $\beta$ cell mass can be manifested by hyperglycemia and insulinemia. This $\beta$-cell mass loss can lead to a need for insulin therapy.

Diseases caused by the death or malfunctioning of a particular type or types of cells can be treated by transplanting into the patient healthy cells of the relevant type of cell. This approach has been used for Type I diabetes patients. Often pancreatic islet cells from a donor are cultured in vitro prior to transplantation, to allow them to recover after the isolation procedure or to reduce their immunogenicity. However, in many instances islet cell transplantation is unsuccessful, due to death of the transplanted cells. One reason for this poor success rate is IAPP, which organizes into toxic oligomers. Toxic effects may result from intracellular and extracellular accumulation of fibril oligomers. The IAPP oligomers can form fibrils and become toxic to the cells in vitro. In addition, IAPP fibrils are likely to continue to grow after the cells are transplanted and cause death or dysfunction of the cells. This may occur even when the cells are from a healthy donor and the patient receiving the transplant does not have a disease that is characterized by the presence of fibrils. For example, compounds of the present invention may also be used in preparing tissues or cells for transplantation according to the methods described in International Patent Application (PCT) number WO 01/003680.

The compounds of the invention may also stabilize the ratio of the concentrations of Pro-IAPP/IAPP, pro-Insulin/Insulin and C-peptide levels. In addition, as biological markers of efficacy, the results of the different tests, such as the arginine-insulin secretion test, the glucose tolerance test, insulin tolerance and sensitivity tests, could all be used as markers of reduced $\beta$-cell mass and/or accumulation of amyloid deposits. Such class of drugs could be used together with other drugs targeting insulin resistance, hepatic glucose production, and insulin secretion. Such compounds might prevent insulin therapy by preserving $\beta$-cell function and be applicable to preserving islet transplants.

Hormone-derived Amyloidoses

Endocrine organs may harbor amyloid deposits, particularly in aged individuals. Hormone-secreting tumors may also contain hormone-derived amyloid plaques, the fibrils of which are made up of polypeptide hormones such as calcitonin (medullary carcinoma of the thyroid), and atrial natriuretic peptide (isolated atrial amyloidosis). Sequences and structures of these proteins are well known in the art.

Miscellaneous Amyloidoses

There are a variety of other forms of amyloid disease that are normally manifest as localized deposits of amyloid. In general, these diseases are probably the result of the localized production or lack of catabolism of specific fibril precursors or a predisposition of a particular tissue (such as the joint) for fibril deposition. Examples of such idiopathic deposition include nodular AL amyloid, cutaneous amyloid, endocrine amyloid, and tumor-related amyloid. Other amyloid related diseases include those described in Table 1, such as familial amyloid polyneuropathy (FAP), senile systemic amyloidosis, Tenosynovium, familial amyloidosis, Ostertag-type, non-neuropathic amyloidosis, cranial neuropathy, hereditary cerebral hemorrhage, familial dementia, chronic dialysis, familial Creutzfeldt-Jakob disease; Gerstmann-Sträussler-Scheinker syndrome, hereditary spongiform encephalopathies, prion diseases, familial Mediterranean fever, Muckle-Well's syndrome, nephropathy, deafness, urticaria, limb pain, cardiomyopathy, cutaneous deposits, multiple myeloma, benign monoclonal gammopathy, maccoglobulinaemia, myeloma associated amyloidosis, medullary carcinomas of the thyroid, isolated atrial amyloid, and diabetes.

The compounds of the invention may be administered therapeutically or prophylactically to treat diseases associated with amyloid fibril formation, aggregation or deposition, regardless of the clinical setting. The compounds of the invention may act to ameliorate the course of an amyloid related disease using any of the following mechanisms, such as, for example but not limited to: slowing the rate of amyloid fibril formation or deposition; lessening the degree of amyloid deposition; inhibiting, reducing, or preventing amyloid fibril formation; inhibiting amyloid induced inflammation;

enhancing the clearance of amyloid from, for example, the brain; or protecting cells from amyloid induced (oligomers or fibrillar) toxicity.

In an embodiment, the compounds of the invention may be administered therapeutically or prophylactically to treat diseases associated with amyloid-β fibril formation, aggregation or deposition. The compounds of the invention may act to ameliorate the course of an amyloid-β related disease using any of the following mechanisms (this list is meant to be illustrative and not limiting): slowing the rate of amyloid-β fibril formation or deposition; lessening the degree of amyloid-β deposition; inhibiting, reducing, or preventing amyloid-β fibril formation; inhibiting neurodegeneration or cellular toxicity induced by amyloid-β; inhibiting amyloid-β induced inflammation; enhancing the clearance of amyloid-β from the brain; or favoring greater catabolism of Aβ.

Compounds of the invention may be effective in controlling amyloid-β deposition either following their entry into the brain (following penetration of the blood brain barrier) or from the periphery. When acting from the periphery, a compound may alter the equilibrium of Aβ between the brain and the plasma so as to favor the exit of Aβ from the brain. An increase in the exit of Aβ from the brain would result in a decrease in Aβ brain concentration and therefore favor a decrease in Aβ deposition. In addition, compounds that penetrate the brain may control deposition by acting directly on brain Aβ, e.g., by maintaining it in a non-fibrillar form or favoring its clearance from the brain. The compounds may slow down APP processing; may increase degradation of Aβ fibrils by macrophages or by neuronal cells; or may decrease Aβ production by activated microglia. These compounds could also prevent Aβ in the brain from interacting with the cell surface and therefore prevent neurotoxicity, neurodegeneration, or inflammation.

In a preferred embodiment, the method is used to treat Alzheimer's disease (e.g., sporadic or familial AD). The method can also be used prophylactically or therapeutically to treat other clinical occurrences of amyloid-β deposition, such as in Down's syndrome individuals and in patients with cerebral amyloid angiopathy ("CAA"), hereditary cerebral hemorrhage, or early Alzheimer's disease.

In another embodiment, the method is used to treat mild cognitive impairment. Mild Cognitive Impairment ("MCI") is a condition characterized by a state of mild but measurable impairment in thinking skills, which is not necessarily associated with the presence of dementia. MCI frequently, but not necessarily, precedes Alzheimer's disease.

Additionally, abnormal accumulation of APP and of amyloid-β protein in muscle fibers has been implicated in the pathology of sporadic inclusion body myositis (IBM) (Askanas, V., et al. (1996) *Proc. Natl. Acad. Sci. USA* 93: 1314-1319; Askanas, V. et al. (1995) *Current Opinion in Rheumatology* 7: 486-496). Accordingly, the compounds of the invention can be used prophylactically or therapeutically in the treatment of disorders in which amyloid-beta protein is abnormally deposited at non-neurological locations, such as treatment of IBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration (ARMD). ARMD is a cause of irreversible vision loss in older individuals. It is believed that Aβ deposition could be an important component of the local inflammatory events that contribute to atrophy of the retinal pigmented epithelium, drusen biogenesis, and the pathogenesis of ARMD (Johnson, et al., Proc. Natl. Acad. Sci. USA 99(18), 11830-5 (2002)).

In another embodiment, the invention also relates to a method of treating or preventing an amyloid-related disease in a subject (preferably a human) comprising administering to the subject a therapeutic amount of a compound according to the following Formulae or otherwise described herein, such that amyloid fibril formation or deposition, neurodegeneration, or cellular toxicity is reduced or inhibited. In another embodiment, the invention relates to a method of treating or preventing an amyloid-related disease in a subject (preferably a human) comprising administering to the subject a therapeutic amount of a compound according to the following Formulae or otherwise described herein, such that cognitive function is improved or stabilized or further deterioration in cognitive function is prevented, slowed, or stopped in patients with brain amyloidosis, e.g., Alzheimer's disease, Down's syndrome or cerebral amyloid angiopathy. These compounds can also improve quality of daily living in these subjects.

The therapeutic compounds of the invention may treat amyloidosis related to type II diabetes by, for example, stabilizing glycemia, preventing or reducing the loss of β cell mass, reducing or preventing hyperglycemia due to loss off cell mass, and modulating (e.g., increasing or stabilizing) insulin production. The compounds of the invention may also stabilize the ratio of the concentrations of pro-IAPP/IAPP.

The therapeutic compounds of the invention may treat AA (secondary) amyloidosis and/or AL (primary) amyloidosis, by stabilizing renal function, decreasing proteinuria, increasing creatinine clearance (e.g., by at least 50% or greater or by at least 100% or greater), by leading to remission of chronic diarrhea or weight gain (e.g., 10% or greater), reducing serum creatinine, or reducing visceral amyloid content as determined, e.g., by SAP scinitigraphy.

Compounds of the Invention

The present invention relates, at least in part, to the use of certain chemical compounds (and pharmaceutical formulations thereof) in the prevention or treatment of amyloid-related diseases, including, inter alia, Alzheimer's disease, cerebral amyloid angiopathy, inclusion body myositis, Down's syndrome, diabetes related amyloidosis, hemodialysis-related amyloidosis (β$_2$M), primary amyloidosis (e.g., λ or κ chain-related), familial amyloid polyneuropathy (FAP), senile systemic amyloidosis, familial amyloidosis, Ostertag-type non-neuropathic amyloidosis, cranial neuropathy, hereditary cerebral hemorrhage, familial dementia, chronic dialysis, familial Creutzfeldt-Jakob disease, Gerstmann-Sträussler-Scheinker syndrome, hereditary spongiform encephalopathies, prion diseases, familial Mediterranean fever, Muckle-Well's syndrome, nephropathy, deafness, urticaria, limb pain, cardiomyopathy, cutaneous deposits, multiple myeloma, benign monoclonal gammopathy, maccoglobulinaemia, myeloma associated amyloidosis, medullary carcinomas of the thyroid, and isolated atrial amyloid.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center may be of either (R)- or (S)-stereochemistry.

Such isomers can be obtained in substantially pure form by classical separation techniques and by stereochemically-controlled synthesis. Furthermore, alkenes can include either the E- or Z-geometry, where appropriate. In addition, the compounds of the present invention may exist in unsolvated as well as solvated forms with acceptable solvents such as water, THF, ethanol, and the like. In general, the solvated forms are considered equivalent to the unsolvated forms for the purposes of the present invention.

A "small molecule" refers to a compound that is not itself the product of gene transcription or translation (e.g., protein, RNA, or DNA) and preferably has a low molecular weight, e.g., less than about 2500 amu.

In general, the term "nucleophile" is art-recognized to mean a chemical group having a reactive pair of electrons that reacts with a compound by displacing a leaving group (commonly another nucleophile), such as commonly occur in aliphatic chemistry as unimolecular (known as "$S_N1$") or bimolecular ("$S_N2$") reactions. Examples of nucleophiles include uncharged compounds such as amines, mercaptans, and alcohols, and charged groups such as alkoxides, thiolates, carbanions, and a variety of organic and inorganic anions. Illustrative anionic nucleophiles include, inter alia, simple anions such as azide, cyanide, thiocyanate, acetate, formate, or chloroformate, and bisulfite. Organometallic reagents such as organocuprates, organozincs, organolithiums, Grignard reagents, enolates, and acetylides, will under appropriate reaction conditions, be suitable nucleophiles.

Similarly, an "electrophile" means an atom, molecule, or ion able to accept an electron pair, particularly a pair of electrons from a nucleophile, such as typically occurs during an electrophilic substitution reaction. In an electrophilic substitution reaction, an electrophile binds to a substrate with the expulsion of another electrophile, e.g., the substitution of a proton by another electrophile such as a nitronium ion on an aromatic substrate (e.g., benzene). Electrophiles include cyclic compounds such as epoxides, aziridines, episulfides, cyclic sulfates, carbonates, lactones, and lactams; and noncyclic electrophiles include sulfates, sulfonates (e.g., tosylates), chlorides, bromides, and iodides. Generally, an electrophile may be a saturated carbon atom (e.g., a methylene group) bonded to a leaving group; however, an electrophile may also be an unsaturated group, such as an aldehyde, ketone, ester, or conjugated ($\alpha,\beta$-unsaturated) analog thereof, which upon reaction with a nucleophile forms an adduct.

The term "leaving group" generally refers to a group that is readily displaced and substituted by a nucleophile (e.g., an amine, a thiol, an alcohol, or cyanide). Such leaving groups are well known and include carboxylates, N-hydroxysuccinimide ("NHS"), N-hydroxybenzotriazole, a halogen (fluorine, chlorine, bromine, or iodine), alkoxides, and thioalkoxides. A variety of sulfur-based leaving groups are routinely used in synthetic chemistry, including alkane sulfonyloxy groups (e.g., $C_1$-$C_4$ alkane such as methane sulfonyloxy, ethane sulfonyloxy, propane sulfonyloxy, and butane sulfonyloxy groups) and the halogenated analogs (e.g., halogeno ($C_1$-$C_4$ alkane) sulfonyloxy groups, such as trifluoromethane sulfonyloxy (i.e., triflate), 2,2,2-trichloroethane sulfonyloxy, 3,3,3-tribromopropane sulfonyloxy, and 4,4,4-trifluorobutane sulfonyloxy groups), as well as arylsulfonyloxy groups (e.g., $C_6$-$C_{10}$ aryl optionally substituted with 1 to 3 $C_1$-$C_4$ alkyl groups, such as benzene sulfonyloxy, $\alpha$-naphthylsulfonyloxy, $\beta$-naphthylsulfonyloxy, p-toluenesulfonyloxy (i.e., tosylates), 4-tert-butylbenzene sulfonyloxy, mesitylene sulfonyloxy, and 6-ethyl-$\alpha$-naphthylsulfonyloxy groups).

"Activated esters" may be represented by the formula —COL, where L is a leaving group, typical examples of which include N-hydroxysulfosuccinimidyl and N-hydroxysuccinimidyl groups; aryloxy groups substituted with electron-withdrawing groups (e.g., p-nitro, pentafluoro, pentachloro, p-cyano, or p-trifluoromethyl); and carboxylic acids activated by a carbodiimide to form an anhydride or mixed anhydride, e.g., —OCOR$^a$ or —OCNR$^a$NHR$^b$, where R$^a$ and R$^b$ are independently $C_1$-$C_6$ alkyl, $C_5$-$C_8$ alkyl (e.g., cyclohexyl), $C_1$-$C_6$ perfluoroalkyl, or $C_1$-$C_6$ alkoxy groups. An activated ester may be formed in situ or may be an isolable reagent. Sulfosuccinimidyl esters, pentafluorothiophenol esters, and sulfotetrafluorophenol are preferred activated esters. However, the ester leaving group may be, for example, substituted or unsubstituted $C_1$-$C_6$ alkyl (such as methyl, ethyl, propyl, isopropyl, butyl, isobutyl, sec-butyl, tert-butyl, pentyl, or hexyl), or substituted or unsubstituted $C_6$-$C_{14}$ aryl or heterocyclic groups, such as 2-fluoroethyl, 2-chloroethyl, 2-bromoethyl, 2,2-dibromoethyl, 2,2,2-trichloroethyl, 3-fluoropropyl, 4-chlorobutyl, methoxymethyl, 1,1-dimethyl-1-methoxymethyl, ethoxymethyl, N-propoxymethyl, isopropoxymethyl, N-butoxymethyl, tert-butoxymethyl, 1-ethoxyethyl, 1-methyl-1-methoxyethyl, 1-(isopropoxy) ethyl, 3-methoxypropyl-4-methoxybutyl, fluoromethoxymethyl, 2,2,2-trichloroethoxymethyl, bis(2-chloroethoxy)methyl, 3-fluoropropoxymethyl, 4-chlorobutoxyethyl, dibromomethoxyethyl, 2-chloroethoxypropyl, fluoromethoxybutyl, 2-methoxyethoxymethyl, ethoxymethoxyethyl, methoxyethoxypropyl, methoxyethoxybutyl, benzyl, phenethyl, 3-phenylpropyl, 4-phenylbutyl, $\alpha$-naphthylmethyl, $\beta$-naphthylmethyl, diphenylmethyl, triphenylmethyl, $\alpha$-naphthyldipheylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, 4-cyanobenzyl, 4-cyanobenzyldiphenylmethyl, or bis(2-nitrophenyl)methyl groups.

The term "electron-withdrawing group" is art-recognized and describes the ability of a substituent to attract valence electrons (e.g., pi-electrons) from neighboring atoms, e.g., the substituent is more electronegative than neighboring atoms, or it draws electrons to itself more than a hydrogen atom would at the same position. The Hammett sigma value ($\sigma$) is an accepted measure of a group's electron-donating and withdrawing ability, especially the sigma para value ($\sigma_p$). See, e.g., "Advanced Organic Chemistry" by J. March, 5$^{th}$ Ed., John Wiley & Sons, Inc., New York, pp. 368-75 (2001). The Hammett constant values are generally negative for electron-donating groups ($\sigma_p$=−0.66 for $NH_2$) and positive for electron-withdrawing groups ($\sigma_p$=0.78 for a nitro group), $\sigma_p$ indicating para substitution. Exemplary electron-withdrawing groups include nitro, acyl(ketone), formyl(aldehyde), sulfonyl, trifluoromethyl, halogeno (e.g., chloro and fluoro), and cyano groups, among others. Conversely, an "electron-donating group" designates a substituent that contributes electrons more than hydrogen would if it occupied the same position in the molecule. Examples include amino (including alkylamino and dialkylamino), aryl, alkoxy (including aralkoxy), aryloxy, mercapto and alkylthio, and hydroxyl groups, among others.

As used herein, "alkyl" groups include saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (isopropyl, tert-butyl, sec-butyl, isobutyl, etc.), and alkyl-substituted alkyl groups (e.g., alkyl-substituted cycloalkyl groups and cycloalkyl-substituted alkyl groups). The term "aliphatic group" includes organic moieties characterized by straight or branched-chains, typically having between 1 and 22 carbon atoms. In complex structures, the chains may be branched, bridged, or cross-linked. Aliphatic groups include alkyl groups, alkenyl groups, and alkynyl groups.

In certain embodiments, a straight-chain or branched-chain alkyl group may have 30 or fewer carbon atoms in its backbone, e.g., $C_1$-$C_{30}$ for straight-chain or $C_3$-$C_{30}$ for branched-chain. In certain embodiments, a straight-chain or branched-chain alkyl group may have 20 or fewer carbon atoms in its backbone, e.g., $C_1$-$C_{20}$ for straight-chain or $C_3$-$C_{20}$ for branched-chain, and more preferably 18 or fewer. Likewise, preferred cycloalkyl groups have from 4-10 carbon atoms in their ring structure, and more preferably have 4-7 carbon atoms in the ring structure. The term "lower alkyl" refers to alkyl groups having from 1 to 6 carbons in the chain, and to cycloalkyl groups having from 3 to 6 carbons in the ring structure.

Unless the number of carbons is otherwise specified, "lower" as in "lower aliphatic," "lower alkyl," "lower alkenyl," etc. as used herein means that the moiety has at least one and less than about 8 carbon atoms. In certain embodiments, a straight-chain or branched-chain lower alkyl group has 6 or fewer carbon atoms in its backbone (e.g., $C_1$-$C_6$ for straight-chain, $C_3$-$C_6$ for branched-chain), and more preferably 4 or fewer. Likewise, preferred cycloalkyl groups have from 3-8 carbon atoms in their ring structure, and more preferably have 5 or 6 carbons in the ring structure. The term "$C_1$-$C_6$" as in "$C_1$-$C_6$ alkyl" means alkyl groups containing 1 to 6 carbon atoms.

Moreover, unless otherwise specified the term alkyl includes both "unsubstituted alkyls" and "substituted alkyls," the latter of which refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, or aromatic (including heteroaromatic) groups.

An "arylalkyl" group is an alkyl group substituted with an aryl group (e.g., phenylmethyl (i.e., benzyl)). An "alkylaryl" moiety is an aryl group substituted with an alkyl group (e.g., p-methylphenyl (i.e., p-tolyl)). The term "n-alkyl" means a straight-chain (i.e., unbranched) unsubstituted alkyl group. An "alkylene" group is a divalent analog of the corresponding alkyl group. The terms "alkenyl" and "alkynyl" refer to unsaturated aliphatic groups analogous to alkyls, but which contain at least one double or triple carbon-carbon bond respectively. Suitable alkenyl and alkynyl groups include groups having 2 to about 12 carbon atoms, preferably from 2 to about 6 carbon atoms.

The term "aromatic group" or "aryl group" includes unsaturated and aromatic cyclic hydrocarbons as well as unsaturated and aromatic heterocycles containing one or more rings. Aryl groups may also be fused or bridged with alicyclic or heterocyclic rings that are not aromatic so as to form a polycycle (e.g., tetralin). An "arylene" group is a divalent analog of an aryl group. Aryl groups can also be fused or bridged with alicyclic or heterocyclic rings which are not aromatic so as to form a polycycle (e.g., tetralin).

The term "heterocyclic group" includes closed ring structures analogous to carbocyclic groups in which one or more of the carbon atoms in the ring is an element other than carbon, for example, nitrogen, sulfur, or oxygen. Heterocyclic groups may be saturated or unsaturated. Additionally, heterocyclic groups (such as pyrrolyl, pyridyl, isoquinolyl, quinolyl, purinyl, and furyl) may have aromatic character, in which case they may be referred to as "heteroaryl" or "heteroaromatic" groups.

Unless otherwise stipulated, aryl and heterocyclic (including heteroaryl) groups may also be substituted at one or more constituent atoms. Examples of heteroaromatic and heteroalicyclic groups may have 1 to 3 separate or fused rings with 3 to about 8 members per ring and one or more N, O, or S heteroatoms. In general, the term "heteroatom" includes atoms of any element other than carbon or hydrogen, preferred examples of which include nitrogen, oxygen, sulfur, and phosphorus. Heterocyclic groups may be saturated or unsaturated or aromatic.

Examples of heterocycles include, but are not limited to, acridinyl; azocinyl; benzimidazolyl; benzofuranyl; benzothiofuranyl; benzothiophenyl; benzoxazolyl; benzthiazolyl; benztriazolyl; benztetrazolyl; benzisoxazolyl; benzisothiazolyl; benzimidazolinyl; carbazolyl; 4aH-carbazolyl; carbolinyl; chromanyl; chromenyl; cinnolinyl; decahydroquinolinyl; 2H,6H-1,5,2-dithiazinyl; dihydrofuro[2,3-b]tetrahydrofuran; furanyl; furazanyl; imidazolidinyl; imidazolinyl; imidazolyl; 1H-indazolyl; indolenyl; indolinyl; indolizinyl; indolyl; 3H-indolyl; isobenzofuranyl; isochromanyl; isoindazolyl; isoindolinyl; isoindolyl; isoquinolinyl; isothiazolyl; isoxazolyl; methylenedioxyphenyl; morpholinyl; naphthyridinyl; octahydroisoquinolinyl; oxadiazolyl; 1,2,3-oxadiazolyl; 1,2,4-oxadiazolyl; 1,2,5-oxadiazolyl; 1,3,4-oxadiazolyl; oxazolidinyl; oxazolyl; oxazolidinyl; pyrimidinyl; phenanthridinyl; phenanthrolinyl; phenazinyl; phenothiazinyl; phenoxathiinyl; phenoxazinyl; phthalazinyl; piperazinyl; piperidinyl; piperidonyl; 4-piperidonyl; piperonyl; pteridinyl; purinyl; pyranyl; pyrazinyl; pyrazolidinyl; pyrazolinyl; pyrazolyl; pyridazinyl; pyridooxazole; pyridoimidazole; pyridothiazole; pyridinyl; pyridyl; pyrimidinyl; pyrrolidinyl; pyrrolinyl; 2H-pyrrolyl; pyrrolyl; quinazolinyl; quinolinyl; 4H-quinolizinyl; quinoxalinyl; quinuclidinyl; tetrahydrofuranyl; tetrahydroisoquinolinyl; tetrahydroquinolinyl; tetrazolyl; 6H-1,2,5-thiadiazinyl; 1,2,3-thiadiazolyl; 1,2,4-thiadiazolyl; 1,2,5-thiadiazolyl; 1,3,4-thiadiazolyl; thianthrenyl; thiazolyl; thienyl; thienothiazolyl; thienooxazolyl; thienoimidazolyl; thiophenyl; triazinyl; 1,2,3-triazolyl; 1,2,4-triazolyl; 1,2,5-triazolyl; 1,3,4-triazolyl; and xanthenyl. Preferred heterocycles include, but are not limited to, pyridinyl; furanyl; thienyl; pyrrolyl; pyrazolyl; pyrrolidinyl; imidazolyl; indolyl; benzimidazolyl; 1H-indazolyl; oxazolidinyl; benzotriazolyl; benzisoxazolyl; oxindolyl; benzoxazolinyl; and isatinoyl groups. Also included are fused ring and spiro compounds containing, for example, the above heterocycles.

A common hydrocarbon aryl group is a phenyl group having one ring. Two-ring hydrocarbon aryl groups include naphthyl, indenyl, benzocyclooctenyl, benzocycloheptenyl, pentalenyl, and azulenyl groups, as well as the partially hydrogenated analogs thereof such as indanyl and tetrahydronaphthyl. Exemplary three-ring hydrocarbon aryl groups include acephthylenyl, fluorenyl, phenalenyl, phenanthrenyl, and anthracenyl groups.

Aryl groups also include heteromonocyclic aryl groups, i.e., single-ring heteroaryl groups, such as thienyl, furyl, pyranyl, pyrrolyl, imidazolyl, pyrazolyl, pyridinyl, pyrazinyl, pyrimidinyl, and pyridazinyl groups; and oxidized analogs thereof such as pyridonyl, oxazolonyl, pyrazolonyl, isoxazolonyl, and thiazolonyl groups. The corresponding hydrogenated (i.e., non-aromatic) heteromonocylic groups include pyrrolidinyl, pyrrolinyl, imidazolidinyl, imidazolinyl, pyrazolidinyl, pyrazolinyl, piperidyl and piperidino, piperazinyl, and morpholino and morpholinyl groups.

Aryl groups also include fused two-ring heteroaryls such as indolyl, isoindolyl, indolizinyl, indazolyl, quinolinyl, isoquinolinyl, phthalazinyl, quinoxalinyl, quinazolinyl, cinnolinyl, chromenyl, isochromenyl, benzothienyl, benzimidazolyl, benzothiazolyl, purinyl, quinolizinyl, isoquinolonyl, quinolonyl, naphthyridinyl, and pteridinyl groups, as well as the partially hydrogenated analogs such as chromanyl, isochromanyl, indolinyl, isoindolinyl, and tetrahydroindolyl groups. Aryl groups also include fused three-ring groups such as phenoxathiinyl, carbazolyl, phenanthridinyl, acridinyl, perimidinyl, phenanthrolinyl, phenazinyl, phenothiazinyl, phenoxazinyl, and dibenzofuranyl groups.

Some typical aryl groups include substituted or unsubstituted 5- and 6-membered single-ring groups. In another aspect, each Ar group may be selected from the group consisting of substituted or unsubstituted phenyl, pyrrolyl, furyl, thienyl, thiazolyl, isothiaozolyl, imidazolyl, triazolyl, tetrazolyl, pyrazolyl, oxazolyl, isooxazolyl, pyridinyl, pyrazinyl, pyridazinyl, and pyrimidinyl groups. Further examples include substituted or unsubstituted phenyl, 1-naphthyl, 2-naphthyl, biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl groups.

The term "amine" or "amino," as used herein, refers to an unsubstituted or substituted moiety of the formula $-NR^aR^b$, in which $R^a$ and $R^b$ are each independently hydrogen, alkyl, aryl, or heterocyclyl, or $R^a$ and $R^b$, taken together with the nitrogen atom to which they are attached, form a cyclic moiety having from 3 to 8 atoms in the ring. Thus, the term amino includes cyclic amino moieties such as piperidinyl or pyrrolidinyl groups, unless otherwise stated. Thus, the term "alkylamino" as used herein means an alkyl group having an amino group attached thereto. Suitable alkylamino groups include groups having 1 to about 12 carbon atoms, preferably from 1 to about 6 carbon atoms. The term amino includes compounds or moieties in which a nitrogen atom is covalently bonded to at least one carbon or heteroatom. The term "dialkylamino" includes groups wherein the nitrogen atom is bound to at least two alkyl groups. The term "arylamino" and "diarylamino" include groups wherein the nitrogen is bound to at least one or two aryl groups, respectively. The term "alkylarylamino" refers to an amino group which is bound to at least one alkyl group and at least one aryl group. The term "alkaminoalkyl" refers to an alkyl, alkenyl, or alkynyl group substituted with an alkylamino group. The term "amide" or "aminocarbonyl" includes compounds or moieties which contain a nitrogen atom which is bound to the carbon of a carbonyl or a thiocarbonyl group.

The term "alkylthio" refers to an alkyl group, having a sulfhydryl group attached thereto. Suitable alkylthio groups include groups having 1 to about 12 carbon atoms, preferably from 1 to about 6 carbon atoms.

The term "alkylcarboxyl" as used herein means an alkyl group having a carboxyl group attached thereto.

The term "alkoxy" as used herein means an alkyl group having an oxygen atom attached thereto. Representative alkoxy groups include groups having 1 to about 12 carbon atoms, preferably 1 to about 6 carbon atoms, e.g., methoxy, ethoxy, propoxy, tert-butoxy and the like. Examples of alkoxy groups include methoxy, ethoxy, isopropyloxy, propoxy, butoxy, and pentoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc., as well as perhalogenated alkyloxy groups.

The term "acylamino" includes moieties wherein an amino moiety is bonded to an acyl group. For example, the acylamino group includes alkylcarbonylamino, arylcarbonylamino, carbamoyl and ureido groups.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "ether" or "ethereal" includes compounds or moieties which contain an oxygen bonded to two carbon atoms. For example, an ether or ethereal group includes "alkoxyalkyl" which refers to an alkyl, alkenyl, or alkynyl group substituted with an alkoxy group.

A "sulfonate" group is a $-SO_3H$ or $-SO_3^-X^+$ group bonded to a carbon atom, where $X^+$ is a cationic counter ion group. Similarly, a "sulfonic acid" compound has a $-SO_3H$ or $-SO_3^-X^+$ group bonded to a carbon atom, where $X^+$ is a cationic group. A "sulfate" as used herein is a $-OSO_3H$ or $-OSO_3^-X^+$ group bonded to a carbon atom, and a "sulfuric acid" compound has a $-SO_3H$ or $-OSO_3^-X^+$ group bonded to a carbon atom, where $X^+$ is a cationic group. According to the invention, a suitable cationic group may be a hydrogen atom. In certain cases, the cationic group may actually be another group on the therapeutic compound that is positively charged at physiological pH, for example an amino group.

A "counter ion" is required to maintain electroneutrality. Examples of anionic counter ions include halide, triflate, sulfate, nitrate, hydroxide, carbonate, bicarbonate, acetate, phosphate, oxalate, cyanide, alkylcarboxylate, N-hydroxysuccinimide, N-hydroxybenzotriazole, alkoxide, thioalkoxide, alkane sulfonyloxy, halogenated alkane sulfonyloxy, arylsulfonyloxy, bisulfate, oxalate, valerate, oleate, palmitate, stearate, laurate, borate, benzoate, lactate, citrate, maleate, fumarate, succinate, tartrate, naphthylate mesylate, glucoheptonate, or lactobionate. Compounds containing a cationic group covalently bonded to an anionic group may be referred to as an "internal salt."

The term "nitro" means —NO₂; the term "halogen" or "halogeno" or "halo" designates —F, —Cl, —Br or —I; the term "thiol," "thio," or "mercapto" means SH; and the term "hydroxyl" or "hydroxy" means —OH.

The term "acyl" refers to a carbonyl group that is attached through its carbon atom to a hydrogen (i.e., a formyl), an aliphatic group (e.g., acetyl), an aromatic group (e.g., benzoyl), and the like. The term "substituted acyl" includes acyl groups where one or more of the hydrogen atoms on one or more carbon atoms are replaced by, for example, an alkyl group, alkynyl group, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless otherwise specified, the chemical moieties of the compounds of the invention, including those groups discussed above, may be "substituted or unsubstituted." In some embodiments, the term "substituted" means that the moiety has substituents placed on the moiety other than hydrogen (i.e., in most cases, replacing a hydrogen), which allow the molecule to perform its intended function. Examples of substituents include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, and heteroaryl groups, as well as $(CR'R'')_{0-3}$ NR'R'' (e.g., —NH₂), $(CR'R'')_{0-3}$—₃CN (e.g., —CN), —NO₂, halogen (e.g., —F, —Cl, —Br, or —I), $(CR'R'')_{0-3}$C(halogen)₃ (e.g., —CF₃), $(CR'R'')_{0-3}$CH(halogen)₂, $(CR'R'')_{0-3}$CH₂(halogen), $(CR'R'')_{0-3}$CONR'R'', $(CR'R'')_{0-3}$(CNH)NR'R'', $(CR'R'')_{0-3}$S(O)$_{1-2}$NR'R'', $(CR'R'')_{0-3}$CHO, $(CR'R'')_{0-3}$O$(CR'R'')_{0-3}$ H, $(CR'R'')_{0-3}$S(O)$_{0-3}$R' (e.g., —SO₃H), $(CR'R'')_{0-3}$O$(CR'R'')_{0-3}$ H (e.g., —CH₂OCH₃ and —OCH₃), $(CR'R'')_{0-3}$S$(CR'R'')_{0-3}$ H (e.g., —SH and —SCH₃), $(CR'R'')_{0-3}$OH (e.g., —OH), $(CR'R'')_{0-3}$COR', $(CR'R'')_{0-3}$ (substituted or unsubstituted phenyl), $(CR'R'')_{0-3}$($C_3$-$C_8$ cycloalkyl), $(CR'R'')_{0-3}$CO₂R' (e.g., —CO₂H), and $(CR'R'')_{0-3}$OR' groups, wherein R' and R" are each independently hydrogen, a $C_1$-$C_5$ alkyl, $C_2$-$C_5$ alkenyl, $C_2$-$C_5$ alkynyl, or aryl group; or the side chain of any naturally occurring amino acid.

In another embodiment, a substituent may be selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-10}$NR'R'' (e.g., —NH₂), $(CR'R'')_{0-10}$CN (e.g., —CN), NO₂, halogen (e.g., F, Cl, Br, or I), $(CR'R'')_{0-10}$C(halogen)₃ (e.g., —CF₃), $(CR'R'')_{0-10}$CH(halogen)₂, $(CR'R'')_{0-10}$CH₂(halogen), $(CR'R'')_{0-10}$CONR'R'', $(CR'R'')_{0-10}$(CNH)NR'R'', $(CR'R'')_{0-10}$S(O)$_{1-2}$NR'R'', $(CR'R'')_{0-10}$CHO, $(CR'R'')_{0-10}$O$(CR'R'')_{0-10}$H, $(CR'R'')_{0-10}$S(O)$_{0-3}$R' (e.g., —SO₃H), $(CR'R'')_{0-10}$O$(CR'R'')_{0-10}$H (e.g., —CH₂OCH₃ and —OCH₃), $(CR'R'')_{0-10}$S$(CR'R'')_{0-3}$H (e.g., —SH and —SCH₃), $(CR'R'')_{0-10}$OH (e.g., —OH), $(CR'R'')_{0-10}$COR', $(CR'R'')_{0-10}$ (substituted or unsubstituted phenyl), (CR'R")$_{0-10}$ ($C_3$-$C_8$ cycloalkyl), $(CR'R'')_{0-10}$CO₂R' (e.g., —CO₂H), or $(CR'R'')_{0-10}$OR' group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group, or R' and R" taken together are a benzylidene group or a —(CH₂)₂O(CH₂)₂— group.

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more.

In some embodiments, a "substituent" may be selected from the group consisting of, for example, halogeno, trifluoromethyl, nitro, cyano, $C_1$-$C_6$ alkyl, $C_2$-$C_6$ alkenyl, $C_2$-$C_6$ alkynyl, $C_1$-$C_6$ alkylcarbonyloxy, arylcarbonyloxy, $C_1$-$C_6$ alkoxycarbonyloxy, aryloxycarbonyloxy, $C_1$-$C_6$ alkylcarbonyl, $C_1$-$C_6$ alkoxycarbonyl, $C_1$-$C_6$ alkoxy, $C_1$-$C_6$ alkylthio, arylthio, heterocyclyl, aralkyl, and aryl (including heteroaryl) groups.

In one embodiment, the invention pertains to compounds of Formula I:

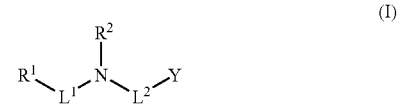

(I)

wherein:

$R^1$ is a substituted or unsubstituted cycloalkyl, heterocyclic, aryl, arylcycloalkyl, bicyclic or tricyclic ring, a bicyclic or tricyclic fused ring group, or a substituted or unsubstituted $C_2$-$C_{10}$ alkyl group;

$R^2$ is selected from a group consisting of hydrogen, alkyl, mercaptoalkyl, alkenyl, alkynyl, cycloalkyl, aryl, arylalkyl, thiazolyl, triazolyl, imidazolyl, benzothiazolyl, and benzoimidazolyl;

Y is SO₃⁻X⁺, OSO₃⁻X⁺, or SSO₃⁻X⁺;

X⁺ is hydrogen, a cationic group, or ester-forming group; and each of $L^1$ and $L^2$ is independently a substituted or unsubstituted $C_1$-$C_5$ alkyl group or absent, or a pharmaceutically acceptable salt, ester or prodrug thereof, provided that when $R_1$ is alkyl, $L^1$ is absent.

In a further embodiment, the invention pertains to compounds of Formula II:

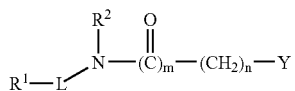

wherein:

R[1] is a substituted or unsubstituted cyclic, bicyclic, tricyclic, or benzoheterocyclic group or a substituted or unsubstituted $C_2$-$C_{10}$ alkyl group;

R[2] is hydrogen, alkyl, mercaptoalkyl, alkenyl, alkynyl, cycloalkyl, aryl, arylalkyl, thiazolyl, triazolyl, imidazolyl, benzothiazolyl, benzoimidazolyl, or linked to R[1] to form a heterocycle;

Y is $SO_3^-X^+$, $OSO_3^-X^+$, or $SSO_3^-X^+$;

X[+] is hydrogen, a cationic group, or an ester forming moiety;

m is 0 or 1;

n is 1, 2, 3, or 4;

L is substituted or unsubstituted $C_1$-$C_3$ alkyl group or absent, or a pharmaceutically acceptable salt, ester, or prodrug thereof, provided that when R[1] is alkyl, L is absent.

In a further embodiment, R[2] is hydrogen. In another further embodiment, R[1] is straight chain alkyl, for example, ethyl, n-pentyl, n-heptyl, or n-octyl. In another embodiment, R[1] is t-butyl. In yet another alternate embodiment, R[1] is $C_7$-$C_{10}$ bicycloalkyl or tricycloalkyl, such as, for example, tricyclo[3.3.1.0$^{3,7}$]decyl (or adamantyl), bicyclo[2.1.2]heptyl, or indolyl. In another alternate embodiment, R[1] is tetrahydronaphthyl.

In one embodiment, L[2] is —(CH$_2$)$_3$—. In another further embodiment, L[2] is —(CH$_2$)$_4$— or —(CH$_2$)$_5$—. In yet another further embodiment, L$_2$ is —(CH$_2$)$_2$—. In yet another further embodiment, L[2] is substituted alkyl, e.g., —CH$_2$—(CHOH)—CH$_2$—.

In another embodiment, L[1] is CH$_2$CH$_2$ or absent.

In a further embodiment, R[1] is branched alkyl, e.g., t-butyl. In another embodiment, R[1] is adamanyl. In another embodiment, R[1] is cyclic alkyl, e.g., cyclopropyl, cyclohexyl, cycloheptyl, cyclo-octyl, etc. The cycloalkyl moieties may be substituted further, e.g., with additional alkyl groups or other groups which allow the molecule to perform its intended function. In another embodiment, R[1] is alkyl substituted with a propargyl moiety (e.g., HC≡C—). In another embodiment, R[1] is cyclohexyl substituted with one or more methyl or propargyl groups.

In certain embodiments, R[1] is cyclopropyl or cyclohexyl. In certain embodiments, the cyclopropyl or cyclohexyl group is substituted with an ether group or an alkyl group. In certain further embodiments, the ether group is a benzyl ether group.

In another embodiment, wherein R[1] is alkyl, it is substituted with groups such as phenyl, or hydroxy.

In other embodiments, the compound of the invention is selected from the group consisting of:

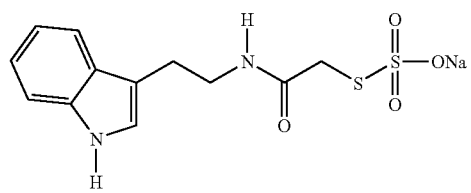

-continued

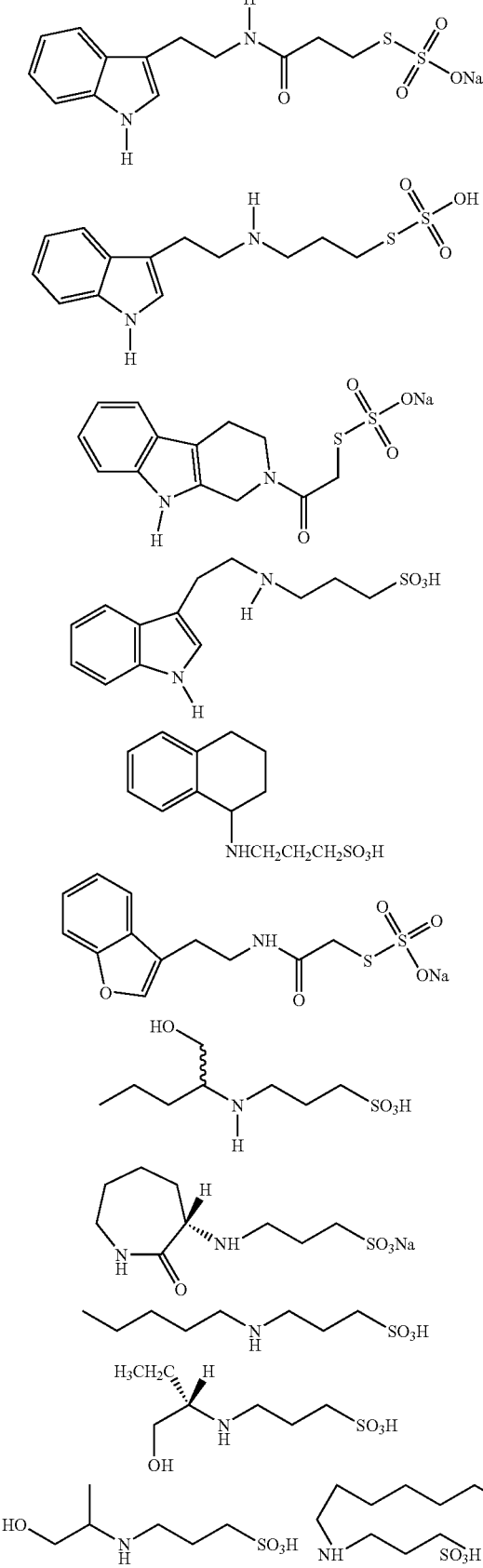

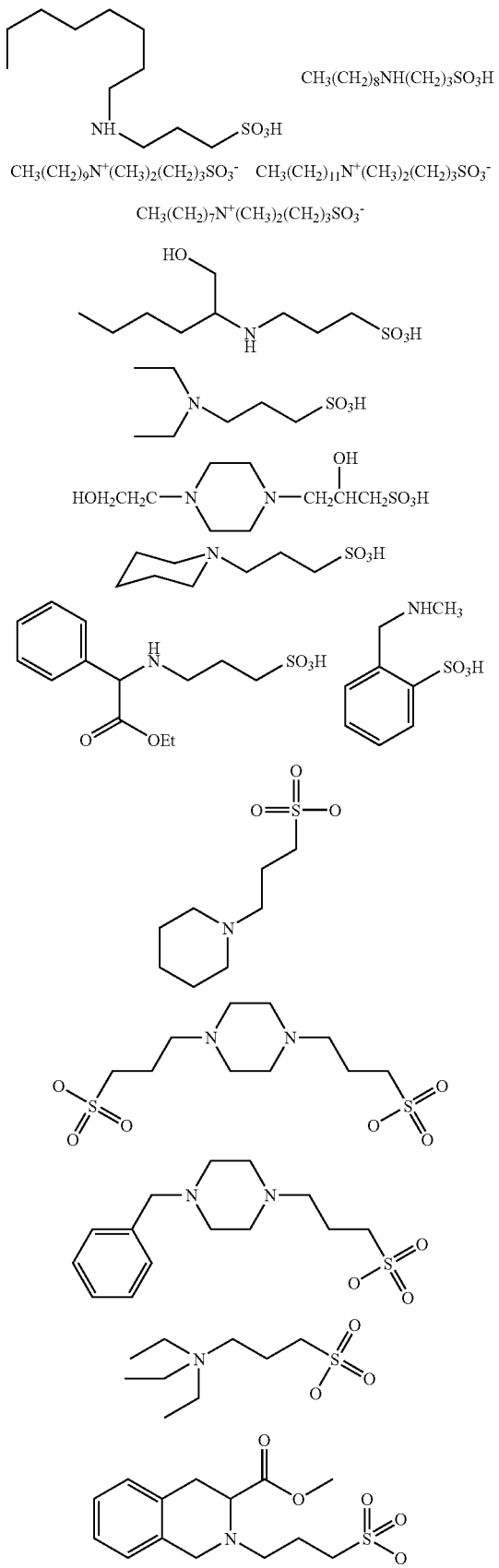
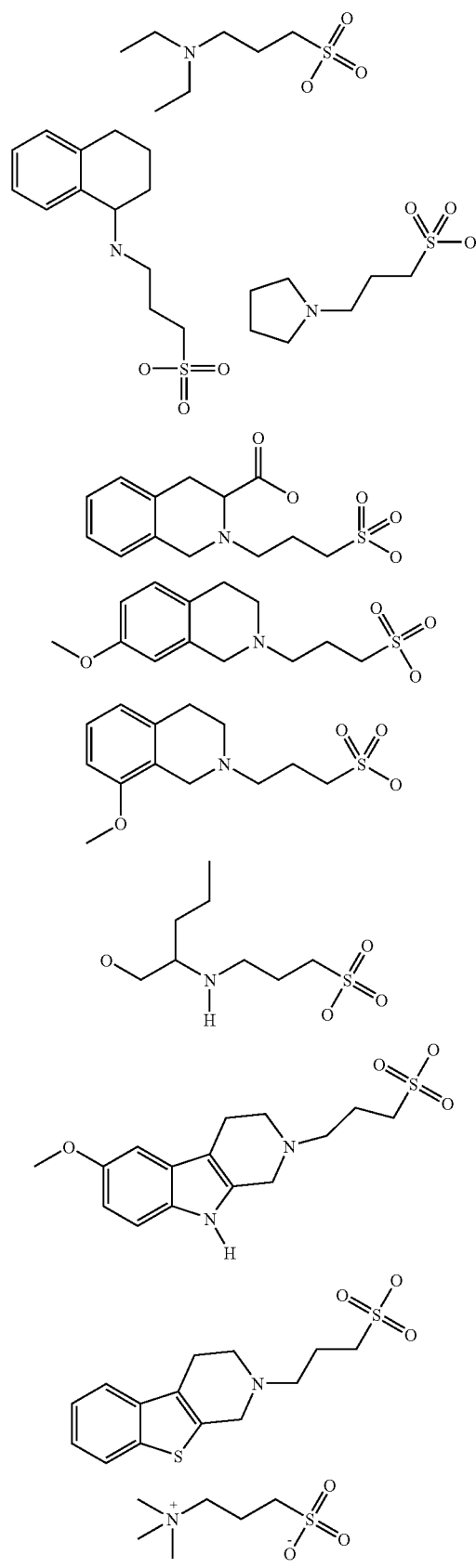

-continued
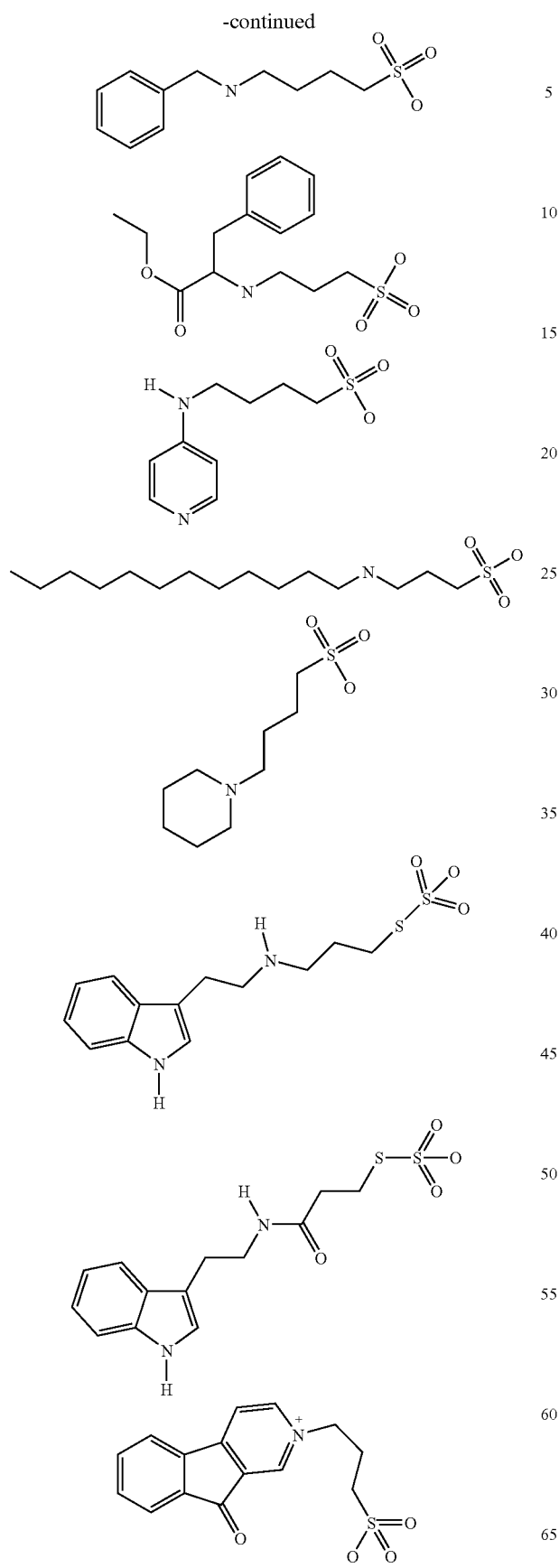
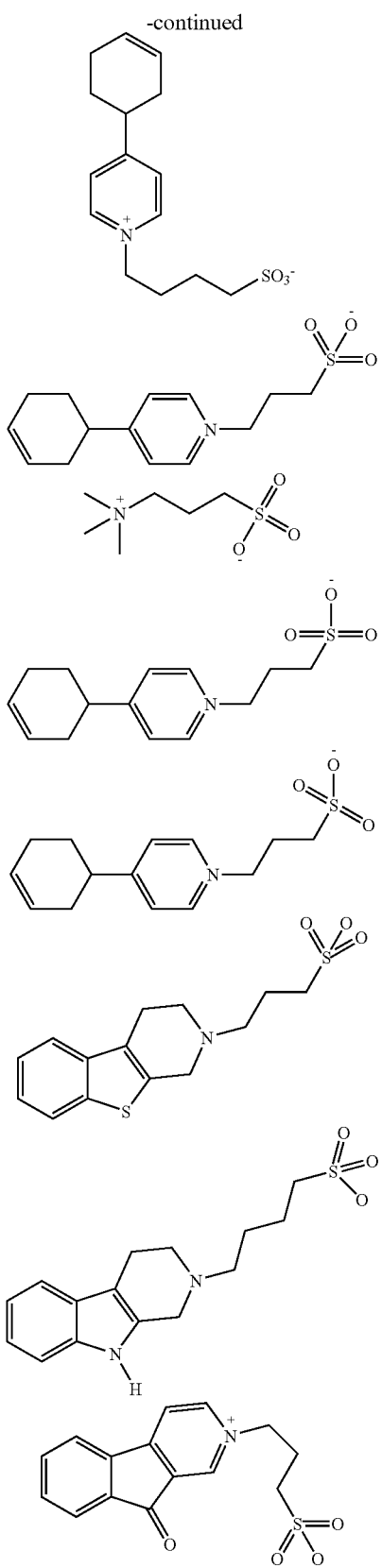
and pharmaceutically acceptable salts, esters and prodrugs thereof.

In another embodiment, the invention pertains to compounds of Formula III:

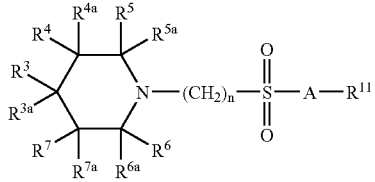

(III)

wherein:
A is nitrogen or oxygen;
$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;
Q is hydrogen, thiazolyl, triazolyl, imidazolyl, benzothiazolyl, or benzoimidazolyl;
x is 0, 1, 2, 3, or 4;
n is 0, 1, 2, 3, 4, 5, 6, 7, 8, 9, or 10;
$R^3$, $R^{3a}$, $R^4$, $R^{4a}$, $R^5$, $R^{5a}$, $R^6$, $R^{6a}$, $R^7$ and $R^{7a}$ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, or two R groups on adjacent ring atoms taken together with the ring atoms form a double bond, provided that one of $R^3$, $R^{3a}$, $R^4$, $R^{4a}$, $R^5$, $R^{5a}$, $R^6$, $R^{6a}$, $R^7$ and $R^{7a}$ is a moiety of the Formula IIIa:

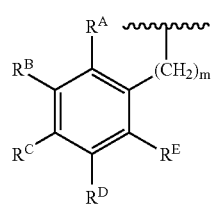

(IIIa)

wherein:
m is 0, 1, 2, 3, or 4;
$R^A$, $R^B$, $R^C$, $R^D$, and $R^E$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl; and pharmaceutically acceptable salts, prodrugs and esters thereof, provided that said compound is not 3-(4-phenyl-1,2,3,6-tetrahydro-1-pyridyl)-1-propanesulfonic acid.

In a further embodiment, n is 2, 3 or 4.
In another embodiment, $R^{11}$ is a salt-forming cation. Examples of salt forming cations include pharmaceutically acceptable salts described herein as well as lithium, sodium, potassium, magnesium, calcium, barium, zinc, iron, and ammonium. In another embodiment, $R^{11}$ is an ester-forming group. An ester-forming group includes groups which when bound form an ester. Examples of such groups include substituted or unsubstituted alkyl, aryl, alkenyl, alkynyl, or cycloalkyl. In another embodiment, A is oxygen.
In another embodiment, $R^3$ and $R^4$ are taken together with the carbon atoms to which they are attached to form a double bond. In another embodiment, $R^A$, $R^B$, $R^C$, $R^D$, and $R^F$ are each hydrogen. $R^A$, $R^B$, $R^D$, and $R^E$ are each hydrogen and $R^C$ is a halogen, such as fluorine, chlorine, iodine, or bromine.

In another embodiment, $R^3$ or $R^{5a}$ is a moiety of Formula IIIa.

In another embodiment, $R^4$, $R^5$, $R^6$, and $R^7$ are each hydrogen. In another further embodiment, $R^{4a}$, $R^{5a}$, $R^{6a}$, and $R^{7a}$ are each hydrogen.

In another, $R^{3a}$ is hydroxyl, cyano, acyl, or hydroxyl.

In another further embodiment, $R^{11}$ and A taken together are a natural or unnatural amino acid residue or a pharmaceutically acceptable salt or ester thereof. Examples of amino acid residues include esters and salts of phenylalanine and leucine.

In another embodiment, m is 0, 1, or 3.
Examples of compounds of Formula III include, but are not limited to:

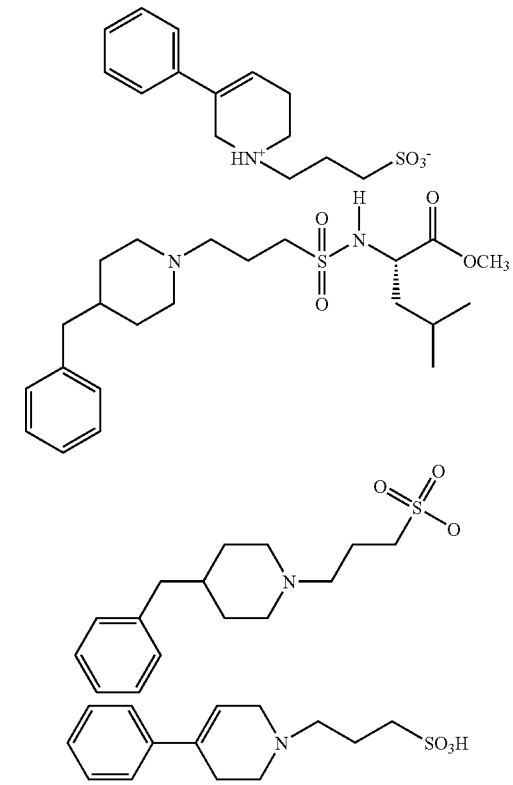

and pharmaceutically acceptable salts, prodrugs and esters thereof.

In another embodiment, the invention pertains to compounds of Formula IV:

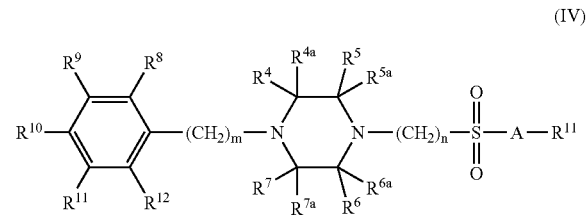

(IV)

wherein:

A is nitrogen or oxygen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

$R^4$, $R^{4a}$, $R^5$, $R^{5a}$, $R^6$, $R^{6a}$, $R^7$, and $R^{7a}$ are each independently hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, $R^4$ and $R^5$ taken together, with the ring atoms they are attached to, form a double bond, or $R^6$ and $R^7$ taken together, with the ring atoms they are attached to, form a double bond;

m is 0, 1, 2, 3, or 4;

$R^8$, $R^9$, $R^{10}$, $R^{11}$, and $R^{12}$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl, and pharmaceutically acceptable salts, prodrugs and esters thereof.

In another embodiment, $R^{11}$ is a salt-forming cation. Examples of salt forming cations include pharmaceutically acceptable salts described herein as well as lithium, sodium, potassium, magnesium, calcium, barium, zinc, iron, and ammonium. In another embodiment, $R^{11}$ is an ester-forming group. An ester-forming group includes groups which when bound form an ester. Examples of such groups include substituted or unsubstituted alkyl, aryl, alkenyl, alkynyl, or cycloalkyl. In another embodiment, A is oxygen.

In another embodiment, m is 0 or 1. In another further embodiment, n is 2, 3, or 4. In another further embodiment, $R^4$, $R^5$, $R^6$ and $R^7$ are each hydrogen. $R^{4a}$, $R^{5a}$, $R^{6a}$, and $R^{7a}$ also may be hydrogen. Examples of $R^8$, $R^9$, $R^{10}$, $R^{11}$, and $R^{12}$ include hydrogen. In another embodiment $R^8$, $R^9$, $R^{11}$, $R^{12}$ are each hydrogen, and $R^{10}$ is a halogen, (e.g., fluorine, chlorine, bromine, or iodine), nitro, or alkyl (e.g., methyl, ethyl, butyl).

In another embodiment, A-$R^{11}$ may be the residue of an amino acid, e.g., a phenylalanine residue. In another embodiment, $R^9$, $R^{10}$, $R^{11}$ and $R^{12}$ are each hydrogen, and $R^8$ is not hydrogen, e.g., halogen, e.g., fluorine, bromine, chlorine, or iodine.

In another embodiment, the compound is:

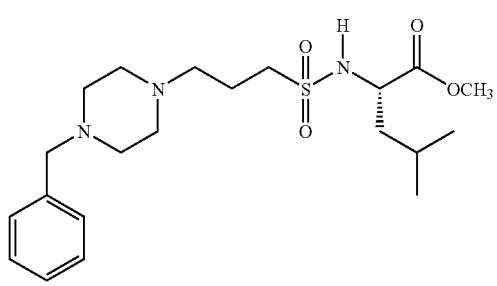

and pharmaceutically acceptable salts, esters, and prodrugs thereof.

In another embodiment, the invention pertains to compounds of Formula V:

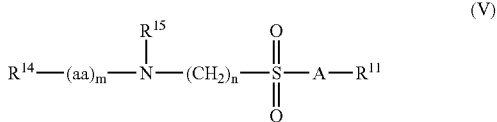

wherein:

A is nitrogen or oxygen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

n is 0, 1, 2, 3, 4, 5, 6, 7, 8, 9, or 10;

aa is a natural or unnatural amino acid residue;

m is 0, 1, 2, or 3;

$R^{14}$ is hydrogen or protecting group;

$R^{15}$ is hydrogen, alkyl or aryl, and pharmaceutically acceptable salts, esters, and prodrugs thereof.

In another embodiment, $R^{11}$ is a salt-forming cation. Examples of salt forming cations include pharmaceutically acceptable salts described herein as well as lithium, sodium, potassium, magnesium, calcium, barium, zinc, iron, and ammonium. In another embodiment, $R^{11}$ is an ester-forming group. An ester-forming group includes groups which when bound form an ester. Examples of such groups include substituted or unsubstituted alkyl, aryl, alkenyl, alkynyl, or cycloalkyl. In another embodiment, A is oxygen.

In an embodiment, n is 2, 3 or 4. In certain embodiments, m is 0. In certain embodiments, A-$R^{11}$ is a residue of a natural amino acid, or a salt or ester thereof. Examples of amino acid residues, include, but are not limited to, leucine or phenylalanine residues, and pharmaceutically acceptable salts and esters thereof. Examples of possible esters include methyl, ethyl, and t-butyl.

In another embodiment, m is 1. Examples of aa include natural and unnatural amino acid residues such as phenylalanine, glycine, and leucine.

In another embodiment, $(aa)_m$ is a residue of phe-phe; and pharmaceutically acceptable salts or an appropriate protecting group.

In certain embodiments, $R^{15}$ is hydrogen or substituted alkyl, e.g., arylalkyl.

The term "unnatural amino acid" refers to any derivative of a natural amino acid including D forms, and α- and β-amino acid derivatives. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): β-alanine (β-ALA), γ-aminobutyric acid (GABA), 2-aminobutyric acid (2-Abu), α,β-dehydro-2-aminobutyric acid (8-AU), 1-aminocyclopropane-1-carboxylic acid (ACPC), aminoisobutyric acid (Aib), 2-amino-thiazoline-4-carboxylic acid, 5-aminovaleric acid (5-Ava), 6-aminohexanoic acid (6-Ahx), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-aamino-5-cyclohexyl-3-hydroxypentanoic acid (ACHPA), para-aminophenylalanine (4-$NH_2$-Phe), biphenylalanine (Bip), para-bromophenylalanine (4-Br-Phe), ortho-chlorophenylalanine] (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), 2,3-diaminopropionic acid (Dpr), 2,4-diaminobutyric acid (Dbu), 3,4-dichlorophenylalanine (3,4-$Cl_2$-Phe), 3,4-difluorophenylalanine (3,4-$F_2$-Phe), 3,5-diiodotyrosine (3,5-$I_2$-Tyr), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), 5-hydroxytryptophan (5-OH-Trp), hydroxyproline (Hyp), para-iodophenylalanine (4-1-Phe), 3-iodotyrosine (3-1-Tyr), indoline-2-carboxylic acid (Idc), isonipecotic acid (Inp), meta-methyltyrosine (3-Me-Tyr), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th). Additionally, N-alkylated amino acids may be used, as well as amino acids having amine-containing side chains (such as Lys and Orn) in which the amine has been acylated or alkylated.

Examples of compounds of the invention include, but are not limited to:

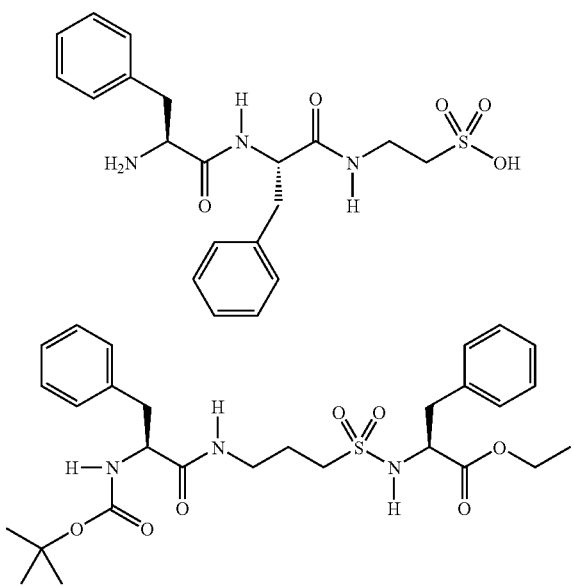

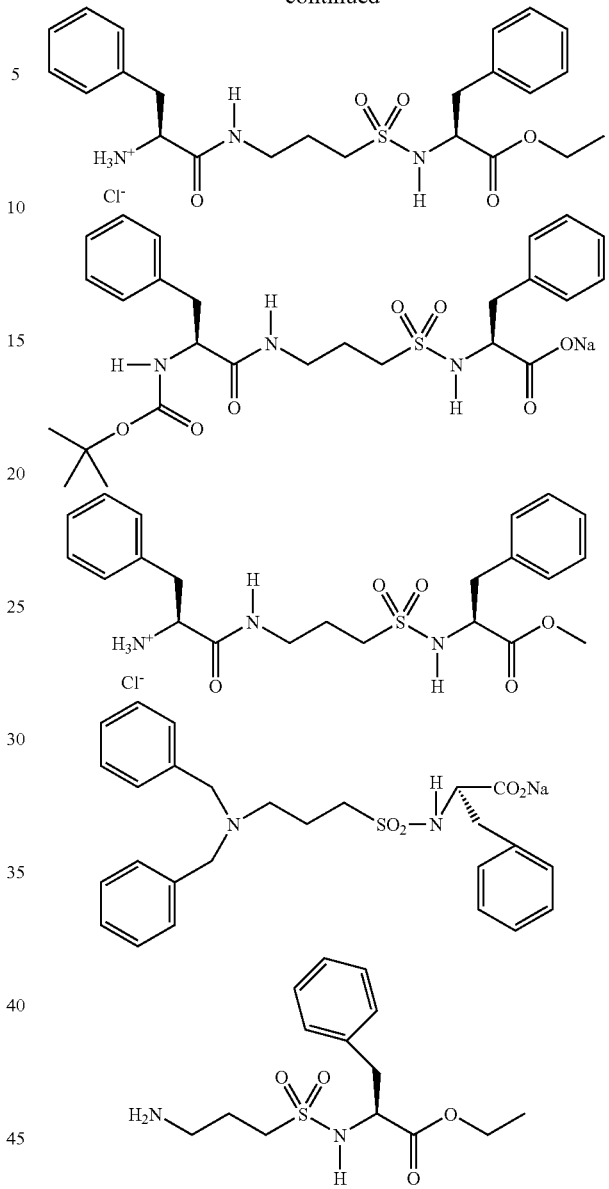

and pharmaceutically acceptable salts, esters, and prodrugs thereof.

In another embodiment, the invention pertains, at least in part, to compounds of Formula VI:

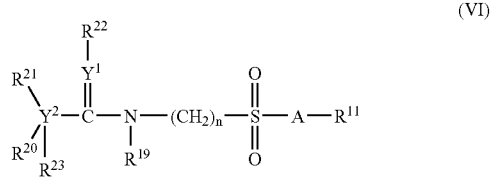

(VI)

wherein:
n is 1, 2, 3, 4, 5, 6, 7, 8, 9, or 10;
A is oxygen or nitrogen;

$R^{11}$ is hydrogen, salt-forming cation, ester forming group, —$(CH_2)_x$-Q, or when A is nitrogen, A and $R^{11}$ taken together may be the residue of a natural or unnatural amino acid or a salt or ester thereof;

Q is hydrogen, thiazolyl, triazolyl, imidazolyl, benzothiazolyl, or benzoimidazolyl;

x is 0, 1, 2, 3, or 4;

$R^{19}$ is hydrogen, alkyl or aryl;

$Y^1$ is oxygen, sulfur, or nitrogen;

$Y^2$ is carbon, nitrogen, or oxygen;

$R^{20}$ is hydrogen, alkyl, amino, mercaptoalkyl, alkenyl, alkynyl, cycloalkyl, aryl, arylalkyl, thiazolyl, triazolyl, tetrazolyl, imidazolyl, benzothiazolyl, or benzoimidazolyl;

$R^{21}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl, or absent if $Y^2$ is oxygen;

$R^{22}$ is hydrogen, alkyl, mercaptoalkyl, alkenyl, alkynyl, cycloalkyl, aryl, arylalkyl, thiazolyl, triazolyl, tetrazolyl, imidazolyl, benzothiazolyl, benzoimidazolyl; or $R^{22}$ is hydrogen, hydroxyl, alkoxy or aryloxy if $Y^1$ is nitrogen; or $R^{22}$ is absent if $Y^1$ is oxygen or sulfur; or $R^{22}$ and $R^{21}$ may be linked to form a cyclic moiety if $Y^1$ is nitrogen;

$R^{23}$ is hydrogen, alkyl, amino, mercaptoalkyl, alkenyl, alkynyl, cycloalkyl, aryl, arylalkyl, thiazolyl, triazolyl, tetrazolyl, imidazolyl, benzothiazolyl, or benzoimidazolyl, or absent if $Y^2$ is nitrogen or oxygen;

or pharmaceutically acceptable salts, esters, and prodrugs thereof.

In another embodiment, $R^{11}$ is a salt-forming cation. Examples of salt forming cations include pharmaceutically acceptable salts described herein as well as lithium, sodium, potassium, magnesium, calcium, barium, zinc, iron, and ammonium. In a further embodiment, the salt is a sodium salt. In a further, embodiment, A is oxygen.

In another embodiment, $Y^1$ is oxygen or sulfur, and $R^{22}$ is absent.

In another embodiment, $Y^2$ is oxygen and $R^{21}$ is absent. Examples of $R^{20}$ include benzyl, aryl (e.g., phenyl), alkyl, cycloalkyl (e.g., adamantyl), etc. In other embodiment, $Y^2$ is nitrogen and $R^{21}$ is hydrogen. In other embodiment, $R^{21}$ is benzyl. In another further embodiment, $R^{20}$ and $R^{21}$ are linked to form a pyridyl ring. In another embodiment, $Y^1$ is sulfur.

Other compounds of the invention include:

and pharmaceutically acceptable salts, esters, and prodrugs thereof.

Other compounds of the invention include:

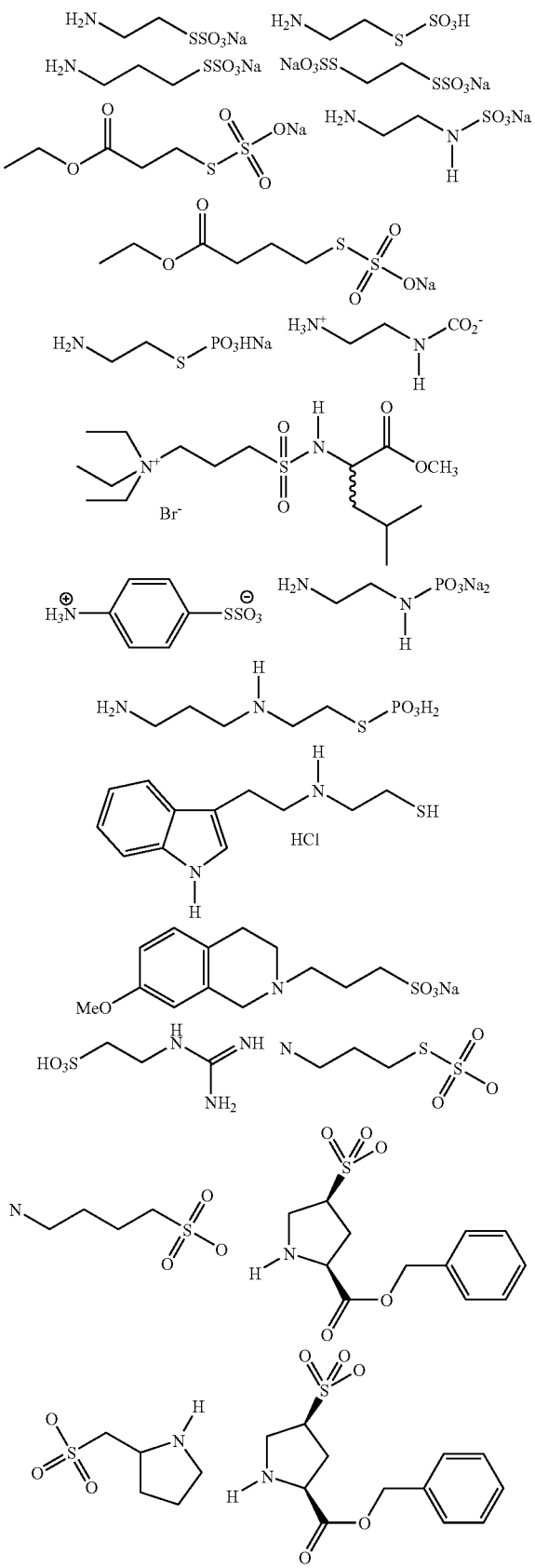

-continued

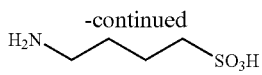

and pharmaceutically acceptable salts, prodrugs and esters thereof.

The invention pertains to both salt forms and acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein.

Compounds of the invention are also shown in Table 2 below.

TABLE 2

| ID | Structure/<br>Name of Compound |
|---|---|
| A | 5-phenyl-1-sulfopropyl-1,2,3,6-tetrahydropyridine |
| O | 3-(4-phenyl-1.2,3,6-tetrahydropyridin-1-yl)-1-propanesulfonic acid |
| T | 4-(4-cyclohex-3-enylpyridyl) butanesulfonic acid inner salt |
| U | N-[3-(4-benzyl-1-piperidyl)-1-propanesulfonyl]-L-leucine methyl ester |

TABLE 2-continued
| | |
|---|---|
| V | N-[3-(4-benzyl-1-piperazinyl)-1-propanesulfonyl]-L-leucine methyl ester |
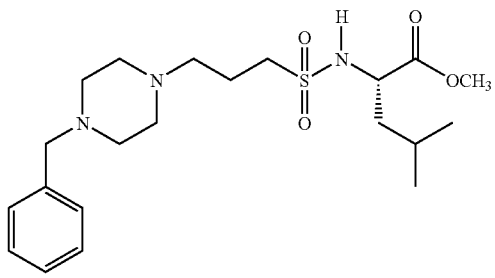
| | |
|---|---|
| AN | 3-((N-methylnicotinoyl)amino)-1-propanesulfonic acid, inner salt |
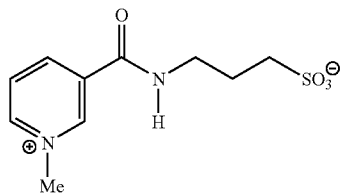
| | |
|---|---|
| AO | |
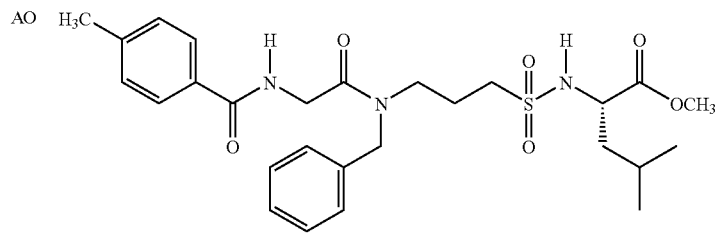
| | |
|---|---|
| AP | |
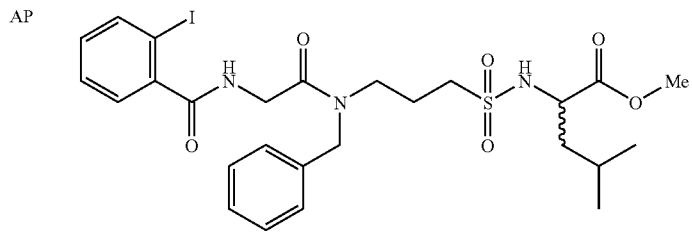
| | |
|---|---|
| AQ | |
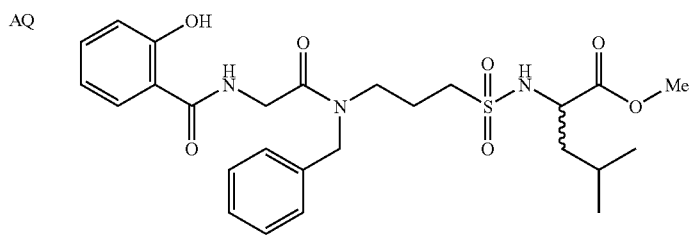
| | |
|---|---|
| AR | |
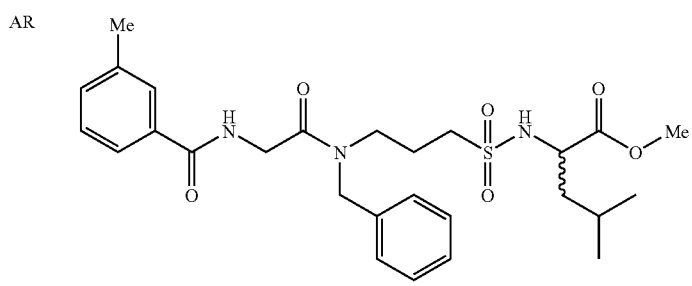

TABLE 2-continued
| | |
|---|---|
| AS | 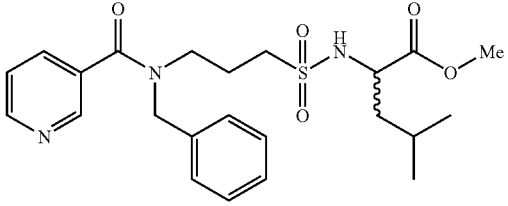 |
| AT | 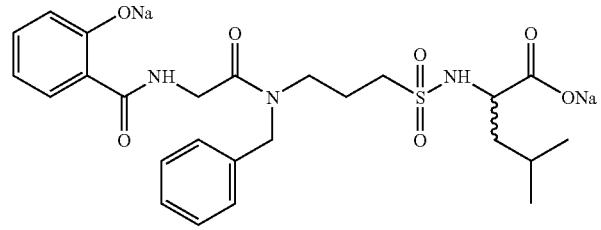 |
| BE | H$_2$N–CH$_2$CH$_2$–S–SO$_3$H |
| BF | H$_2$N–CH$_2$CH$_2$–SSO$_3$Na |
| BG | H$_2$N–CH$_2$CH$_2$CH$_2$–SSO$_3$Na |
| BH | NaO$_3$SS–CH$_2$CH$_2$–SSO$_3$Na |
| BI | H$_2$N–CH$_2$CH$_2$–NH–SO$_3$Na |
| BJ | H$_2$N–CH$_2$CH$_2$–NH–PO$_3$Na$_2$ |
| BK | H$_2$N–CH$_2$CH$_2$–S–PO$_3$HNa |
| BL | H$_2$N–CH$_2$CH$_2$CH$_2$–NH–CH$_2$CH$_2$–S–PO$_3$H$_2$ |
| BM | 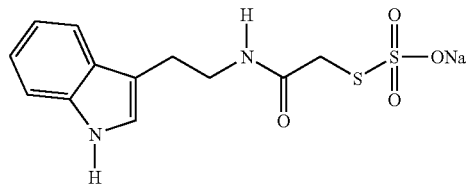 |
| BN | 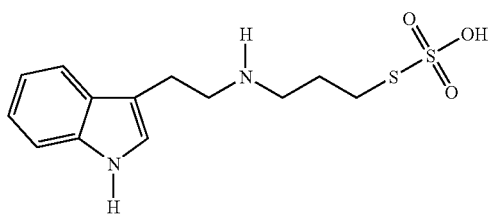 |

TABLE 2-continued

| | |
|---|---|
| BO | [structure: tryptamine-NH-C(O)-CH2CH2-S-SO2-ONa] |
| BP | [structure: tetrahydro-β-carboline-N-C(O)-CH2-S-SO2-ONa] |
| BQ | [2-(Ethoxycarbonyl)ethyl]-thiosulfonic acid, sodium salt<br>[structure: ethyl-O-C(O)-CH2CH2-S-SO2-ONa] |
| BR | [3-(Ethoxycarbonyl)propyl]-thiosulfonic acid, sodium salt<br>[structure: ethyl-O-C(O)-CH2CH2CH2-S-SO2-ONa] |
| BS | S-(2-{[2-(1-benzofuran-3-yl)ethyl]amino}-2-oxoethyl)thiosulfate, sodium salt<br>[structure: benzofuran-CH2CH2-NH-C(O)-CH2-S-SO2-ONa] |
| BT | 3-{[2-(3-indolyl)ethyl]-amino}-1-propanesulfonic acid<br>[structure: indole-CH2CH2-NH-CH2CH2CH2-SO3H] |
| BU | 3-(1,2,3,4-tetrahydro-1-naphthylamino)-1-propanesulfonic acid<br>[structure: caprolactam with NH-CH2CH2CH2-SO3Na substituent] |
| CA | 3-[(dl)-1-hydroxy-2-pentyl]amino-1-propane- sulfonic acid<br>[structure: HO-CH2-CH(propyl)-NH-CH2CH2CH2-SO3H] |

TABLE 2-continued

| | |
|---|---|
| CB | 4-amino-1-butanesulfonic acid |
| CF | 3-pentylamino-1-propanesulfonic acid |
| CQ | |
| CR | 4-Aminothiophenol-S-sulfate |
| CS | |
| CT | N-(beta-mercaptoethyl)tryptamine hydrochloride |
| CU | (S)-3-(1-hydroxy-2-butylamino)-1-propanesulfonic acid |
| CW | 3-(1-hydroxy-2-propylamino)-1-propanesulfonic acid |
| CX | 3-heptylamino-1-propane-sulfonic acid |
| CZ | 3-octylamino-1-propanesulfonic acid |

TABLE 2-continued

| | |
|---|---|
| DA | 3-nonylamino-1-propanesulfonic acid<br>$CH_3(CH_2)_8NH(CH_2)_3SO_3H$ |
| DB | $CH_3(CH_2)_9N^+(CH_3)_2(CH_2)_3SO_3^-$ |
| DF | $CH_3(CH_2)_{11}N^+(CH_3)_2(CH_2)_3SO_3^-$ |
| EU | (S)-3-(3-sulfopropylamino)-azepan-2-one, sodium salt |
| EX | 2-guanidinoethanesulfonic acid ($HO_3S$-CH$_2$CH$_2$-NH-C(=NH)NH$_2$) |
| FB | 3-((5-hydroxypentan-2-yl)amino)propane-1-sulfonic acid |
| FC | 3-(piperidin-1-yl)propane-1-sulfonic acid |
| FD | $CH_3(CH_2)_7N^+(CH_3)_2(CH_2)_3SO_3^-$ |
| FE | 3-(diethylamino)propane-1-sulfonic acid |
| FF | ethyl 2-phenyl-2-((3-sulfopropyl)amino)acetate |
| FG | 1-(4-(2-hydroxyethyl)piperazin-1-yl)-3-hydroxypropane-1-sulfonic acid (HOH$_2$CH$_2$C—N\_/N—CH$_2$CH(OH)CH$_2$SO$_3$H) |
| FJ | 3-(7-methoxy-3,4-dihydroisoquinolin-2(1H)-yl)propane-1-sulfonate sodium |
| FK | 2-((methylamino)methyl)benzenesulfonic acid |
| IQ | 2-(3-sulfonatopropyl)-9H-β-carbolin-2-ium |

TABLE 2-continued
| | |
|---|---|
| KD | 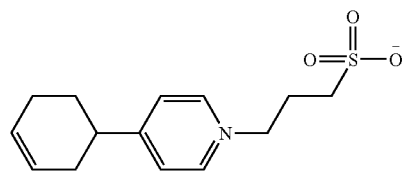 |
| KE | 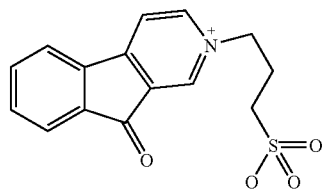 |
| KF | 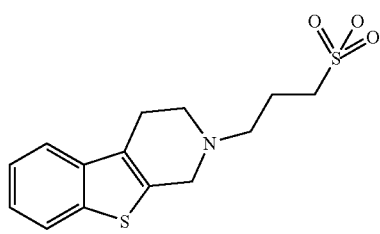 |
| KG | 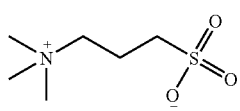 |
| KZ | 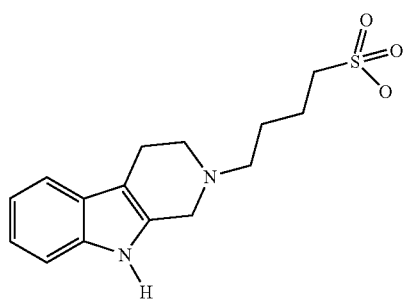 |
| LB | 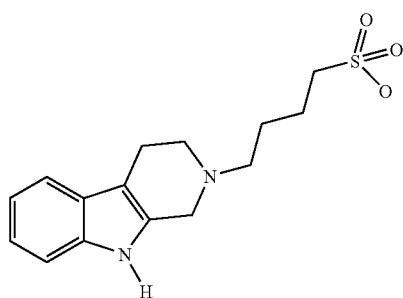 |
| LR | 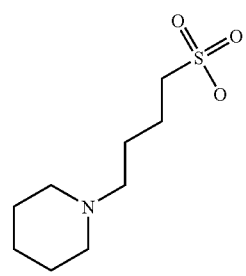 |

TABLE 2-continued
LS 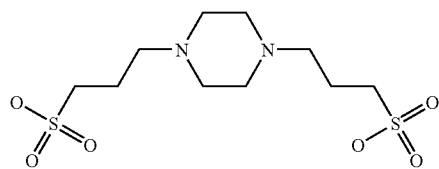
LT 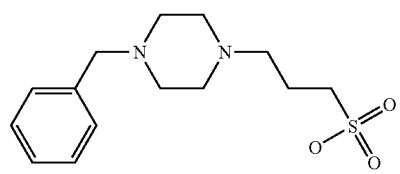
LU 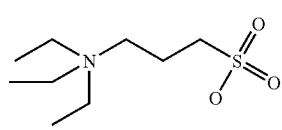
LV 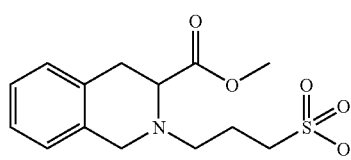
LW 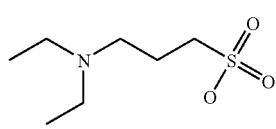
LX 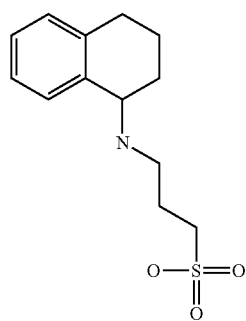
LY 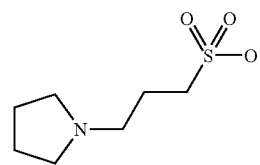
LZ 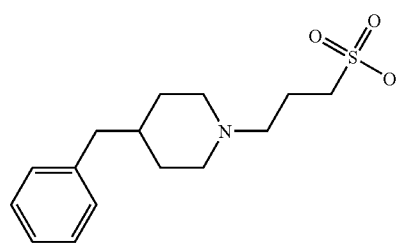

TABLE 2-continued
MA 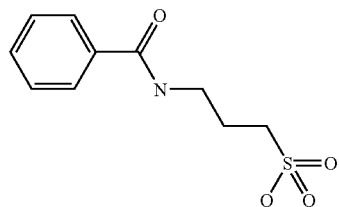
MB 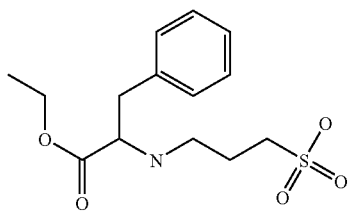
MC 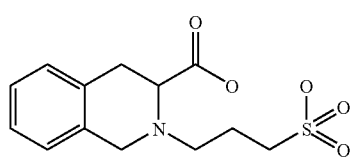
MD 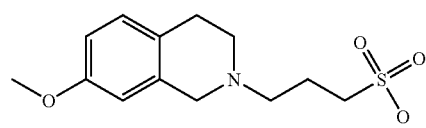
ME 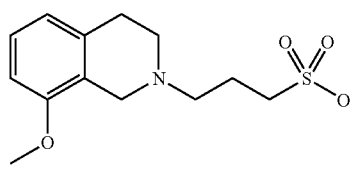
MF 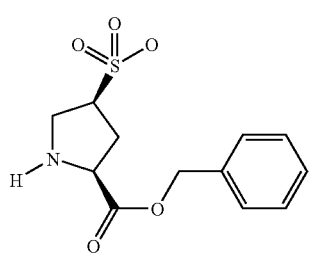
MG 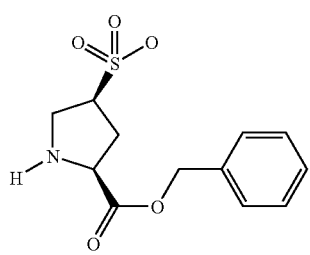
MH 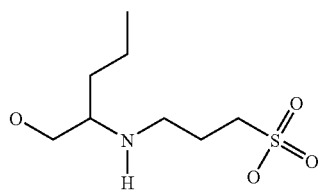

TABLE 2-continued
MI 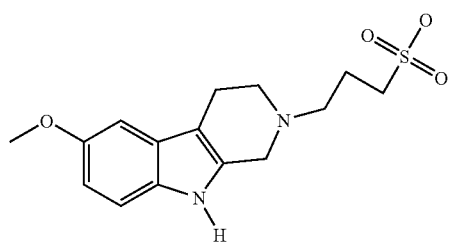
MJ 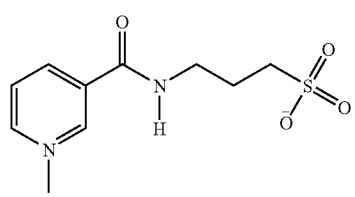
MK 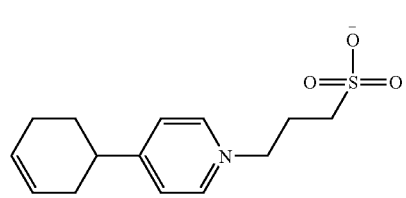
ML 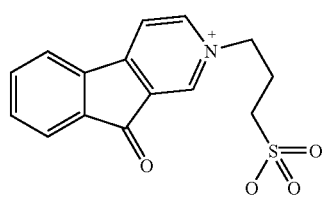
MM 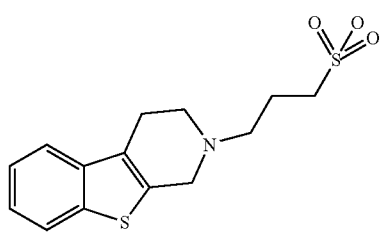
MN 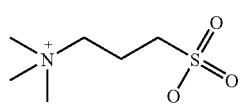
MO 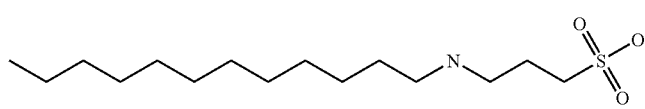
MP 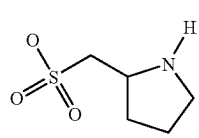
MQ 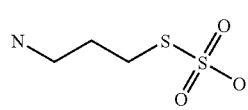

TABLE 2-continued
MR
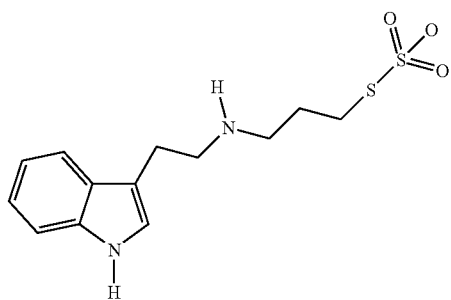
MS
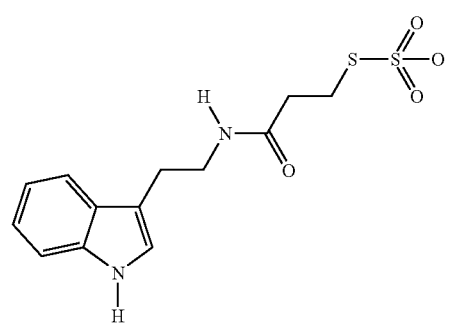
MT
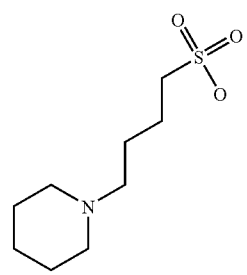
MU
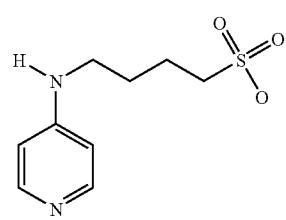
MV
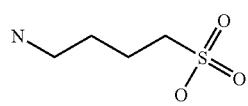
MW
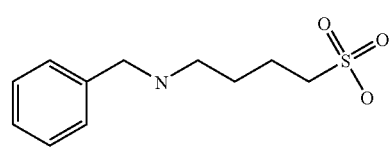

TABLE 2-continued

| | |
|---|---|
| MX | [structure: cyclohexenyl-pyridinium with propylsulfonate] |
| MY | [structure: long alkyl chain-N-propylsulfonate] |
| MZ | [structure: methoxy-tetrahydro-β-carboline with propylsulfonate] |
| NA | $CH_3(CH_2)_{13}N^+(CH_3)_2(CH_2)_3SO_3^-$ |
| NB | $CH_3(CH_2)_{15}N^+(CH_3)_2(CH_2)_3SO_3^-$ |

It should be noted that in the above table and throughout the application when an atom is shown with out hydrogens, but hydrogens are required or chemically necessary to form a stable compound, hydrogens should be inferred to be part of the compound.

In one embodiment, the invention does not pertain to the compounds described in WO 00/64420 and WO 96/28187. In this embodiment, the invention does not pertain to methods of using the compounds described in WO 00/64420 and WO 96/28187 for the treatment of diseases or disorders described therein. In a further embodiment, the invention pertains to methods of using the compounds described in WO 00/64420 and WO 96/28187 for methods described in this application, which are not described in WO 00/64420 and WO 96/28187. Both of WO 00/64420 and WO 96/28187 are incorporated by reference herein in their entirety.

It should be understood that the use of any of the compounds described herein or in the applications identified in "The Related Applications" Section is within the scope of the present invention and is intended to be encompassed by the present invention and is expressly incorporated herein at least for these purposes, and is furthermore expressly incorporated for all other purposes.

Subjects and Patient Populations

The term "subject" includes living organisms in which amyloidosis can occur, or which are susceptible to amyloid diseases, e.g., Alzheimer's disease, Down's syndrome, CAA, dialysis-related ($\beta_2$M) amyloidosis, secondary (AA) amyloidosis, primary (AL) amyloidosis, hereditary amyloidosis, diabetes, etc. Examples of subjects include humans, chickens, ducks, peking ducks, geese, deer, monkeys, cows, rabbits, sheep, goats, dogs, cats, mice, rats, and transgenic species thereof. Administration of the compositions of the present invention to a subject to be treated can be carried out using known procedures, at dosages and for periods of time effective to modulate amyloid aggregation or amyloid-induced toxicity in the subject as further described herein. An effective amount of the therapeutic compound necessary to achieve a therapeutic effect may vary according to factors such as the amount of amyloid already deposited at the clinical site in the subject, the age, sex, and weight of the subject, and the ability of the therapeutic compound to modulate amyloid aggregation in the subject. Dosage regimens can be adjusted to provide the optimum therapeutic response. For example, several divided doses may be administered daily or the dose may be proportionally reduced as indicated by the exigencies of the therapeutic situation.

In certain embodiments of the invention, the subject is in need of treatment by the methods of the invention, and is selected for treatment based on this need. A subject in need of treatment is art-recognized, and includes subjects that have been identified as having a disease or disorder related to amyloid-deposition or amyloidosis, has a symptom of such a disease or disorder, or is at risk of such a disease or disorder, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

In an exemplary aspect of the invention, the subject is a human. For example, the subject may be a human over 30 years old, human over 40 years old, a human over 50 years old, a human over 60 years old, a human over 70 years old, a human over 80 years old, a human over 85 years old, a human over 90 years old, or a human over 95 years old. The subject may be a female human, including a postmenopausal female human, who may be on hormone (estrogen) replacement therapy. The subject may also be a male human. In another embodiment, the subject is under 40 years old.

A subject may be a human at risk for Alzheimer's disease, e.g., being over the age of 40 or having a predisposition for Alzheimer's disease. Alzheimer's disease predisposing factors identified or proposed in the scientific literature include, among others, a genotype predisposing a subject to Alzheimer's disease; environmental factors predisposing a subject to Alzheimer's disease; past history of infection by viral and bacterial agents predisposing a subject to Alzheimer's disease; and vascular factors predisposing a subject to Alzheimer's disease. A subject may also have one or more risk factors for cardiovascular disease (e.g., atherosclerosis of the coronary arteries, angina pectoris, and myocardial infarction) or cerebrovascular disease (e.g., atherosclerosis of the intracranial or extracranial arteries, stroke, syncope, and transient ischemic attacks), such as hypercholesterolemia, hypertension, diabetes, cigarette smoking, familial or previous history of coronary artery disease, cerebrovascular disease, and cardiovascular disease. Hypercholesterolemia typically is defined as a serum total cholesterol concentration of greater than about 5.2 mmol/L (about 200 mg/dL).

Several genotypes are believed to predispose a subject to Alzheimer's disease. These include the genotypes such as presenilin-1, presenilin-2, and amyloid precursor protein (APP) missense mutations associated with familial Alzheimer's disease, and α-2-macroglobulin and LRP-1 genotypes, which are thought to increase the risk of acquiring sporadic (late-onset) Alzheimer's disease. E. van Uden, et al., *J. Neurosci.* 22(21), 9298-304 (2002); J. J. Goto, et al., J. Mol. Neurosci. 19(1-2), 37-41 (2002). Another genetic risk factor for the development of Alzheimer's disease are variants of ApoE, the gene that encodes apolipoprotein E (particularly the apoE4 genotype), a constituent of the low-density lipoprotein particle. W J Strittmatter, et al., *Annu. Rev. Neurosci.* 19, 53-77 (1996). The molecular mechanisms by which the various ApoE alleles alter the likelihood of developing Alzheimer's disease are unknown, however the role of ApoE in cholesterol metabolism is consistent with the growing body of evidence linking cholesterol metabolism to Alzheimer's disease. For example, chronic use of cholesterol-lowering drugs such as statins has recently been associated with a lower incidence of Alzheimer's disease, and cholesterol-lowering drugs have been shown to reduce pathology in APP transgenic mice. These and other studies suggest that cholesterol may affect APP processing. ApoE4 has been suggested to alter Aβ trafficking (in and out of the brain), and favor retention of Aβ in the brain. ApoE4 has also been suggested to favor APP processing toward Aβ formation. Environmental factors have been proposed as predisposing a subject to Alzheimer's disease, including exposure to aluminum, although the epidemiological evidence is ambiguous. In addition, prior infection by certain viral or bacterial agents may predispose a subject to Alzheimer's disease, including the herpes simplex virus and *chlamydia pneumoniae*. Finally, other predisposing factors for Alzheimer's disease can include risk factors for cardiovascular or cerebrovascular disease, including cigarette smoking, hypertension and diabetes. "At risk for Alzheimer's disease" also encompasses any other predisposing factors not listed above or as yet identified and includes an increased risk for Alzheimer's disease caused by head injury, medications, diet, or lifestyle.

The methods of the present invention can be used for one or more of the following: to prevent Alzheimer's disease, to treat Alzheimer's disease, or ameliorate symptoms of Alzheimer's disease, or to regulate production of or levels of amyloid β (Aβ) peptides. In an embodiment, the human carries one or more mutations in the genes that encode β-amyloid precursor protein, presenilin-1 or presenilin-2. In another embodiment, the human carries the Apolipoprotein ε4 gene. In another embodiment, the human has a family history of Alzheimer's Disease or a dementia illness. In another embodiment, the human has trisomy 21 (Down's Syndrome). In another embodiment, the subject has a normal or low serum total blood cholesterol level. In another embodiment, the serum total blood cholesterol level is less than about 200 mg/dL, or less than about 180, and it can range from about 150 to about 200 mg/dL. In another embodiment, the total LDL cholesterol level is less than about 100 mg/dL, or less than about 90 mg/dL and can range from about 30 to about 100 mg/dL. Methods of measuring serum total blood cholesterol and total LDL cholesterol are well known to those skilled in the art and for example include those disclosed in WO 99/38498 at p. 11, incorporated by reference herein. Methods of determining levels of other sterols in serum are disclosed in H. Gylling, et al., "Serum Sterols During Stanol Ester Feeding in a Mildly Hypercholesterolemic Population", *J. Lipid Res.* 40: 593-600 (1999).

In another embodiment, the subject has an elevated serum total blood cholesterol level. In another embodiment, the serum total cholesterol level is at least about 200 mg/dL, or at least about 220 mg/dL and can range from about 200 to about 1000 mg/dL. In another embodiment, the subject has an elevated total LDL cholesterol level. In another embodiment, the total LDL cholesterol level is greater than about 100 mg/dL, or even greater than about 110 mg/dL and can range from about 100 to about 1000 mg/dL.

In another embodiment, the human is at least about 40 years of age. In another embodiment, the human is at least about 60 years of age. In another embodiment, the human is at least about 70 years of age. In another embodiment, the human is at least about 80 years of age. In another embodiment, the human is at least about 85 years of age. In one embodiment, the human is between about 60 and about 100 years of age.

In still a further embodiment, the subject is shown to be at risk by a diagnostic brain imaging technique, for example, one that measures brain activity, plaque deposition, or brain atrophy.

In still a further embodiment, the subject is shown to be at risk by a cognitive test such as Clinical Dementia Rating ("CDR"), Alzheimer's Disease Assessment Scale-Cognition ("ADAS-Cog"), or Mini-Mental State Examination ("MMSE"). The subject may exhibit a below average score on a cognitive test, as compared to a historical control of similar age and educational background. The subject may also exhibit a reduction in score as compared to previous scores of the subject on the same or similar cognition tests.

In determining the CDR, a subject is typically assessed and rated in each of six cognitive and behavioural categories: memory, orientation, judgment and problem solving, community affairs, home and hobbies, and personal care. The assessment may include historical information provided by the subject, or preferably, a corroborator who knows the subject well. The subject is assessed and rated in each of these areas and the overall rating, (0, 0.5, 1.0, 2.0 or 3.0) determined. A rating of 0 is considered normal. A rating of 1.0 is considered to correspond to mild dementia. A subject with a CDR of 0.5 is characterized by mild consistent forgetfulness, partial recollection of events and "benign" forgetfulness. In one embodiment the subject is assessed with a rating on the CDR of above 0, of above about 0.5, of above about 1.0, of above about 1.5, of above about 2.0, of above about 2.5, or at about 3.0.

Another test is the Mini-Mental State Examination (MMSE), as described by Folstein "Mini-mental state. A practical method for grading the cognitive state of patients for the clinician." J. Psychiatr. Res. 12:189-198, 1975. The MMSE evaluates the presence of global intellectual deterioration. See also Folstein "Differential diagnosis of dementia. The clinical process." Psychiatr Clin North Am. 20:45-57, 1997. The MMSE is a means to evaluate the onset of dementia and the presence of global intellectual deterioration, as seen in Alzheimer's disease and multi-infart dementia. The MMSE is scored from 1 to 30. The MMSE does not evaluate basic cognitive potential, as, for example, the so-called IQ test. Instead, it tests intellectual skills. A person of "normal" intellectual capabilities will score a "30" on the MMSE objective test (however, a person with a MMSE score of 30 could also score well below "normal" on an IQ test). See, e.g., Kaufer, J. Neuropsychiatry Clin. Neurosci. 10:55-63, 1998; Becke, Alzheimer Dis Assoc Disord. 12:54-57, 1998; Ellis, Arch. Neurol. 55:360-365, 1998; Magni, Int. Psychogeriatr. 8:127-134, 1996; Monsch, Acta Neurol. Scand. 92:145-150, 1995. In one embodiment, the subject scores below 30 at least once on the MMSE. In another embodiment, the subject scores below about 28, below about 26, below about 24, below about 22, below about 20, below about 18, below about 16, below about 14, below about 12, below about 10, below about 8, below about 6, below about 4, below about 2, or below about 1.

Another means to evaluate cognition, particularly Alzheimer's disease, is the Alzheimer's Disease Assessment Scale (ADAS-Cog), or a variation termed the Standardized Alzheimer's Disease Assessment Scale (SADAS). It is commonly used as an efficacy measure in clinical drug trials of Alzheimer's disease and related disorders characterized by cognitive decline. SADAS and ADAS-Cog were not designed to diagnose Alzheimer's disease; they are useful in characterizing symptoms of dementia and are a relatively sensitive indicator of dementia progression. (See, e.g., Doraiswamy, Neurology 48:1511-1517, 1997; and Standish, J. Am. Geriatr. Soc. 44:712-716, 1996.) Annual deterioration in untreated Alzheimer's disease patients is approximately 8 points per year (See, eg., Raskind, M Prim. Care Companion J Clin Psychiatry 2000 August; 2(4):134-138).

The ADAS-cog is designed to measure, with the use of questionnaires, the progression and the severity of cognitive decline as seen in Aβ on a 70-point scale. The ADAS-cog scale quantifies the number of wrong answers. Consequently, a high score on the scale indicates a more severe case of cognitive decline. In one embodiment, a subject exhibits a score of greater than 0, greater than about 5, greater than about 10, greater than about 15, greater than about 20, greater than about 25, greater than about 30, greater than about 35, greater than about 40, greater than about 45, greater than about 50, greater than about 55, greater than about 60, greater than about 65, greater than about 68, or about 70.

In another embodiment, the subject exhibits no symptoms of Alzheimer's Disease. In another embodiment, the subject is a human who is at least 40 years of age and exhibits no symptoms of Alzheimer's Disease. In another embodiment, the subject is a human who is at least 40 years of age and exhibits one or more symptoms of Alzheimer's Disease.

In another embodiment, the subject has Mild Cognitive Impairment. In a further embodiment, the subject has a CDR rating of about 0.5. In another embodiment, the subject has early Alzheimer's disease. In another embodiment, the subject has cerebral amyloid angiopathy.

By using the methods of the present invention, the levels of amyloid β peptides in a subject's plasma or cerebrospinal fluid (CSF) can be reduced from levels prior to treatment from about 10 to about 100 percent, or even about 50 to about 100 percent.

In an alternative embodiment, the subject can have an elevated level of amyloid $A\beta_{40}$ and $A\beta_{42}$ peptide in the blood and CSF prior to treatment, according to the present methods, of greater than about 10 pg/mL, or greater than about 20 pg/mL, or greater than about 35 pg/mL, or even greater than about 40 pg/mL. In another embodiment, the elevated level of amyloid $A\beta_{42}$ peptide can range from about 30 pg/mL to about 200 pg/mL, or even to about 500 pg/mL. One skilled in the art would understand that as Alzheimer's disease progresses, the measurable levels of amyloid β peptide in the CSF may decrease from elevated levels present before onset of the disease. This effect is attributed to increased deposition, i.e., trapping of Aβ peptide in the brain instead of normal clearance from the brain into the CSF.

In an alternative embodiment, the subject can have an elevated level of amyloid $A\beta_{40}$ peptide in the blood and CSF prior to treatment, according to the present methods, of greater than about 5 pg $A\beta_{42}$/mL or greater than about 50 pg $A\beta_{40}$/mL, or greater than about 400 pg/mL. In another embodiment, the elevated level of amyloid $A\beta_{40}$ peptide can range from about 200 pg/mL to about 800 pg/mL, to even about 1000 pg/mL.

In another embodiment, the subject can have an elevated level of amyloid $A\beta_{42}$ peptide in the CSF prior to treatment, according to the present methods, of greater than about 5 pg/mL, or greater than about 10 pg/mL, or greater than about 200 pg/mL, or greater than about 500 pg/mL. In another embodiment, the level of amyloid β peptide can range from about 10 pg/mL to about 1,000 pg/mL, or even about 100 pg/mL to about 1,000 pg/mL.

In another embodiment, the subject can have an elevated level of amyloid $A\beta_{40}$ peptide in the CSF prior to treatment according to the present methods of greater than about 10 pg/mL, or greater than about 50 pg/mL, or even greater than about 100 pg/mL. In another embodiment, the level of amyloid β peptide can range from about 10 pg/mL to about 1,000 pg/mL.

The amount of amyloid β peptide in the brain, CSF, blood, or plasma of a subject can be evaluated by enzyme-linked immunosorbent assay ("ELISA") or quantitative immunoblotting test methods or by quantitative SELDI-TOF which are well known to those skilled in the art, such as is disclosed by Zhang, et al., *J. Biol. Chem.* 274, 8966-72 (1999) and Zhang, et al., *Biochemistry* 40, 5049-55 (2001). See also, A. K. Vehmas, et al., *DNA Cell Biol.* 20(11), 713-21 (2001), P. Lewczuk, et al., *Rapid Commun. Mass Spectrom.* 17(12), 1291-96 (2003); B. M. Austen, et al., *J. Peptide Sci.* 6, 459-69 (2000); and H. Davies, et al., *BioTechniques* 27, 1258-62 (1999). These tests are performed on samples of the brain or blood which have been prepared in a manner well known to one skilled in the art. Another example of a useful method for measuring levels of amyloid β peptides is by Europium immunoassay (EIA). See, e.g., WO 99/38498 at p. 11.

The methods of the invention may be applied as a therapy for a subject having Alzheimer's disease or a dementia, or the methods of the invention may be applied as a prophylaxis against Alzheimer's disease or dementia for subject with such a predisposition, as in a subject, e.g., with a genomic mutation in the APP gene, the ApoE gene, or a presenilin gene. The subject may have (or may be predisposed to developing or may be suspected of having) vascular dementia, or senile dementia, Mild Cognitive Impairment, or early Alzheimer's disease. In addition to Alzheimer's disease, the subject may have another amyloid-related disease such as cerebral amyloid angiopathy, or the subject may have amyloid deposits, especially amyloid-β amyloid deposits in the brain.

Treatment of Amyloid-Related Diseases

The present invention pertains to methods of using the compounds and pharmaceutical compositions thereof in the treatment and prevention of amyloid-related diseases. The pharmaceutical compositions of the invention may be administered therapeutically or prophylactically to treat diseases associated with amyloid (e.g., AL amyloid protein (λ or κ-chain related, e.g., amyloid λ, amyloid κ, amyloid κIV, amyloid λVI, amyloid γ, amyloid γl), Aβ, IAPP, β$_2$M, AA, or AH amyloid protein) fibril formation, aggregation or deposition.

The pharmaceutical compositions of the invention may act to ameliorate the course of an amyloid-related disease using any of the following mechanisms (this list is meant to be illustrative and not limiting): slowing the rate of amyloid fibril formation or deposition; lessening the degree of amyloid deposition; inhibiting, reducing, or preventing amyloid fibril formation; inhibiting neurodegeneration or cellular toxicity induced by amyloid; inhibiting amyloid induced inflammation; enhancing the clearance of amyloid from the brain; enhancing degradation of Aβ in the brain; or favoring clearance of amyloid protein prior to its organization in fibrils.

"Modulation" of amyloid deposition includes both inhibition, as defined above, and enhancement of amyloid deposition or fibril formation. The term "modulating" is intended, therefore, to encompass prevention or stopping of amyloid formation or accumulation, inhibition or slowing down of further amyloid formation or accumulation in a subject with ongoing amyloidosis, e.g., already having amyloid deposition, and reducing or reversing of amyloid formation or accumulation in a subject with ongoing amyloidosis; and enhancing amyloid deposition, e.g., increasing the rate or amount of amyloid deposition in vivo or in vitro. Amyloid-enhancing compounds may be useful in animal models of amyloidosis, for example, to make possible the development of amyloid deposits in animals in a shorter period of time or to increase amyloid deposits over a selected period of time. Amyloid-enhancing compounds may be useful in screening assays for compounds which inhibit amyloidosis in vivo, for example, in animal models, cellular assays and in vitro assays for amyloidosis. Such compounds may be used, for example, to provide faster or more sensitive assays for compounds. Modulation of amyloid deposition is determined relative to an untreated subject or relative to the treated subject prior to treatment.

"Inhibition" of amyloid deposition includes preventing or stopping of amyloid formation, e.g., fibrillogenesis, clearance of amyloid, e.g., soluble Aβ from brain, inhibiting or slowing down of further amyloid deposition in a subject with amyloidosis, e.g., already having amyloid deposits, and reducing or reversing amyloid fibrillogenesis or deposits in a subject with ongoing amyloidosis. Inhibition of amyloid deposition is determined relative to an untreated subject, or relative to the treated subject prior to treatment, or, e.g., determined by clinically measurable improvement, e.g., or in the case of a subject with brain amyloidosis, e.g., an Alzheimer's or cerebral amyloid angiopathy subject, stabilization of cognitive function or prevention of a further decrease in cognitive function (i.e., preventing, slowing, or stopping disease progression), or improvement of parameters such as the concentration of Aβ or tau in the CSF.

As used herein, "treatment" of a subject includes the application or administration of a composition of the invention to a subject, or application or administration of a composition of the invention to a cell or tissue from a subject, who has an amyloid-related disease or condition, has a symptom of such a disease or condition, or is at risk of (or susceptible to) such a disease or condition, with the purpose of curing, healing, alleviating, relieving, altering, remedying, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination, a psychiatric evaluation, or a cognition test such as CDR, MMSE, ADAS-Cog, or another test known in the art. For example, the methods of the invention successfully treat a subject's dementia by slowing the rate of or lessening the extent of cognitive decline.

In one embodiment, the term "treating" includes maintaining a subject's CDR rating at its base line rating or at 0. In another embodiment, the term treating includes decreasing a subject's CDR rating by about 0.25 or more, about 0.5 or more, about 1.0 or more, about 1.5 or more, about 2.0 or more, about 2.5 or more, or about 3.0 or more. In another embodiment, the term "treating" also includes reducing the rate of the increase of a subject's CDR rating as compared to historical controls. In another embodiment, the term includes reducing the rate of increase of a subject's CDR rating by about 5% or more, about 10% or more, about 20% or more, about 25% or more, about 30% or more, about 40% or more, about 50% or more, about 60% or more, about 70% or more, about 80% or more, about 90% or more, or about 100%, of the increase of the historical or untreated controls.

In another embodiment, the term "treating" also includes maintaining a subject's score on the MMSE. The term "treating" includes increasing a subject's MMSE score by about 1, about 2, about 3, about 4, about 5, about 7.5, about 10, about 12.5, about 15, about 17.5, about 20, or about 25 points. The term also includes reducing the rate of the decrease of a subject's MMSE score as compared to historical controls. In another embodiment, the term includes reducing the rate of decrease of a subject's MMSE score by about 5% or less, about 10% or less, about 20% or less, about 25% or less, about 30% or less, about 40% or less, about 50% or less, about 60% or less, about 70% or less, about 80% or less, about 90% or less or about 100% or less, of the decrease of the historical or untreated controls.

In yet another embodiment, the term "treating" includes maintaining a subject's score on the ADAS-Cog. The term "treating" includes decreasing a subject's ADAS-Cog score by about 1 point or greater, by about 2 points or greater, by about 3 points or greater, by about 4 points or greater, by about 5 points or greater, by about 7.5 points or greater, by about 10 points or greater, by about 12.5 points or greater, by about 15 points or greater, by about 17.5 points or greater, by about 20 points or greater, or by about 25 points or greater. The term also includes reducing the rate of the increase of a subject's ADAS-Cog score as compared to historical controls. In another embodiment, the term includes reducing the rate of increase of a subject's ADAS-Cog score by about 5% or more, about 10% or more, about 20% or more, about 25% or more, about 30% or more, about 40% or more, about 50% or more, about 60% or more, about 70% or more, about 80% or more, about 90% or more or about 100% of the increase of the historical or untreated controls.

In another embodiment, the term "treating" e.g., for AA or AL amyloidosis, includes an increase in serum creatinine, e.g., an increase of creatinine clearance of 10% or greater, 20% or greater, 50% or greater, 80% or greater, 90% or greater, 100% or greater, 150% or greater, 200% or greater. The term "treating" also may induce remission of nephrotic syndrome (NS). It may also include remission of chronic diarrhea and/or a gain in body weight, e.g., by 10% or greater, 15% or greater, or 20% or greater.

Without wishing to be bound by theory, in some aspects the pharmaceutical compositions of the invention contain a compound that prevents or inhibits amyloid fibril formation, either in the brain or other organ of interest (acting locally) or throughout the entire body (acting systemically). Pharmaceutical compositions of the invention may be effective in controlling amyloid deposition either following their entry into the brain (following penetration of the blood brain barrier) or from the periphery. When acting from the periphery, a compound of a pharmaceutical composition may alter the equilibrium of amyloidogenic peptide between the brain and the plasma so as to favor the exit of amyloidogenic peptide from the brain. It may also favor clearance (or catabolism) of the amyloid protein (soluble), and then prevent amyloid fibril formation and deposition due to a reduction of the amyloid protein pool in a specific organ, e.g., liver, spleen, pancreas, kidney, joints, brain, etc. An increase in the exit of amyloidogenic peptide from the brain would result in a decrease in amyloidogenic peptide brain concentration and therefore favor a decrease in amyloidogenic peptide deposition. In particular, an agent may lower the levels of amyloid β peptides, e.g., both Aβ40 and Aβ42 in the CSF and the plasma, or the agent may lower the levels of amyloid β peptides, e.g., Aβ40 and Aβ42 in the CSF and increase it in the plasma. Alternatively, compounds that penetrate the brain could control deposition by acting directly on brain amyloidogenic peptide e.g., by maintaining it in a non-fibrillar form or favoring its clearance from the brain, by increasing its degradation in the brain, or protecting brain cells from the detrimental effect of amyloidogenic peptide. An agent can also cause a decrease of the concentration of the amyloid protein (i.e., in a specific organ so that the critical concentration needed to trigger amyloid fibril formation or deposition is not reached). Furthermore, the compounds described herein may inhibit or reduce an interaction between amyloid and a cell surface constituent, for example, a glycosaminoglycan or proteoglycan constituent of a basement membrane, whereby inhibiting or reducing this interaction produces the observed neuroprotective and cell-protective effects. For example, the compound may also prevent an amyloid peptide from binding or adhering to a cell surface, a process which is known to cause cell damage or toxicity. Similarly, the compound may block amyloid-induced cellular toxicity or microglial activation or amyloid-induced neurotoxicity, or inhibit amyloid induced inflammation. The compound may also reduce the rate or amount of amyloid aggregation, fibril formation, or deposition, or the compound lessens the degree of amyloid deposition. The foregoing mechanisms of action should not be construed as limiting the scope of the invention inasmuch as the invention may be practiced without such information.

The term "amyloid-β disease" (or "amyloid-β related disease," which terms as used herein are synonymous) may be used for mild cognitive impairment; vascular dementia; early Alzheimer's disease; Alzheimer's disease, including sporadic (non-hereditary) Alzheimer's disease and familial (hereditary) Alzheimer's disease; age-related cognitive decline; cerebral amyloid angiopathy ("CAA"); hereditary cerebral hemorrhage; senile dementia; Down's syndrome; inclusion body myositis ("IBM"); or age-related macular degeneration ("ARMD"). According to certain aspects of the invention, amyloid-β is a peptide having 39-43 amino-acids, or amyloid-β is an amyloidogenic peptide produced from βAPP.

Mild cognitive impairment ("MCI") is a condition characterized by a state of mild but measurable impairment in thinking skills, which is not necessarily associated with the presence of dementia. MCI frequently, but not necessarily, precedes Alzheimer's disease. It is a diagnosis that has most often been associated with mild memory problems, but it can also be characterized by mild impairments in other thinking skills, such as language or planning skills. However, in general, an individual with MCI will have more significant memory lapses than would be expected for someone of their age or educational background. As the condition progresses, a physician may change the diagnosis to "Mild-to-Moderate Cognitive Impairment," as is well understood in this art.

Cerebral amyloid angiopathy ("CAA") refers to the specific deposition of amyloid fibrils in the walls of leptomingeal and cortical arteries, arterioles and in capillaries and veins. It is commonly associated with Alzheimer's disease, Down's syndrome and normal aging, as well as with a variety of familial conditions related to stroke or dementia (see Frangione, et al., *Amyloid: J. Protein Folding Disord.* 8, Suppl. 1, 36-42 (2001)). CAA can occur sporadically or be hereditary. Multiple mutation sites in either Aβ or the APP gene have been identified and are clinically associated with either dementia or cerebral hemorrhage. Exemplary CAA disorders include, but are not limited to, hereditary cerebral hemorrhage with amyloidosis of Icelandic type (HCHWA-I); the Dutch variant of HCHWA (HCHWA-D; a mutation in Aβ); the Flemish mutation of Aβ; the Arctic mutation of Aβ; the Italian mutation of Aβ; the Iowa mutation of Aβ; familial British dementia; and familial Danish dementia. Cerebral amyloid angiopathy is known to be associated with cerebral hemorrhage (or hemorrhagic stroke).

Additionally, abnormal accumulation of APP and of amyloid-β protein in muscle fibers has been implicated in the pathology of sporadic inclusion body myositis ("IBM") (Askanas, et al., *Proc. Natl. Acad. Sci. USA* 93, 1314-19 (1996); Askanas, et al., *Current Opinion in Rheumatology* 7, 486-96 (1995)). Accordingly, the compounds of the invention can be used prophylactically or therapeutically in the treatment of disorders in which amyloid-β protein is abnormally deposited at non-neurological locations, such as treatment of IBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration (ARMD). ARMD is a cause of irreversible vision loss in older individuals. It is believed that Aβ deposition could be an important component of the local inflammatory events that contribute to atrophy of the retinal pigmented epithelium, drusen biogenesis, and the pathogenesis of ARMD (Johnson, et al., *Proc. Natl. Acad. Sci. USA* 99(18), 11830-5 (2002)). Therefore, the invention also relates to the treatment or prevention of age-related macular degeneration.

Also, the invention relates to a method for preventing or inhibiting amyloid deposition in a subject. For example, such a method comprises administering to a subject a therapeutically effective amount of a compound capable of reducing the concentration of amyloid (e.g., AL amyloid protein (λ or κ-chain related, e.g., amyloid λ, amyloid κ, amyloid κIV, amyloid λVI, amyloid γ, amyloid γl), Aβ, IAPP, β$_2$M, AA, AH amyloid protein, or other amyloids), such that amyloid accumulation or deposition is prevented or inhibited.

In another aspect, the invention relates to a method for preventing, reducing, or inhibiting amyloid deposition in a subject. For example, such a method comprises administering to a subject a therapeutically effective amount of a compound capable of inhibiting amyloid (e.g., AL amyloid protein (λ or κ-chain related, e.g., amyloid λ, amyloid κ, amyloid κIV, amyloid λVI, amyloid γ, amyloid γl), Aβ, IAPP, β$_2$M, AA, AH amyloid protein, or other amyloids), such that amyloid deposition is prevented, reduced, or inhibited.

The invention also relates to a method for modulating, e.g., minimizing, amyloid-associated damage to cells, comprising the step of administering a compound capable of reducing the concentration of amyloid (e.g., AL amyloid protein (λ or κ-chain related, e.g., amyloid λ, amyloid κ, amyloid κIV, amyloid λVI, amyloid γ, amyloid γl), Aβ, IAPP, β$_2$M, AA, AH amyloid protein, or another amyloid), such that said amyloid-associated damage to cells is modulated. In certain aspects of the invention, the methods for modulating amyloid-associated damage to cells comprise a step of administering a compound capable of reducing the concentration of amyloid or reducing the interaction of an amyloid with a cell surface.

The invention also includes a method for directly or indirectly preventing cell death in a subject, the method comprising administering to a subject a therapeutically effective amount of a compound capable of preventing amyloid (e.g., AL amyloid protein (λ or κ-chain related, e.g., amyloid λ, amyloid κ, amyloid κIV, amyloid λVI, amyloid γ, amyloid γl), Aβ, IAPP, β$_2$M, AA, AH amyloid protein, or other amyloid) mediated events that lead, directly or indirectly, to cell death.

In an embodiment, the method is used to treat Alzheimer's disease (e.g. sporadic or familial AD). The method can also be used prophylactically or therapeutically to treat other clinical occurrences of amyloid-β deposition, such as in Down's syndrome individuals and in patients with cerebral amyloid angiopathy ("CAA") or hereditary cerebral hemorrhage.

The compounds of the invention may be used prophylactically or therapeutically in the treatment of disorders in which amyloid-beta peptide is abnormally deposited at non-neurological locations, such as treatment of IBM by delivery of the compounds to muscle fibers, or treatment of macular degeneration by delivery of the compound(s) of the invention to the basal surface of the retinal pigmented epithelium.

The present invention also provides a method for modulating amyloid-associated damage to cells, comprising the step of administering a compound capable of reducing the concentration of Aβ, or capable of minimizing the interaction of Aβ (soluble oligomeric or fibrillary) with the cell surface, such that said amyloid-associated damage to cells is modulated. In certain aspects of the invention, the methods for modulating amyloid-associated damage to cells comprise a step of administering a compound capable of reducing the concentration of Aβ or reducing the interaction of Aβ with a cell surface.

In accordance with the present invention, there is further provided a method for preventing cell death in a subject, said method comprising administering to a subject a therapeutically effective amount of a compound capable of preventing Aβ-mediated events that lead, directly or indirectly, to cell death.

The present invention also provides a method for modulating amyloid-associated damage to cells, comprising the step of administering a compound capable of reducing the concentration of IAPP, or capable of minimizing the interaction of IAPP (soluble oligomeric or fibrillary) with the cell surface, such that said amyloid-associated damage to cells is modulated. In certain aspects of the invention, the methods for modulating amyloid-associated damage to cells comprise a step of administering a compound capable of reducing the concentration of IAPP or reducing the interaction of IAPP with a cell surface.

In accordance with the present invention, there is further provided a method for preventing cell death in a subject, said method comprising administering to a subject a therapeutically effective amount of a compound capable of preventing IAPP-mediated events that lead, directly or indirectly, to cell death.

This invention also provides methods and compositions which are useful in the treatment of amyloidosis. The methods of the invention involve administering to a subject a therapeutic compound which inhibits amyloid deposition. Accordingly, the compositions and methods of the invention are useful for inhibiting amyloidosis in disorders in which amyloid deposition occurs. The methods of the invention can be used therapeutically to treat amyloidosis or can be used prophylactically in a subject susceptible to (hereditary) amyloidosis or identified as being at risk to develop amyloidosis, e.g., hereditary, or identified as being at risk to develop amyloidosis. In certain embodiments, the invention includes a method of inhibiting an interaction between an amyloidogenic protein and a constituent of basement membrane to inhibit amyloid deposition. The constituent of basement membrane is a glycoprotein or proteoglycan, preferably heparan sulfate proteoglycan. A therapeutic compound used in this method may interfere with binding of a basement membrane constituent to a target binding site on an amyloidogenic protein, thereby inhibiting amyloid deposition.

In some aspects, the methods of the invention involve administering to a subject a therapeutic compound which inhibits amyloid deposition. "Inhibition of amyloid deposition," includes the prevention of amyloid formation, inhibition of further amyloid deposition in a subject with ongoing amyloidosis and reduction of amyloid deposits in a subject with ongoing amyloidosis. Inhibition of amyloid deposition is determined relative to an untreated subject or relative to the treated subject prior to treatment. In an embodiment, amyloid deposition is inhibited by inhibiting an interaction between an amyloidogenic protein and a constituent of basement membrane. "Basement membrane" refers to an extracellular matrix comprising glycoproteins and proteoglycans, including laminin, collagen type IV, fibronectin, perlecan, agrin, dermatan sulfate, and heparan sulfate proteoglycan (HSPG). In one embodiment, amyloid deposition is inhibited by interfering with an interaction between an amyloidogenic protein and a sulfated glycosaminoglycan such as HSPG, dermatan sulfate, perlecan or agrin sulfate. Sulfated glycosaminoglycans are known to be present in all types of amyloids (see Snow, et al. Lab. Invest. 56, 120-23 (1987)) and amyloid deposition and HSPG deposition occur coincidentally in animal models of amyloidosis (see Snow, et al. Lab. Invest. 56, 665-75 (1987) and Gervais, F. et al. *Curr. Med. Chem.*, 3, 361-370 (2003)). Consensus binding site motifs for HSPG in amyloidogenic proteins have been described (see, e.g., Cardin and Weintraub Arteriosclerosis 9, 21-32 (1989)).

The ability of a compound to prevent or block the formation or deposition of amyloid may reside in its ability to bind to non-fibrillar, soluble amyloid protein and to maintain its solubility.

The ability of a therapeutic compound of the invention to inhibit an interaction between an amyloidogenic protein and a glycoprotein or proteoglycan constituent of a basement membrane can be assessed by an in vitro binding assay, such as that described in U.S. Pat. No. 5,164,295, the contents of which are hereby incorporated by reference. Alternatively, the ability of a compound to bind to an amyloidogenic protein or to inhibit the binding of a basement membrane constituent (e.g. HSPG) to an amyloidogenic protein (e.g. Aβ) can be measured using a mass spectrometry assay where soluble protein, e.g. Aβ, IAPP, β$_2$M is incubated with the compound. A compound which binds to, e.g. Aβ, will induce a change in the mass spectrum of the protein. Exemplary protocols for a mass spectrometry assay employing Aβ and IAPP can be found in the Examples, the results of which are provided in Table 3. The protocol can readily be modified to adjust the sensitivity of the data, e.g., by adjusting the amount of protein and/or compound employed. Thus, e.g., binding might be detected for test compounds noted as not having detectable binding employing less sensitive test protocols.

Alternative methods for screening compounds exist and can readily be employed by a skilled practitioner to provide an indication of the ability of test compounds to bind to, e.g., fibrillar Aβ. One such screening assay is an ultraviolet absorption assay. In an exemplary protocol, a test compound (20 μM) is incubated with 50 μM Aβ (1-40) fibers for 1 hour at 37° C. in Tris buffered saline (20 mM Tris, 150 mM NaCl, pH 7.4 containing 0.01 sodium azide). Following incubation, the solution is centrifuged for 20 minutes at 21,000 g to sediment the Aβ(1-40) fibers along with any bound test compound. The amount of test compound remaining in the supernatant can then be determined by reading the absorbance. The fraction of test compound bound can then be calculated by comparing the amount remaining in the supernatants of incubations with Aβ to the amount remaining in control incubations which do not contain Aβ fibers. Thioflavin T and Congo Red, both of which are known to bind to Aβ fibers, may be included in each assay run as positive controls. Before assaying, test compounds can be diluted to 40 μM, which would be twice the concentration in the final test, and then scanned using the Hewlett Packard 8453 UV/VIS spectrophotometer to determine if the absorbance is sufficient for detection.

In another embodiment, the invention pertains to a method for improving cognition in a subject suffering from an amyloid-related disease. The method includes administering an effective amount of a therapeutic compound of the invention, such that the subject's cognition is improved. The subject's cognition can be tested using methods known in the art such as the Clinical Dementia Rating ("CDR"), Mini-Mental State Examination ("MMSE"), and the Alzheimer's Disease Assessment Scale-Cognition ("ADAS-Cog").

In another embodiment, the invention pertains to a method for treating a subject for an amyloid-related disease. The method includes administering a cognitive test to a subject prior to administration of a compound of the invention, administering an effective amount of a compound of the invention to the subject, and administering a cognitive test to the subject subsequent to administration of the compound, such that the subject is treated for the amyloid-related disease, wherein the subject's score on said cognitive test is improved.

"Improvement," "improved" or "improving" in cognition is present within the context of the present invention if there is a statistically significant difference in the direction of normality between the performance of subjects treated using the methods of the invention as compared to members of a placebo group, historical control, or between subsequent tests given to the same subject.

In one embodiment, a subject's CDR is maintained at 0. In another embodiment, a subject's CDR is decreased (e.g., improved) by about 0.25 or more, about 0.5 or more, about 1.0 or more, about 1.5 or more, about 2.0 or more, about 2.5 or more, or about 3.0 or more. In another embodiment, the rate of increase of a subject's CDR rating is reduced by about 5% or more, about 10% or more, about 20% or more, about 25% or more, about 30% or more, about 40% or more, about 50% or more, about 60% or more, about 70% or more, about 80% or more, about 90% or more, or about 100% or more of the increase of the historical or untreated controls.

In one embodiment, a subject's score on the MMSE is maintained. Alternatively, the subject's score on the MMSE may be increased by about 1, about 2, about 3, about 4, about 5, about 7.5, about 10, about 12.5, about 15, about 17.5, about 20, or about 25 points. In another alternative, the rate of the decrease of a subject's MMSE score as compared to historical controls is reduced. For example, the rate of the decrease of a subject's MMSE score may be reduced by about 5% or more, about 10% or more, about 20% or more, about 25% or more, about 30% or more, about 40% or more, about 50% or more, about 60% or more, about 70% or more, about 80% or more, about 90% or more, or about 100% or more of the decrease of the historical or untreated controls.

In one embodiment, the invention pertains to a method for treating, slowing or stopping an amyloid-related disease associated with cognitve impairment, by administering to a subject an effective amount of a therapeutic compound of the invention, wherein the annual deterioration of the subject's cognition as measured by ADAS-Cog is less than 8 points per year, less the 6 points per year, less than 5 points per year, less than 4 points per year, or less than 3 points per year. In a further embodiment, the invention pertains to a method for treating, slowing or stopping an amyloid-related disease associated with cognition by administering an effective amount of a therapeutic compound of the invention such that the subject's cognition as measured by ADAS-Cog remains constant over a year. "Constant" includes fluctuations of no more than 2 points. Remaining constant includes fluctuations of two points or less in either direction. In a further embodiment, the subject's cognition improves by 2 points or greater per year, 3 points or greater per year, 4 point or greater per year, 5 points or greater per year, 6 points or greater per year, 7 points or greater per year, 8 points or greater per year, etc. as measured by the ADAS-Cog. In another alternative, the rate of the increase of a subject's ADAS-Cog score as compared to historical controls is reduced. For example, the rate of the increase of a subject's ADAS-Cog score may be reduced by about 5% or more, about 10% or more, about 20% or more, about 25% or more, about 30% or more, about 40% or more, about 50% or more, about 60% or more, about 70% or more, about 80% or more, about 90% or more or about 100% of the increase of the historical or untreated controls.

In another embodiment, the ratio of Aβ42:Aβ40 in the CSF or plasma of a subject decreases by about 15% or more, about 20% or more, about 25% or more, about 30% or more, about 35% or more, about 40% or more, about 45% or more, or about 50% or more. In another embodiment, the levels of Aβ in the subject's cerebrospinal fluid decrease by about 15% or more, about 25% or more, about 35% or more, about 45% or more, about 55% or more, about 75% or more, or about 90% or more.

It is to be understood that wherever values and ranges are provided herein, e.g., in ages of subject populations, dosages, and blood levels, all values and ranges encompassed by these values and ranges, are meant to be encompassed within the scope of the present invention. Moreover, all values in these values and ranges may also be the upper or lower limits of a range.

Furthermore, the invention pertains to any novel chemical compound described herein. That is, the invention relates to novel compounds, and novel methods of their use as described herein, which are within the scope of the Formulae disclosed herein, and which are not disclosed in the cited patents and patent Applications.

Synthesis of Compounds of the Invention

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here. Functional and structural equivalents of the compounds described herein and which have the same general properties, wherein one or more simple variations of substituents are made which do not adversely affect the essential nature or the utility of the compound are also included.

The compounds of the present invention may be readily prepared in accordance with the synthesis schemes and protocols described herein, as illustrated in the specific procedures provided. However, those skilled in the art will recognize that other synthetic pathways for forming the compounds of this invention may be used, and that the following is provided merely by way of example, and is not limiting to the present invention. See, e.g., "Comprehensive Organic Transformations" by R. Larock, VCH Publishers (1989). It will be further recognized that various protecting and deprotecting strategies will be employed that are standard in the art (See, e.g., "Protective Groups in Organic Synthesis" by Greene and Wuts). Those skilled in the relevant arts will recognize that the selection of any particular protecting group (e.g., amine and carboxyl protecting groups) will depend on the stability of the protected moiety with regards to the subsequent reaction conditions and will understand the appropriate selections.

Further illustrating the knowledge of those skilled in the art is the following sampling of the extensive chemical literature: "Chemistry of the Amino Acids" by J. P. Greenstein and M. Winitz, John Wiley & Sons, Inc., New York (1961); "Comprehensive Organic Transformations" by R. Larock, VCH Publishers (1989); T. D. Ocain, et al., J. Med. Chem. 31, 2193-99 (1988); E. M. Gordon, et al., J. Med. Chem. 31, 2199-10 (1988); "Practice of Peptide Synthesis" by M. Bodansky and A. Bodanszky, Springer-Verlag, New York (1984); "Protective Groups in Organic Synthesis" by T. Greene and P. Wuts (1991); "Asymmetric Synthesis: Construction of Chiral Molecules Using Amino Acids" by G. M. Coppola and H. F. Schuster, John Wiley & Sons, Inc., New York (1987); "The Chemical Synthesis of Peptides" by J. Jones, Oxford University Press, New York (1991); and "Introduction of Peptide Chemistry" by P. D. Bailey, John Wiley & Sons, Inc., New York (1992).

The synthesis of compounds of the invention is carried out in a solvent. Suitable solvents are liquids at ambient room temperature and pressure or remain in the liquid state under the temperature and pressure conditions used in the reaction. Useful solvents are not particularly restricted provided that they do not interfere with the reaction itself (that is, they preferably are inert solvents), and they dissolve a certain amount of the reactants. Depending on the circumstances, solvents may be distilled or degassed. Solvents may be, for example, aliphatic hydrocarbons (e.g., hexanes, heptanes, ligroin, petroleum ether, cyclohexane, or methylcyclohexane) and halogenated hydrocarbons (e.g., methylenechloride, chloroform, carbontetrachloride, dichloroethane, chlorobenzene, or dichlororbenzene); aromatic hydrocarbons (e.g., benzene, toluene, tetrahydronaphthalene, ethylbenzene, or xylene); ethers (e.g., diglyme, methyl-tert-butyl ether, methyl-tert-amyl ether, ethyl-tert-butyl ether, diethylether, diisopropylether, tetrahydrofuran or methyltetrahydrofurans, dioxane, dimethoxyethane, or diethyleneglycol dimethylether); nitrites (e.g., acetonitrile); ketones (e.g., acetone); esters (e.g., methyl acetate or ethyl acetate); and mixtures thereof.

In general, after completion of the reaction, the product is isolated from the reaction mixture according to standard techniques. For example, the solvent is removed by evaporation or filtration if the product is solid, optionally under reduced pressure. After the completion of the reaction, water may be added to the residue to make the aqueous layer acidic or basic and the precipitated compound filtered, although care should be exercised when handling water-sensitive compounds. Similarly, water may be added to the reaction mixture with a hydrophobic solvent to extract the target compound. The organic layer may be washed with water, dried over anhydrous magnesium sulphate or sodium sulphate, and the solvent is evaporated to obtain the target compound. The target compound thus obtained may be purified, if necessary, e.g., by recrystallization, reprecipitation, chromatography, or by converting it to a salt by addition of an acid or base.

The compounds of the invention may be supplied in a solution with an appropriate solvent or in a solvent-free form (e.g., lyophilized). In another aspect of the invention, the compounds and buffers necessary for carrying out the methods of the invention may be packaged as a kit, optionally including a container. The kit may be commercially used for treating or preventing amyloid-related disease according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The term "container" includes any receptacle for holding the therapeutic compounds. For example, in one embodiment, the container is the packaging that contains the compound. In other embodiments, the container is not the packaging that contains the compound, i.e., the container is a receptacle, such as a box or vial that contains the packaged compound or unpackaged compound and the instructions for use of the compound. Moreover, packaging techniques are well known in the art. It should be understood that the instructions for use of the therapeutic compound may be contained on the packaging containing the therapeutic compound, and as such the instructions form an increased functional relationship to the packaged product.

Pharmaceutical Preparations

In another embodiment, the present invention relates to pharmaceutical compositions comprising agents according to any of the Formulae herein for the treatment of an amyloid-related disease, as well as methods of manufacturing such pharmaceutical compositions.

In general, the agents of the present invention may be prepared by the methods illustrated in the general reaction schemes as, for example, in the patents and patent applications referred to herein, or by modifications thereof, using readily available starting materials, reagents and conventional synthesis procedures. In these reactions, it is also possible to make use of variants which are in themselves known, but are not mentioned here. Functional and structural equivalents of the agents described herein and which have the same general properties, wherein one or more simple variations of substituents are made which do not adversely affect the essential nature or the utility of the agent are also included.

The agents of the invention may be supplied in a solution with an appropriate solvent or in a solvent-free form (e.g., lyophilized). In another aspect of the invention, the agents and buffers necessary for carrying out the methods of the invention may be packaged as a kit. The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The therapeutic agent may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

To administer the therapeutic agent by other than parenteral administration, it may be necessary to coat the agent with, or co-administer the agent with, a material to prevent its inactivation. For example, the therapeutic agent may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7, 27 (1984)).

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi.

Suitable pharmaceutically acceptable vehicles include, without limitation, any non-immunogenic pharmaceutical adjuvants suitable for oral, parenteral, nasal, mucosal, transdermal, intravascular (IV), intraarterial (IA), intramuscular (IM), and subcutaneous (SC) administration routes, such as phosphate buffer saline (PBS).

The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

The therapeutic agent can be orally administered, for example, with an inert diluent or an assimilable edible carrier. The therapeutic agent and other ingredients may also be enclosed in a hard or soft shell gelatin capsule, compressed into tablets, or incorporated directly into the subject's diet. For oral therapeutic administration, the therapeutic agent may be incorporated with excipients and used in the form of ingestible tablets, buccal tablets, troches, capsules, elixirs, suspensions, syrups, wafers, and the like. The percentage of the therapeutic agent in the compositions and preparations may, of course, be varied. The amount of the therapeutic agent in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic agent calculated to produce the desired therapeutic effect in association with the required pharmaceutical vehicle. The specification for the dosage unit forms of the invention are dictated by and directly dependent on (a) the unique characteristics of the therapeutic agent and the particular therapeutic effect to be achieved, and (b) the limitations inherent in the art of compounding such a therapeutic agent for the treatment of amyloid deposition in subjects.

The present invention therefore includes pharmaceutical formulations comprising the agents of the Formulae described herein, including pharmaceutically acceptable salts thereof, in pharmaceutically acceptable vehicles for aerosol, oral and parenteral administration. Also, the present invention includes such agents, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the present invention, an agent of the Formulae described herein, and pharmaceutically acceptable salts thereof, may be administered orally or through inhalation as a solid, or may be administered intramuscularly or intravenously as a solution, suspension or emulsion. Alternatively, the agents or salts may also be administered by inhalation, intravenously or intramuscularly as a liposomal suspension.

Pharmaceutical formulations are also provided which are suitable for administration as an aerosol, by inhalation. These formulations comprise a solution or suspension of the desired agent of any Formula herein, or a salt thereof, or a plurality of solid particles of the agent or salt. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any Formula described herein, or a salt thereof, in any appropriate manner known in the art, such as by micronization. The size of the solid particles or droplets will be, for example, from about 1 to about 2 microns. In this respect, commercial nebulizers are available to achieve this purpose.

A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

Peroral compositions also include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions may also be coated by conventional methods, typically with pH or time-dependent coatings, such that the subject agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of an agent of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emolients, emulsifiers, thickening agents, solvents and the like.

In one embodiment, active agents are administered at a therapeutically effective dosage sufficient to inhibit amyloid deposition in a subject. A "therapeutically effective" dosage inhibits amyloid deposition by, for example, at least about 20%, or by at least about 40%, or even by at least about 60%, or by at least about 80% relative to untreated subjects. In the case of an Alzheimer's subject, a "therapeutically effective" dosage stabilizes cognitive function or prevents a further decrease in cognitive function (i.e., preventing, slowing, or stopping disease progression). The present invention accordingly provides therapeutic drugs. By "therapeutic" or "drug" is meant an agent having a beneficial ameliorative or prophylactic effect on a specific disease or condition in a living human or non-human animal.

In the case of AA or AL amyloidosis, the agent may improve or stabilize specific organ function. As an example, renal function may be stabilized or improved by 10% or greater, 20% or greater, 30% or greater, 40% or greater, 50% or greater, 60% or greater, 70% or greater, 80% or greater, or by greater than 90%.

In the case of IAPP, the agent may maintain or increase β-islet cell function, as determined by insulin concentration or the Pro-IAPP/IAPP ratio. In a further embodiment, the Pro-IAPP/IAPP ratio is increased by about 10% or greater, about 20% or greater, about 30% or greater, about 40% or greater, or by about 50%. In a further embodiment, the ratio is increased up to 50%. In addition, a therapeutically effective amount of the agent may be effective to improve glycemia or insulin levels.

In another embodiment, the active agents are administered at a therapeutically effective dosage sufficient to treat AA (secondary) amyloidosis and/or AL (primary) amyloidosis, by stabilizing renal function, decreasing proteinuria, increasing creatinine clearance (e.g., by at least 50% or greater or by at least 100% or greater), remission of chronic diarrhea, or by weight gain (e.g., 10% or greater). In addition, the agents may be administered at a therapeutically effective dosage sufficient to improve nephrotic syndrome.

Furthermore, active agents may be administered at a therapeutically effective dosage sufficient to decrease deposition in a subject of amyloid protein, e.g., Aβ40 or Aβ42. A therapeutically effective dosage decreases amyloid deposition by, for example, at least about 15%, or by at least about 40%, or even by at least 60%, or at least by about 80% relative to untreated subjects.

In another embodiment, active agents are administered at a therapeutically effective dosage sufficient to increase or enhance amyloid protein, e.g., Aβ40 or Aβ42, in the blood, CSF, or plasma of a subject. A therapeutically effective dosage increases the concentration by, for example, at least about 15%, or by at least about 40%, or even by at least 60%, or at least by about 80% relative to untreated subjects.

In yet another embodiment, active agents are administered at a therapeutically effective dosage sufficient to maintain a subject's CDR rating at its base line rating or at 0. In another embodiment, the active agents are administered at a therapeutically effective dosage sufficient to decrease a subject's CDR rating by about 0.25 or more, about 0.5 or more, about 1.0 or more, about 1.5 or more, about 2.0 or more, about 2.5 or more, or about 3.0 or more. In another embodiment, the active agents are administered at a therapeutically effective dosage sufficient to reduce the rate of the increase of a subject's CDR rating as compared to historical or untreated controls. In another embodiment, the therapeutically effective dosage is sufficient to reduce the rate of increase of a subject's CDR rating (relative to untreated subjects) by about 5% or greater, about 10% or greater, about 20% or greater, about 25% or greater, about 30% or greater, about 40% or greater, about 50% or greater, about 60% or greater, about 70% or greater, about 80% or greater, about 90% or greater or about 100% or greater.

In yet another embodiment, active agents are administered at a therapeutically effective dosage sufficient to maintain a subject's score on the MMSE. In another embodiment, the active agents are administered at a therapeutically effective dosage sufficient to increase a subject's MMSE score by about 1, about 2, about 3, about 4, about 5, about 7.5, about 10, about 12.5, about 15, about 17.5, about 20, or about 25 points. In another embodiment, the active agents are administered at a therapeutically effective dosage sufficient to reduce the rate of the decrease of a subject's MMSE score as compared to historical controls. In another embodiment, the therapeutically effective dosage is sufficient to reduce the rate of decrease of a subject's MMSE score may be about 5% or less, about 10% or less, about 20% or less, about 25% or less, about 30% or less, about 40% or less, about 50% or less, about 60% or less, about 70% or less, about 80% or less, about 90% or less or about 100% or less, of the decrease of the historical or untreated controls.

In yet another embodiment, active agents are administered at a therapeutically effective dosage sufficient to maintain a subject's score on the ADAS-Cog. In another embodiment, the active agents are administered at a therapeutically effective dosage sufficient to decrease a subject's ADAS-Cog score by about 2 points or greater, by about 3 points or greater, by about 4 points or greater, by about 5 points or greater, by about 7.5 points or greater, by about 10 points or greater, by about 12.5 points or greater, by about 15 points or greater, by about 17.5 points or greater, by about 20 points or greater, or by about 25 points or greater. In another embodiment, the active agents are administered at a therapeutically effective dosage sufficient to reduce the rate of the increase of a subject's ADAS-Cog scores as compared to historical or untreated controls. In another embodiment, the therapeutically effective dosage is sufficient to reduce the rate of increase of a subject's ADAS-Cog scores (relative to untreated subjects) by about 5% or greater, about 10% or greater, about 20% or greater, about 25% or greater, about 30% or greater, about 40% or greater, about 50% or greater, about 60% or greater, about 70% or greater, about 80% or greater, about 90% or greater or about 100% or greater.

In another embodiment, active agents are administered at a therapeutically effective dosage sufficient to decrease the ratio of $A\beta42:A\beta40$ in the CSF or plasma of a subject by about 15% or more, about 20% or more, about 25% or more, about 30% or more, about 35% or more, about 40% or more, about 45% or more, or about 50% or more.

In another embodiment, active agents are administered at a therapeutically effective dosage sufficient to lower levels of $A\beta$ in the CSF or plasma of a subject by about 15% or more, about 25% or more, about 35% or more, about 45% or more, about 55% or more, about 75% or more, or about 95% or more.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50, and usually a larger therapeutic index is more efficacious. While agents that exhibit toxic side effects may be used, care should be taken to design a delivery system that targets such agents to the site of affected tissue in order to minimize potential damage to unaffected cells and, thereby, reduce side effects.

It is understood that appropriate doses depend upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the subject. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses depend upon the potency. Such appropriate doses may be determined using the assays described herein. When one or more of these compounds is to be administered to an animal (e.g., a human), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific agent employed, the age, body weight, general health, gender, and diet of the subject, the time of administration, the route of administration, the rate of excretion, and any drug combination.

The ability of an agent to inhibit amyloid deposition can be evaluated in an animal model system that may be predictive of efficacy in inhibiting amyloid deposition in human diseases, such as a transgenic mouse expressing human APP or other relevant animal models where $A\beta$ deposition is seen or for example in an animal model of AA amyloidosis. Likewise, the ability of an agent to prevent or reduce cognitive impairment in a model system may be indicative of efficacy in humans. Alternatively, the ability of an agent can be evaluated by examining the ability of the agent to inhibit amyloid fibril formation in vitro, e.g., using a fibrillogenesis assay such as that described herein, including a ThT, CD, or EM assay. Also the binding of an agent to amyloid fibrils may be measured using a MS assay as described herein. The ability of the agent to protect cells from amyloid induced toxicity is determined in vitro using biochemical assays to determine percent cell death induced by amyloid protein. The ability of an agent to modulate renal function may also be evaluated in an appropriate animal model system.

The therapeutic agent of the invention may be also be administered ex vivo to inhibit amyloid deposition or treat certain amyloid-related diseases, such as $\beta_2M$ amyloidosis and other amyloidoses related to dialysis. Ex vivo administration of the therapeutic agents of the invention can be accomplished by contacting a body fluid (e.g., blood, plasma, etc.) with a therapeutic compound of the invention such that the therapeutic compound is capable of performing its intended function and administering the body fluid to the subject. The therapeutic compound of the invention may perform its function ex vivo (e.g., dialysis filter), in vivo (e.g., administered with the body fluid), or both. For example, a therapeutic compound of the invention may be used to reduce plasma $\beta_2M$ levels and/or maintain $\beta_2M$ in its soluble form ex vivo, in vivo, or both.

Blood-Brain Barrier

Regardless of the particular mechanism by which the compound exerts its biological effects, the compound prevents or treats amyloid-related diseases, such as for example Alzheimer's disease, CAA, diabetes related amyloidosis, AL amyloidosis, Down's syndrome, or $\beta_2 M$ amyloidosis. The compound may reverse or favor deposition of amyloid or the compound may favor plaque clearance or slow deposition. For example, the compound may decrease the amyloid concentration in the brain of a subject versus an untreated subject. The compound may penetrate into the brain by crossing the blood-brain barrier ("BBB") to exert its biological effect. The compound may maintain soluble amyloid in a non-fibrillar form, or alternatively, the compound may increase the rate of clearance of soluble amyloid from the brain of a subject versus an untreated subject. The compound may also increase the rate of degradation of $A\beta$ in the brain prior to organization into fibrils. A compound may also act in the periphery, causing a change in the equilibrium of the amyloid protein concentration in the two compartments (i.e., systemic vs. central), in which case a compound may not be required to penetrate the brain to decrease the concentration of $A\beta$ in the brain (a "sink" effect).

Agents of the invention that exert their physiological effect in vivo in the brain may be more useful if they gain access to target cells in the brain. Non-limiting examples of brain cells are neurons, glial cells (astrocytes, oligodendrocytes, microglia), cerebrovascular cells (muscle cells, endothelial cells), and cells that comprise the meninges. The blood brain barrier ("BBB") typically restricts access to brain cells by acting as a physical and functional blockade that separates the brain parenchyma from the systemic circulation (see, e.g., Pardridge, et al., *J. Neurovirol.* 5(6), 556-69 (1999); Rubin, et al., *Rev. Neurosci.* 22, 11-28 (1999)). Circulating molecules are normally able to gain access to brain cells via one of two processes: lipid-mediated transport through the BBB by free diffusion, or active (or catalyzed) transport.

The agents of the invention may be formulated to improve distribution in vivo, for example as powdered or liquid tablet or solution for oral administration or as a nasal spray, nose drops, a gel or ointment, through a tube or catheter, by syringe, by packtail, by pledget, or by submucosal infusion. For example, the blood-brain barrier (BBB) excludes many highly hydrophilic agents. To ensure that the more hydrophilic therapeutic agents of the invention cross the BBB, they may be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties" or "targeting groups" or "transporting vectors"), thus providing targeted drug delivery (see, e.g., V. V. Ranade *J. Clin. Pharmacol.* 29, 685 (1989)). Likewise, the agents may be linked to targeting groups that facilitate penetration of the blood brain barrier. In one embodiment, the method of the present invention employs a naturally occurring polyamine linked to an agent that is a small molecule and is useful for inhibiting e.g., $A\beta$ deposition.

To facilitate transport of agents of the invention across the BBB, they may be coupled to a BBB transport vector (for review of BBB transport vectors and mechanisms, see, Bickel, et al., *Adv. Drug Delivery Reviews* 46, 247-79 (2001)). Exemplary transport vectors include cationized albumin or the OX26 monoclonal antibody to the transferrin receptor; these proteins undergo absorptive-mediated and receptor-mediated transcytosis through the BBB, respectively. Natural cell metabolites that may be used as targeting groups, include, inter alia, putrescine, spermidine, spermine, or DHA. Other exemplary targeting moieties include folate or biotin (see, e.g., U.S. Pat. No. 5,416,016); mannosides (Umezawa, et al., *Biochem. Biophys. Res. Commun.* 153, 1038 (1988)); antibodies (P. G. Bloeman, et al., *FEBS Lett.* 357, 140 (1995); M. Owais, et al., *Antimicrob. Agents Chemother.* 39, 180 (1995)); surfactant protein A receptor (Briscoe, et al., *Am. J. Physiol.* 1233, 134 (1995)); gp120 (Schreier, et al., *J. Biol. Chem.* 269, 9090 (1994)); see also, K. Keinanen and M. L. Laukkanen, *FEBS Lett.* 346, 123 (1994); J. J. Killion and I. J. Fidler, *Immunomethods* 4, 273 (1994).

Examples of other BBB transport vectors that target receptor-mediated transport systems into the brain include factors such as insulin, insulin-like growth factors ("IGF-I," and "IGF-II"), angiotensin II, atrial and brain natriuretic peptide ("ANP," and "BNP"), interleukin I ("IL-1") and transferrin. Monoclonal antibodies to the receptors that bind these factors may also be used as BBB transport vectors. BBB transport vectors targeting mechanisms for absorptive-mediated transcytosis include cationic moieties such as cationized LDL, albumin or horseradish peroxidase coupled with polylysine, cationized albumin or cationized immunoglobulins. Small basic oligopeptides such as the dynorphin analogue E-2078 and the ACTH analogue ebiratide may also cross the brain via absorptive-mediated transcytosis and are potential transport vectors.

Other BBB transport vectors target systems for transporting nutrients into the brain. Examples of such BBB transport vectors include hexose moieties, e.g., glucose and monocarboxylic acids, e.g., lactic acid and neutral amino acids, e.g., phenylalanine and amines, e.g., choline and basic amino acids, e.g., arginine, nucleosides, e.g., adenosine and purine bases, e.g., adenine, and thyroid hormone, e.g., triiodothyridine. Antibodies to the extracellular domain of nutrient transporters may also be used as transport vectors. Other possible vectors include angiotensin II and ANP, which may be involved in regulating BBB permeability.

In some cases, the bond linking the therapeutic agent to the transport vector may be cleaved following transport into the brain in order to liberate the biologically active agent. Exemplary linkers include disulfide bonds, ester-based linkages, thioether linkages, amide bonds, acid-labile linkages, and Schiff base linkages. Avidin/biotin linkers, in which avidin is covalently coupled to the BBB drug transport vector, may also be used. Avidin itself may be a drug transport vector.

Transcytosis, including receptor-mediated transport of compositions across the blood brain barrier, may also be suitable for the agents of the invention. Transferrin receptor-mediated delivery is disclosed in U.S. Pat. Nos. 5,672,683; 5,383,988; 5,527,527; 5,977,307; and 6,015,555. Transferrin-mediated transport is also known. P. M. Friden, et al., *Pharmacol. Exp. Ther.* 278, 1491-98 (1996); H. J. Lee, *J. Pharmacol. Exp. Ther.* 292, 1048-52 (2000). EGF receptor-mediated delivery is disclosed in Y. Deguchi, et al., *Bioconjug. Chem.* 10, 32-37 (1999), and transcytosis is described in A. Cerletti, et al., *J. Drug Target.* 8, 435-46 (2000). Insulin fragments have also been used as carriers for delivery across the blood brain barrier. M. Fukuta, et al., *Pharm. Res.* 11. 1681-88 (1994). Delivery of agents via a conjugate of neutral avidin and cationized human albumin has also been described. Y. S. Kang, et al., *Pharm. Res.* 1, 1257-64 (1994).

Other modifications in order to enhance penetration of the agents of the invention across the blood brain barrier may be accomplished using methods and derivatives known in the art. For example, U.S. Pat. No. 6,024,977 discloses covalent polar lipid conjugates for targeting to brain and central nervous system. U.S. Pat. No. 5,017,566 discloses cyclodextrin derivatives comprising inclusion complexes of lipoidal forms of dihydropyridine redox targeting moieties. U.S. Pat. No. 5,023,252 discloses the use of pharmaceutical compositions comprising a neurologically active drug and a compound for facilitating transport of the drug across the blood-brain barrier including a macrocyclic ester, diester, amide, diamide, amidine, diamidine, thioester, dithioester, thioamide, ketone or lactone. U.S. Pat. No. 5,024,998 discloses parenteral solutions of aqueous-insoluble drugs with cyclodextrin derivatives. U.S. Pat. No. 5,039,794 discloses the use of a metastatic tumor-derived egress factor for facilitating the transport of compounds across the blood-brain barrier. U.S. Pat. No. 5,112,863 discloses the use of N-acyl amino acid derivatives as antipsychotic drugs for delivery across the blood-brain barrier. U.S. Pat. No. 5,124,146 discloses a method for delivery of therapeutic agents across the blood-brain barrier at sites of increase permeability associated with brain lesions. U.S. Pat. No. 5,153,179 discloses acylated glycerol and derivatives for use in a medicament for improved penetration of cell membranes. U.S. Pat. No. 5,177,064 discloses the use of lipoidal phosphonate derivatives of nucleoside antiviral agents for delivery across the blood-brain barrier. U.S. Pat. No. 5,254,342 discloses receptor-mediated transcytosis of the blood-brain barrier using the transferrin receptor in combination with pharmaceutical compounds that enhance or accelerate this process. U.S. Pat. No. 5,258,402 discloses treatment of epilepsy with imidate derivatives of anticonvulsive sulfamate. U.S. Pat. No. 5,270,312 discloses substituted piperazines as central nervous system agents. U.S. Pat. No. 5,284,876 discloses fatty acid conjugates of dopamine drugs. U.S. Pat. No. 5,389,623 discloses the use of lipid dihydropyridine derivatives of anti-inflammatory steroids or steroid sex hormones for delivery across the blood-brain barrier. U.S. Pat. No. 5,405,834 discloses prodrug derivatives of thyrotropin releasing hormone. U.S. Pat. No. 5,413,996 discloses acyloxyalkyl phosphonate conjugates of neurologically-active drugs for anionic sequestration of such drugs in brain tissue. U.S. Pat. No. 5,434,137 discloses methods for the selective opening of abnormal brain tissue capillaries using bradykinin infused into the carotid artery. U.S. Pat. No. 5,442,043 discloses a peptide conjugate between a peptide having a biological activity and incapable of crossing the blood-brain barrier and a peptide which exhibits no biological activity and is capable of passing the blood-brain barrier by receptor-mediated endocytosis. U.S. Pat. No. 5,466,683 discloses water soluble analogues of an anticonvulsant for the treatment of epilepsy. U.S. Pat. No. 5,525,727 discloses compositions for differential uptake and retention in brain tissue comprising a conjugate of a narcotic analgesic and agonists and antagonists thereof with a lipid form of dihydropyridine that forms a redox salt upon uptake across the blood-brain barrier that prevents partitioning back to the systemic circulation.

Nitric oxide is a vasodilator of the peripheral vasculature in normal tissue of the body. Increasing generation of nitric oxide by nitric oxide synthase causes vasodilation without loss of blood pressure. The blood-pressure-independent increase in blood flow through brain tissue increases cerebral bioavailability of blood-born compositions. This increase in nitric oxide may be stimulated by administering L-arginine. As nitric oxide is increased, cerebral blood flow is consequently increased, and drugs in the blood stream are carried along with the increased flow into brain tissue. Therefore, L-arginine may be used in the pharmaceutical compositions of the invention to enhance delivery of agents to brain tissue after introducing a pharmaceutical composition into the blood stream of the subject substantially contemporaneously with a blood flow enhancing amount of L-arginine, as described in WO 00/56328.

Still further examples of modifications that enhance penetration of the blood brain barrier are described in International (PCT) Application Publication Number WO 85/02342, which discloses a drug composition comprising a glycerolipid or derivative thereof. PCT Publication Number WO 089/11299 discloses a chemical conjugate of an antibody with an enzyme which is delivered specifically to a brain lesion site for activating a separately-administered neurologically-active prodrug. PCT Publication Number WO 91/04014 discloses methods for delivering therapeutic and diagnostic agents across the blood-brain barrier by encapsulating the drugs in liposomes targeted to brain tissue using transport-specific receptor ligands or antibodies. PCT Publication Number WO 91/04745 discloses transport across the blood-brain barrier using cell adhesion molecules and fragments thereof to increase the permeability of tight junctions in vascular endothelium. PCT Publication Number WO 91/14438 discloses the use of a modified, chimeric monoclonal antibody for facilitating transport of substances across the blood-brain barrier. PCT Publication Number WO 94/01131 discloses lipidized proteins, including antibodies. PCT Publication Number WO 94/03424 discloses the use of amino acid derivatives as drug conjugates for facilitating transport across the blood-brain barrier. PCT Publication Number WO 94/06450 discloses conjugates of neurologically-active drugs with a dihydropyridine-type redox targeting moiety and comprising an amino acid linkage and an aliphatic residue. PCT Publication Number WO 94/02178 discloses antibody-targeted liposomes for delivery across the blood-brain barrier. PCT Publication Number WO 95/07092 discloses the use of drug-growth factor conjugates for delivering drugs across the blood-brain barrier. PCT Publication Number WO 96/00537 discloses polymeric microspheres as injectable drug-delivery vehicles for delivering bioactive agents to sites within the central nervous system. PCT Publication Number WO 96/04001 discloses omega-3-fatty acid conjugates of neurologically-active drugs for brain tissue delivery. PCT WO 96/22303 discloses fatty acid and glycerolipid conjugates of neurologically-active drugs for brain tissue delivery.

In general, it is well within the ordinary skill in the art to prepare an ester, amide or hydrazide derivative of an agent of the invention, for example, from the corresponding carboxylic acid and a suitable reagent. For instance, a carboxylic acid-containing compound, or a reactive equivalent thereof, may be reacted with a hydroxyl-containing compound, or a reactive equivalent thereof, so as to provide the corresponding ester. See, e.g., "Comprehensive Organic Transformations," $2^{nd}$ Ed., by R. C. Larock, VCH Publishers John Wiley & Sons, Ltd. (199989); "March's Advanced Organic Chemistry," $5^{th}$ Ed., by M. B. Smith and J. March, John Wiley & Sons, Ltd. (2000).

Prodrugs

The present invention is also related to prodrugs of the agents of the Formulae disclosed herein. Prodrugs are agents which are converted in vivo to active forms (see, e.g., R. B. Silverman, 1992, "The Organic Chemistry of Drug Design and Drug Action," Academic Press, Chp. 8). Prodrugs can be used to alter the biodistribution (e.g., to allow agents which would not typically enter the reactive site of the protease) or the pharmacokinetics for a particular agent. For example, a carboxylic acid group, can be esterified, e.g., with a methyl group or an ethyl group to yield an ester. When the ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate agent which subsequently decomposes to yield the active agent. The prodrug moieties may be metabolized in vivo by esterases or by other mechanisms to carboxylic acids.

Examples of prodrugs and their uses are well known in the art (see, e.g., Berge, et al., "Pharmaceutical Salts", *J. Pharm. Sci.* 66, 1-19 (1977)). The prodrugs can be prepared in situ during the final isolation and purification of the agents, or by separately reacting the purified agent in its free acid form with a suitable derivatizing agent. Carboxylic acids can be converted into esters via treatment with an alcohol in the presence of a catalyst.

Examples of cleavable carboxylic acid prodrug moieties include substituted and unsubstituted, branched or unbranched lower alkyl ester moieties, (e.g., ethyl esters, propyl esters, butyl esters, pentyl esters, cyclopentyl esters, hexyl esters, cyclohexyl esters), lower alkenyl esters, dilower alkyl-amino lower-alkyl esters (e.g., dimethylaminoethyl ester), acylamino lower alkyl esters, acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, dilower alkyl amides, and hydroxy amides.

Pharmaceutically Acceptable Salts

Certain embodiments of the present agents can contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of agents of the present invention. These salts can be prepared in situ during the final isolation and purification of the agents of the invention, or by separately reacting a purified agent of the invention in its free base form with a suitable organic or inorganic acid, and isolating the salt thus formed.

Representative salts include the hydrohalide (including hydrobromide and hydrochloride), sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, 2-hydroxyethanesulfonate, and laurylsulphonate salts and the like. See, e.g., Berge et al., "Pharmaceutical Salts", *J. Pharm. Sci.* 66, 1-19 (1977).

In other cases, the agents of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of agents of the present invention.

These salts can likewise be prepared in situ during the final isolation and purification of the agents, or by separately reacting the purified agent in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

"Pharmaceutically acceptable salts" also includes, for example, derivatives of agents modified by making acid or base salts thereof, as described further below and elsewhere in the present application. Examples of pharmaceutically acceptable salts include mineral or organic acid salts of basic residues such as amines; and alkali or organic salts of acidic residues such as carboxylic acids. Pharmaceutically acceptable salts include the conventional non-toxic salts or the quaternary ammonium salts of the parent agent formed, for example, from non-toxic inorganic or organic acids. Such conventional non-toxic salts include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic acid. Pharmaceutically acceptable salts may be synthesized from the parent agent which contains a basic or acidic moiety by conventional chemical methods. Generally, such salts may be prepared by reacting the free acid or base forms of these agents with a stoichiometric amount of the appropriate base or acid in water or in an organic solvent, or in a mixture of the two.

All acid, salt, base, and other ionic and non-ionic forms of the compounds described are included as compounds of the invention. For example, if a compound is shown as an acid herein, the salt forms of the compound are also included. Likewise, if a compound is shown as a salt, the acid and/or basic forms are also included.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, patents, and patent applications cited throughout this application are hereby incorporated by reference. The invention is further illustrated by the following examples, which should not be construed as further limiting.

EXAMPLES

Binding and Antifibrillogenic Assays

The test compounds were synthesized and screened by mass spectrometry ("MS") assays, except for selected compounds which were purchased from a commercial source. The MS assay gives data on the ability of compounds to bind to proteins, in this example, to β-amyloid and IAPP.

In the MS assay for Aβ40, samples were prepared as aqueous solutions (adding 20% ethanol if necessary to solubilize in water), 200 µM of a test compound and 20 µM of solubilized Aβ40, or 400 µM of a test compound and 40 µM of solubilized Aβ40. The pH value of each sample was adjusted to 7.4 (±0.2) by addition of 0.1% aqueous sodium hydroxide. The solutions were then analyzed by electrospray ionization mass spectrometry using a Waters ZQ 4000 mass spectrometer. Samples were introduced by direct infusion at a flow-rate of 25 µL/min within 2 hr. after sample preparation. The source temperature was kept at 70° C. and the cone voltage was 20 V for all the analysis. Data were processed using Masslynx 3.5 software. The MS assay gives data on the ability of compounds to bind to soluble Aβ, whereas the ThT, EM and CD assays give data on inhibition of fibrillogenesis. The results from the assay for binding to Aβ are summarized in Table 3. In Table 3, when a box is blank, it means a value for that compound for that assay The assay for IAPP was conducted under the same conditions except that 200 μM of test compound and 20 μM of solubilized IAPP were employed. The key below describes the codes used in Table 3 to quantify the binding based on the intensity of the absorption.

Key to Table 3

| Aβ1-40 | | | |
|---|---|---|---|
| | Code | 400 μM | 200 μM |
| Strong Binding | +++ | 90-100% | 60-100% |
| Moderate Binding | ++ | 70-89% | 30-69% |
| Weak Binding | + | 45-59% | 20-44% |
| Little/no detectable binding | − | 20-39% | 20-39% |

| IAPP | | | |
|---|---|---|---|
| | | 200 μM (20% EtOH) | 100 μM (20% EtOH) |
| Strong Binding | +++ | >75% | >50% |
| Moderate Binding | ++ | 40-75% | 30-50% |
| Weak Binding | + | 20-40% | 15-30% |
| Little/no detectable binding | − | 0-20% (0-30%) | 0-15% |

TABLE 3

Relative Binding Affinities of Compounds of the Invention

| | MS binding | |
|---|---|---|
| ID | IAPP | Aβ1-40 |
| A | +++ | ++ |
| O | ++ | |
| T | ++ | + |
| AN | − | − |
| BF | ++ | +++ |
| BG | | − |
| BI | | + |
| BT | + | +++ |
| BU | ++ | +++ |
| CA | + | +++ |
| CB | + | ++ |
| CF | + | +++ |
| CU | + | ++ |
| CW | + | +++ |
| CX | ++ | +++ |
| CZ | ++ | +++ |
| DB | ++ | +++ |
| DF | +++ | − |
| EU | + | − |
| EX | + | +++ |
| FB | − | − |
| FC | + | ++ |
| FD | ++ | ++ |
| FE | − | + |
| FG | | − |
| FJ | +++ | ++ |
| FK | ++ | ++ |

Effects of Short Term Treatment in Adult Transgenic CRND8 Mice Overexpressing βApp Transgenic mice, TgCRND8, expressing the human amyloid precursor protein (hAPP) develop a pathology resembling Alzheimer's disease. In particular, high levels of Aβ40 and Aβ42 have been documented in the plasma and the brain of these animals at 8-9 weeks of age, followed by early accumulation of amyloid plaques similar to the senile plaques observed in Aβ patients. These animals also display progressive cognitive deficits that parallel the appearance of degenerative changes. See, e.g., (Chishti, et al., J. Biol. Chem. 276, 21562-70 (2001).

The short term therapeutic effect of 19 compounds of the invention was studied. These compounds were administered over a 14 or 28 day period at the end of which the levels of Aβ peptides in the plasma and brain of TgCRND8 animals were determined.

Methods

Male and female transgenic mice from the $3^{rd}$ and $4^{th}$ B6C3F1 generations were used in this example and given daily subcutaneous or oral administrations of one of a series of compounds for 14 or 28 days. The following abbreviations are used to designate these animals from the $3^{rd}$ and 4th generation backcross in the present protocol: TgCRND8-2.B6C3F1 ($N_3$); TgCRND8-2.B6C3F1 ($N_4$).

Baseline animals (Group 1) consisted of naive TgCRND8-2.B6C3F1($N_3$) at 11±1 weeks of age. These mice were used to determine the Aβ levels in the plasma and brain of naive transgenic animals at the initiation of treatment.

Starting at 11 weeks of age (±1 week) animals received daily administration of their respective treatment for a period of 14 or 28 days (groups 2-21), at a dose of 250 mg/kg at 10 ml/kg or of vehicle only (water; group 2) or 1% methyl cellulose only (group 21). The route of administration was subcutaneous for water-soluble compounds and oral for compounds solubilized in methylcellulose 1% (MC 1%). At the end of the treatment periods, plasma and perfused brains were collected for quantification of Aβ levels.

TABLE 4

| Test System | |
|---|---|
| Species: | Mouse |
| Strain: | TgCRND8-2.B6C3F1($N_3$) & ($N_4$) |
| Genotype: | hAPP +/− |
| Gender: | Male and Female |
| Age at Day 1: | 11 ± 1 weeks |
| Body Weight at Day 1: | 10 to 30 g |
| Number of Groups: | 21 |
| Number of Animals/Group at Day 1: | Baseline: 8 |
| Vehicle and Treated: | 12-15 |
| Suppliers: | TgCRND8-2 founders were obtained from the Centre for Research in Neurodegenerative Diseases, University of Toronto. The inbred B6C3F1 were obtained from Charles River (Quebec, Canada). |

The mice used in this study were derived from a breeding colony at Institut Armand Frappier, and were well-acclimated to the animal facility environment prior to initiation of the study. Animals were assigned, according to age and gender, into the following experimental groups:

TABLE 5

| Groups of Mice | | | |
|---|---|---|---|
| Group No. | Treatment | Daily Dose (mg/kg) | Duration of Treatment (days) |
| 1 | Baseline | NA | NA |
| 2 | Water | NA | 14 & 28 |
| 3 | CF | 250 | 14 & 28 |

TABLE 5-continued

Groups of Mice

| Group No. | Treatment | Daily Dose (mg/kg) | Duration of Treatment (days) |
|---|---|---|---|
| 5 | CU | 250 | 14 & 28 |
| 7 | CW | 250 | 14 & 28 |
| 8 | CA | 250 | 14 & 28 |
| 9 | BE | 250 | 14 & 28 |
| 10 | CX | 250 | 14 & 28 |
| 11 | BT | NA | NA |
| 13 | CZ | 250 | 14 & 28 |
| 14 | BU | 250 | 14 & 28 |
| 17 | DA | 250 | 14 & 28 |
| 19 | CP | 250 | 14 & 28 |
| 21 | Methylcellulose 1% | 100 | 14 & 28 |

Animal Health Monitoring

All animals were examined daily for signs of ill health when handled in the morning for their daily treatment and twice a day for mortality checks (once daily during weekends and holidays). Detailed examinations were performed on the treatment initiation, weekly during the study, and once before terminal procedures. More frequent observations were undertaken when considered appropriate. Death and all individual clinical signs were individually recorded. Individual body weights were recorded at randomization, once weekly during the study, and once before terminal procedures.

Sample Collection

At 11±1 weeks of age for the Baseline group, and at the end of the treatment period (14 or 28 days) for Groups 2 to 21, at 24 hours after the last compound administration animals were sacrificed and samples collected. An approximate blood volume of 500 µl was collected from the orbital sinus and kept on ice until centrifugation at 4° C. at a minimum speed of 3,000 rpm for 10 minutes. Plasma samples were immediately frozen and stored at −80° C. pending analysis. The brains were removed, frozen, and stored at −80° C. awaiting analysis.

Measurements of Aβ Levels

Brains were weighted frozen and homogenized with 4 volumes of ice cold 50 mM Tris-Cl pH 8.0 buffer with protease inhibitor cocktail (4 mL of buffer for 1 g of wet brain).

Samples were spun at 15000 g for 20 minutes and the supernatants were transferred to fresh tubes. One hundred fifty (150) µl from each supernatant were mixed with 250 µl of 8M guanidine-HCL/50 mM Tris-HCL pH 8.0 (ratio of 0.6 vol supernatant:1 vol 8M guanidium/Tris-HCL 50 mM pH8.0) and 400 µL 5 M guanidium/Tris-HCL 50 mM pH8.0 were added. The tubes were vortexed for 30 seconds and frozen at −80° C. In parallel, pellets were treated with 7 volumes of 5 M guanidine-HCL/50 mM Tris-HCL pH 8.0 (7 mL of guanidine for 1 g of wet brain), vortexed for 30 seconds and frozen at −80° C. Samples were thawed at room temperature, sonicated at 80° C. for 15 minutes and frozen again. This cycle was repeated 3 times to ensure homogeneity and samples were returned to −80° C. pending analysis.

Aβ levels were evaluated in plasma and brain samples by ELISA using Human Aβ40 and Aβ42 Fluorometric ELISA kits from Biosource (Cat. No. 89-344 and 89-348) according to manufacturer's recommended procedures. In short, samples were thawed at room temperature, sonicated for 5 minutes at 80° C. (sonication for brain homogenates; no sonication for plasma samples) and kept on ice. Aβ peptides were captured using 100 µl of the diluted samples to the plate and incubated without shaking at 4° C. overnight. The samples were aspirated and the wells were rinsed 4 times with wash buffer obtained from the Biosource ELISA kit. The anti-Aβ40 or anti-Aβ42 rabbit polyclonal antiserum (specific for the Aβ40 or Aβ42 peptide) was added (100 µl) and the plate was incubated at room temperature for 2 hours with shaking. The wells were aspirated and washed 4 times before adding 100 µl of the alkaline phosphatase labeled anti-rabbit antibody and incubating at room temperature for 2 hours with shaking. The plates were then rinsed 5 times and the fluorescent substrate (100 µl) was added to the plate. The plate was incubated for 35 minutes at room temperature and the plate was read using a titer plate reader at an excitation wavelength of 460 nm and emission at 560 nm.

Compounds were scored based on their ability to modulate levels of Aβ peptides in the plasma and the cerebral soluble/insoluble levels in the brain. Levels of Aβ observed in the plasma and brain of treated animals were normalized using values from vehicle-treated (water) or methylcellulose-treated control groups and ranked according to the strength of the pharmacological effect. Results are shown in Tables 3 to 11. Increases in the levels of Aβ peptides are indicated using "+" symbols, while decreases in the levels of Aβ peptides are indicated using "−" symbols. The strongest effects are recorded as "+++" or "−−−" while the weakest are shown as "+" or "−".

Specifically, increases in the levels of Aβ (relative to untreated control) of 20 to 39% are scored as "+"; increases of 40 to 69% are scored as "++"; and increases of 70% or higher are scored as "+++". Decreases in the levels of Aβ of 5 to 19% are scored as "−"; decreases of 20 to 38% are scored as "−−"; and decreases of 39% or more are scored as "−−−".

The data are presented in Tables 6-11. Treatment with these compounds after 14 and/or 28 days resulted in a significant change in the cerebral levels of Aβ40 and/or Aβ42 (Tables 8-11). Furthermore, treatment with these compounds, for instance, Compound BX (3-(t-butyl)amino-1-propanesulfonic acid), resulted after 14 and 28 days (Tables 6-7) in a significant increase in the levels of Aβ peptides in the plasma. This suggests that some of these compounds may act by a peripheral sink effect, sequestering Aβ peptides in the plasma and thereby facilitating their clearance from the CNS as previously suggested for treatment by passive immunization using anti-Aβ monoclonal antibody m266 (DeMattos et al., Science 295(5563):2264-7).

The tables show levels of Aβ peptides in the plasma and brain of TgCRND8 mice treated for 14 and 28 days with compounds of the invention.

Tables 6A and 6C show the data from Day 14 and Day 28 for the Plasma Vehicle group, respectively. Tables 6B and 7 show the data for the Plasma Methylcellulose group on Days 14 and 28, respectively. Tables 8 and 10 show the data on Days 14 and 28 for the Brain homogenate vehicle group, respectively. Tables 9 and 11 show the data for brain homogenate for the Methylcellulose group on Days 14 and 28, respectively.

TABLE 6A

Plasma Vehicle Group, Day 14

| Treatment | Aβ40 Change | Aβ42 Change |
|---|---|---|
| CF | | |
| CU | | |
| CX | ++ | ++ |
| CW | ++ | ++ |
| BE | ++ | +++ |
| CA | +++ | +++ |

TABLE 6B

Plasma Methylcellulose Group, Day 14

| Treatment | Aβ40 Change | Aβ42 Change |
|---|---|---|
| DA |  | + |
| BU | − |  |
| CZ | − | − |
| BT |  |  |

TABLE 6C

Plasma Vehicle Group, Day 28

| Treatment | Aβ40 Change | Aβ42 Change |
|---|---|---|
| CF |  |  |
| CU | + | + |
| CX | ++ | + |
| CW | ++ | + |
| BE | +++ | +++ |
| CA | +++ | +++ |

TABLE 7

Plasma Methylcellulose Group, Day 28

| Treatment | Aβ40 Change | Aβ42 Change |
|---|---|---|
| DA |  | + |
| BU |  |  |
| CZ |  | − |
| BT |  |  |

TABLE 8

Brain Homogenate Vehicle Group, Day 14

| | Aβ40 Change | | Aβ42 Change | |
|---|---|---|---|---|
| Treatment | Soluble | Insoluble | Soluble | Insoluble |
| CF | ++ | − | − | −− |
| CU | + |  | ++ | − |
| CX | − | − | + | − |
| CW** |  |  |  |  |
| BE | + |  | +++ | +++ |
| CA | + | − |  | −− |

**The effect of this compound in the brain has only been tested on its ability to modulate the total levels of Aβ40 and Aβ42 peptides rather than measuring soluble and insoluble levels independently.

TABLE 9

Brain Homogenate Methylcellulose Group, Day 14

| | Aβ40 Change | | Aβ42 Change | |
|---|---|---|---|---|
| Treatment | Soluble | Insoluble | Soluble | Insoluble |
| DA | − | −−− | −− | −− |
| BU | − |  |  | −−− |
| CZ | − | −− | −−− | −−− |
| BT |  | +++ | ++ |  |

TABLE 10

Brain Homogenate Vehicle Group, Day 28

| | Aβ40 Change | | Aβ42 Change | |
|---|---|---|---|---|
| Treatment | Soluble | Insoluble | Soluble | Insoluble |
| CF | + |  |  | + |
| CU |  | +++ | ++ | +++ |
| CX |  | + | ++ | +++ |
| CW** |  | + |  | ++ |
| BE | + | − | +++ | +++ |
| CA | + | ++ | + | + |

**The effect of this compound in the brain has only been tested on its ability to modulate the total levels of Aβ40 and 42 peptides rather than measuring soluble and insoluble levels independently.

TABLE 11

Brain Homogenate Methylcellulose Group, Day 28

| | Aβ40 Change | | Aβ42 Change | |
|---|---|---|---|---|
| Treatment | Soluble | Insoluble | Soluble | Insoluble |
| DA | −− | −− |  | −− |
| BU | −− | −− |  | −− |
| CZ | − |  | − | −− |
| BT | −− | ++ | ++ |  |

Example 11

Evaluation of Compounds Binding to NAC Peptide by Mass Spectrometry

Recent findings have demonstrated that a high percentage of Alzheimer Disease (AD) patients also form Lewy bodies, most abundantly in the amygdala (Hamilton. 2000. *Brain Pathol*, 10:378; Mukaetova-Ladinska, et al. 2000. *J Neuropathol Exp Neurol* 59:408). Interestingly, the highly hydrophobic non-amyloid component (NAC) region of α-synuclein has also been described as the second most abundant component of amyloid plaques in the brain of Aβ patients, after Aβ. Alpha-synuclein has been shown to form fibrils in vitro. Furthermore it binds to Aβ and promotes its aggregation (Yoshimoto, et al. 1995. *Proc Natl Acad Sci USA* 92:9141). It was in fact originally identified as the precursor of the non-amyloid beta (Aβ) component (NAD) of AD plaques (Ueda, et al. 1993. *Proc Natl Acad Sci USA* 90:11282; Iwai. 2000. *Biochem Biophys Acta* 1502:95; Masliah, et al. 1996. *Am J Pathol* 148:201). NAC is a 35 amino acid long peptide with highly hydrophobic stretches which can self-aggregate and form fibrils in vitro. Moreover, these fibrils can efficiently seed the formation of Aβ fibrils in vitro (Han, et al. 1995. *Chem Biol*. 2: 163-169; Iwai, et al. 1995. *Biochemistry* 34:10139). It is in fact through its NAC domain that alpha-synuclein retains its fibrillogenic properties. Modulating the properties of NAC or targeting NAC with the compounds of the invention could therefore be a valid therapeutic avenue to inhibit the formation of protein aggregates and inclusions associated with alpha-synucleopathies, as well as the formation of aggregates between the beta-amyloid peptide and NAC of alpha-synuclein.

The ability of the compounds of the present invention to bind to NAC peptide in aqueous solution was evaluated. The binding ability correlates to the intensities of the peptide-compound complex peaks observed by the Electrospray Mass Spectrum. Millipore distilled deionized water was used to prepare all aqueous solutions. For pH determination a Beckman Φ36 pH meter fitted with a Corning Semi-Micro Combination pH Electrode was employed.

NAC (MW 3260.6 Da) at 20 μM was first analyzed at pH 7.40 and the usual sodium clusters was observed at +2, +3 and +4 at m/z 1335.5, 1116.7 and 843.4 respectively. The optimal cone voltage was determined to be 20V.

Mass spectrometry—Mass spectrometric analysis was performed using a Waters ZQ 4000 mass spectrometer equipped with a Waters 2795 sample manager. MassLynx 4.0 (earlier by MassLynx 3.5) was used for data processing and analysis. Test compounds were mixed with disaggregated peptides in aqueous media (6.6% EtOH) at a 5:1 ratio (20 μM NAC: 100 μM of test compound or 40 μM NAC:200 μM of test compound). The pH of the mixture was adjusted to 7.4 (±0.2) using 0.1% NaOH (3-5 μL). Periodically, NAC peptide solution at 20 μM or 40 μM was also prepared in the same fashion and run as control. The spectra were obtained by introducing the solutions to the electrospray source by direct infusion using a syringe pump at a flow rate of 25 μl/min, and scanning from 100 to 2100 Da in the positive mode. The scan time was 0.9 sec per scan with an inter-scan delay of 0.1 sec and the run time was 5 min for each sample. All the mass spectra were sum of 300 scans. The desolvation and source temperature was 70° C. and the cone and capillary voltage were maintained at 20 V and 3.2 kV respectively.

The total area under the peaks for the bound NAC-compound complex divided by total area under the peaks for unbound NAC was determined for each compound tested. The results are summarized in Table 12 below

TABLE 12

NAC Peptide Binding Data

| Structure | Binding Strength* |
|---|---|
| $CH_3(CH_2)_9N^+(CH_3)_2[(CH_2)_3SO_3^-]$ | +++ |
| $CH_3(CH_2)_{11}N^+(CH_3)_2[(CH_2)_3SO_3^-]$ | ++ |
| $CH_3(CH_2)_{13}N^+(CH_3)_2[(CH_2)_3SO_3^-]$ | ++ |
| $H_2N$~~~$SO_3Na$ | − |
| (azepanone structure with $SO_3Na$) | + |

*+++ = Strong; when the total binding is 120% and higher
++ = Moderate; when the total binding is between 120% and 70%
+ = Weak; when the total binding is between 70% and 30%
− = None; when the total binding is between 30% and 0%

The present invention also relates to novel compounds and the synthesis thereof. Accordingly, the following examples are presented to illustrate how some of those compounds may be prepared.

Synthesis of Compounds of the Invention

Preparation of 3-(4-phenyl-1,2,3,6-tetrahydropyridin-1-yl)-1-propanesulfonic acid (Compound O)

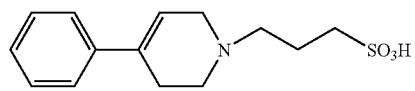

The 4-phenyl-1,2,3,6-tetrahydropyridine hydrochloride (2.51 g, 12.8 mmol) was treated with 1N NaOH (20 mL) and the aqueous mixture was extracted with $CH_2Cl_2$ (20 mL). The organic layer was separated, dried over $MgSO_4$, filtered and solvent was removed under reduced pressure.

To a solution of 4-phenyl-1,2,3,6-tetrahydropyridine (1.95 g, 12.2 mmol) in acetone (20 mL) was added 1,3-propane sultone (1.66 g, 13.5 mmol). The mixture was stirred at reflux for 2 h. The resulting suspension was cooled to room temperature. The solid was collected by filtration, washed with acetone (2×25 mL) and dried in vacuo. The product was suspended in 50% MeOH/acetone (75 mL). The suspension was stirred at reflux for 5 min. The solid material was filtered and washed with acetone (2×25 μL). This allowed the isolation of compound O, 1.74 g (51%).

Preparation of 3-tryptamino-1-propanesulfonic acid (Compound BT)

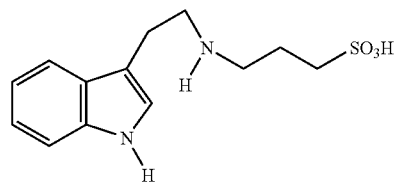

A solution of 1,3-propane sultone (16.5 g, 130 mmol) in 2-butanone (total volume 100 mL) was added dropwise to a warm solution of tryptamine (20.65 g, 129 mmol) in 2-butanone (150 mL). The mixture was heated under reflux for 1 h, cooled to room temperature. The solid was collected by filtration and rinsed 3 times with 2-butanone (60 mL). The crude wet cake (34 g) was transferred into a 500 mL flask and dried under vacuum at room temperature, protected from light. A beige solid (18 g) was obtained. Water (160 mL) and methanol (300 mL) were added. The mixture was heated under reflux with stirring. Activated charcoal (1 g) was added and the resulting mixture was stirred for 30 minutes. The insoluble material was removed by filtration through a pad of Celite. The Celite-pad was washed with hot methanol (4×30 mL). The filtrate and the washings were combined, and concentrated to a thick-paste. Absolute ethanol (100 mL) and methanol (10 mL) were added; and the mixture was heated under reflux for 15 minutes. The mixture was cooled with an ice-bath. The solid was collected by filtration, rinsed washed 90% ethanol (30 mL), absolute ethanol (3×30 mL), air-dried for 10 minutes, and dried in vacuo. The solid was suspended in absolute ethanol (100 mL); and the mixture was heated to reflux. Dropwise addition of water (65 mL) to the alcoholic mixture resulted complete dissolution of the solid. The solution was cooled slowly to room temperature with stirring under nitrogen overnight. The mixture was cooled with an ice-bath. The solid was collected by filtration, rinsed washed 90% ethanol (30 mL), absolute ethanol (3×30 mL), air-dried for 10 minutes, and further dried in vacuo; affording compound BT as a cream colored crystalline solid (11.88 g, 33% yield). The $^1H$ and $^{13}C$ NMR were consistent with the structure.

Preparation of 3-[1-(1,2,3,4-tetrahydro-1-naphthyl)]amino-1-propanesulfonic acid (Compound BU)

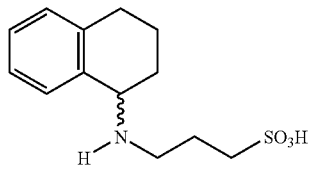

A solution of 1,2,3,4-tetrahydro-1-naphthylamine (24.8 g, 0.168 mol) and 1,3-propane sultone (20.58 g, 0.168 mol) in toluene (300 mL) was heated at 80° C. for 3 h. The mixture was cooled to room temperature; and hexane (500 mL) was added. The precipitate was collected and washed with hexane (2×200 mL). The wet solid was dried in a vacuum oven at 60° C. (dried 40 g). The solid was recrystallized from a mixture of water (80 mL) and ethanol (800 mL). The product was collected by filtration, washed with ethanol (3×50 mL), and dried at 70° C.; affording compound BU as a white solid (26 g, 57%). The $^1$H and $^{13}$C NMR, MS and elemental analysis were consistent with the structure.

Preparation of 3-[(dl)-1-hydroxy-2-pentyl]amino-1-propanesulfonic acid (Compound CA)

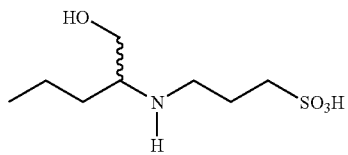

The DL-2-amino-1-pentanol (10 g, 94 mmol) was added to a solution of 1,3-propane sultone (12.6 g, 100 mmol) in 2-butanone (95 mL). The mixture was heated to reflux for 3.5 h. The mixture was cooled to room temperature overnight, and further cooled in an ice-bath. The solid was collected by filtration, rinsed with cold THF. The material was air-dried for 20 minutes (15 g). The solid was suspended in absolute ethanol (80 mL) and the mixture was heated to reflux for 1 h. The mixture was cooled in an ice-bath; and the solid was collected by filtration, rinsed with cold ethanol. The material was air-dried for 15 minutes then at 60° C. in the vacuum oven overnight. Compound CA was obtained as a fine white powder (14.49 g, 68%). The $^1$H and $^{13}$C NMR were consistent with the structure.

We claim:
1. A compound of Formula III:

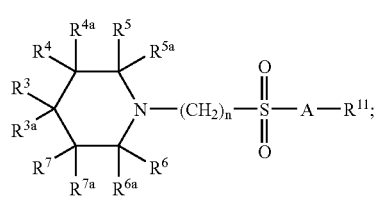

wherein:
A is oxygen and $R^{11}$ is hydrogen, a salt-forming cation, an ester forming group or or —$(CH_2)_x$-Q, or
A is nitrogen and A and $R^{11}$ taken together are a natural or unnatural amino acid or a salt thereof;
Q is hydrogen, thiazolyl, triazolyl, imidazolyl, benzothiazolyl, or benzoimidazolyl;
x is 0, 1, 2, 3, or 4;
n is 0, 1, 2, 3, 4, 5, 6, 7, 8, 9, or 10;
$R^3, R^{3a}, R^4, R^{4a}, R^5, R^{5a}, R^6, R^{6a}, R^7$ and $R^{7a}$ are hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, or two R groups on adjacent ring atoms taken together with the ring atoms form a double bond, provided that $R^4$ or $R^7$ is a moiety of Formula IIIa:

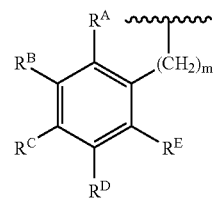

wherein:
m is 0, 1, 2, 3, or 4;
$R^A, R^B, R^C, R^D$, and $R^E$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl; or
$R^{3a}, R^4, R^{4a}, R^5, R^{5a}, R^6, R^{6a}, R^7$ and $R^{7a}$ are hydrogen, and $R^3$ is a moiety of Formula IIIa; or a pharmaceutically acceptable salt thereof, provided that said compound is not 3-(4-phenyl-1,2,3,6-tetrahydro-1-pyridyl)-1-propanesulfonic acid.

2. The compound selected from the group consisting of:

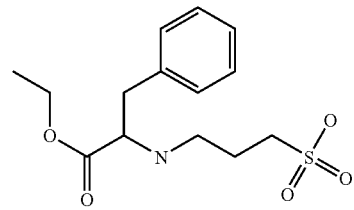

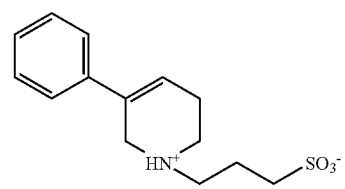

-continued

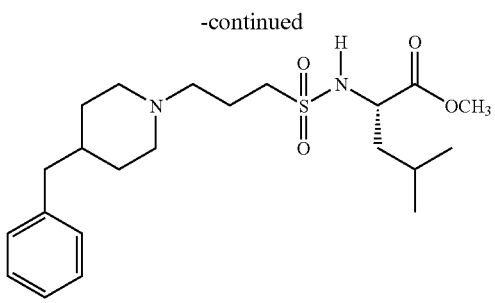

or a pharmaceutically acceptable salt thereof.

3. A pharmaceutical composition comprising a pharmaceutically acceptable vehicle and an effective amount of a compound of Formula III:

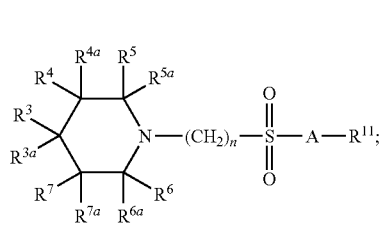

wherein:
A is oxygen and $R^{11}$ is hydrogen, a salt-forming cation, an ester forming group or —$(CH_2)_x$-Q, or
A is nitrogen and A and $R^{11}$ taken together are a natural or unnatural amino acid or a salt thereof;
Q is hydrogen, thiazolyl, triazolyl, imidazolyl, benzothiazolyl, or benzoimidazolyl;
x is 0, 1, 2, 3, or 4;
n is 0, 1, 2, 3, 4, 5, 6, 7, 8, 9, or 10;
$R^3, R^{3a}, R^4, R^{4a}, R^5, R^{5a}, R^6, R^{6a}, R^7$ and $R^{7a}$ are hydrogen, alkyl, mercaptoalkyl, alkenyl, alkynyl, cycloalkyl, aryl, alkylcarbonyl, arylcarbonyl, alkoxycarbonyl, cyano, halogen, amino, tetrazolyl, or two R groups on adjacent ring atoms taken together with the ring atoms form a double bond, provided that $R^4$ or $R^7$ is a moiety of Formula IIIa:

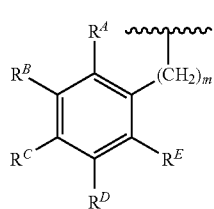

wherein:
m is 0, 1, 2, 3, or 4;
$R^A, R^B, R^C, R^D$, and $R^E$ are independently selected from a group of hydrogen, halogen, hydroxyl, alkyl, alkoxyl, halogenated alkyl, mercaptoalkyl, alkenyl, alkynyl, cycloalkyl, aryl, cyano, thiazolyl, triazolyl, imidazolyl, tetrazolyl, benzothiazolyl, and benzoimidazolyl; or
$R^{3a}, R^4, R^{4a}, R^5, R^{5a}, R^6, R^{6a}, R^7$ and $R^{7a}$ are hydrogen, and $R^3$ is a moiety of Formula IIIa; or a pharmaceutically acceptable salt thereof, provided that said compound is not 3-(4-phenyl-1,2,3,6-tetrahydro-1-pyridyl)-1-propanesulfonic acid.

4. The pharmaceutical composition of claim 3, wherein said pharmaceutical composition further comprises a pharmaceutically acceptable acid, base, buffering agent, inorganic salt, solvent.

5. The pharmaceutical composition of claim 3, wherein said compound is dissolved in a liquid pharmaceutically acceptable vehicle.

6. The pharmaceutical composition of claim 3, wherein said compound is present as a homogenous mixture in a capsule or pill.

7. The pharmaceutical composition of claim 3, wherein said compound is:

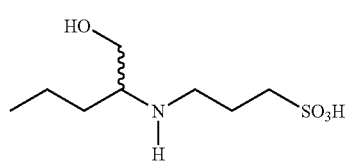

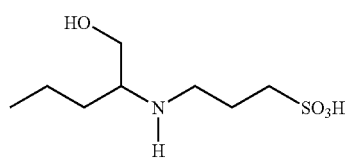

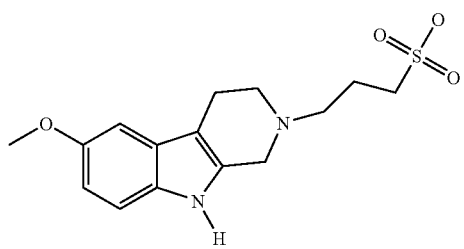

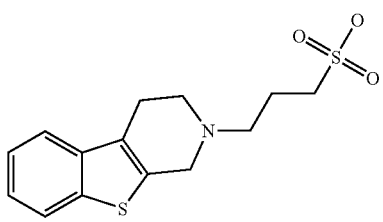

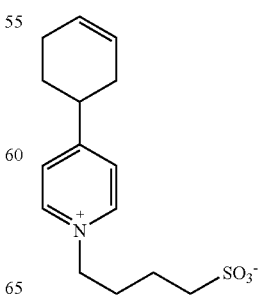

-continued

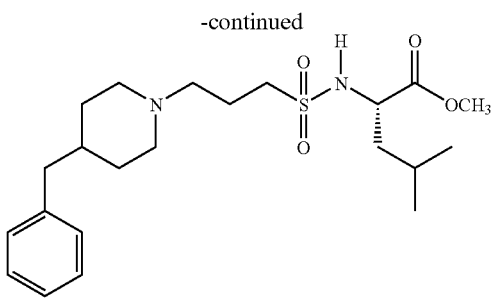

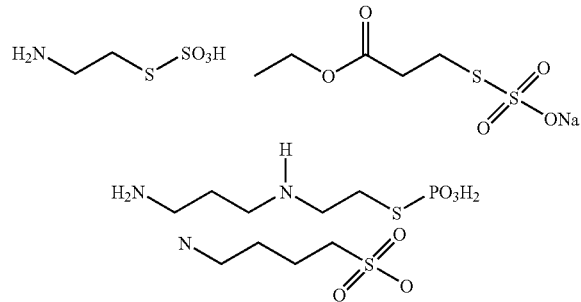

or a pharmaceutically acceptable salt thereof.

8. The compound of claim 1, wherein said compound is:

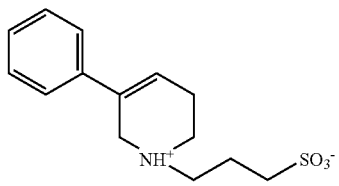

or a pharmaceutically acceptable salt thereof.

9. The compound of claim 1, wherein A is oxygen.

10. The compound of claim 1, wherein n is 3.

11. The compound of claim 1, wherein m is 0.

12. The compound of claim 1, wherein $R^A$, $R^B$, $R^C$, $R^D$ and $R^E$ are each hydrogen.

13. The compound of claim 1, wherein $R^3$ and $R^4$ are taken together with the carbon atoms to which they are attached to form a double bond.

14. The compound of claim 1, wherein $R^3$, $R^{3a}$, $R^5$, $R^{5a}$, $R^6$, $R^{6a}$, $R^7$ and $R^{7a}$ are each hydrogen.

* * * * *